United States Patent
May et al.

(10) Patent No.: US 9,879,251 B2
(45) Date of Patent: Jan. 30, 2018

(54) MICROBIAL ELECTROSYNTHETIC CELLS

(71) Applicant: MUSC FOUNDATION FOR RESEARCH DEVELOPMENT, Charleston, SC (US)

(72) Inventors: Harold D. May, Charleston, SC (US); Christopher W. Marshall, Charleston, SC (US); Edward V. Labelle, Charleston, SC (US)

(73) Assignee: MEDICAL UNIVERSITY OF SOUTH CAROLINA, Charleston, SC (US)

( * ) Notice: Subject to any disclaimer, the term of this patent is extended or adjusted under 35 U.S.C. 154(b) by 0 days.

(21) Appl. No.: 14/427,374

(22) PCT Filed: Sep. 17, 2013

(86) PCT No.: PCT/US2013/060131
§ 371 (c)(1),
(2) Date: Mar. 11, 2015

(87) PCT Pub. No.: WO2014/043690
PCT Pub. Date: Mar. 20, 2014

(65) Prior Publication Data
US 2015/0259669 A1    Sep. 17, 2015

Related U.S. Application Data

(60) Provisional application No. 61/701,827, filed on Sep. 17, 2012, provisional application No. 61/733,308, filed on Dec. 4, 2012.

(51) Int. Cl.
| | |
|---|---|
| *C12N 13/00* | (2006.01) |
| *C12N 1/20* | (2006.01) |
| *C12N 1/36* | (2006.01) |
| *C12P 7/54* | (2006.01) |
| *C12P 3/00* | (2006.01) |
| *C12P 39/00* | (2006.01) |
| *C12P 5/02* | (2006.01) |
| *C12P 7/52* | (2006.01) |
| *C12P 7/62* | (2006.01) |

(52) U.S. Cl.
CPC .............. *C12N 13/00* (2013.01); *C12N 1/20* (2013.01); *C12N 1/36* (2013.01); *C12P 3/00* (2013.01); *C12P 5/023* (2013.01); *C12P 7/52* (2013.01); *C12P 7/54* (2013.01); *C12P 39/00* (2013.01); *C12P 7/625* (2013.01); *Y02E 50/343* (2013.01)

(58) Field of Classification Search
CPC .. C12N 13/00; C12N 1/36; C12N 1/20; C12P 7/54; C12P 39/00; C12P 7/52; C12P 5/023; C12P 3/00; C12P 7/625; Y02E 50/343
See application file for complete search history.

(56) References Cited

U.S. PATENT DOCUMENTS

| 5,871,980 A | 2/1999 | Naylor et al. |
|---|---|---|
| 2009/0317882 A1* | 12/2009 | Cheng .............. C12M 21/04 435/167 |
| 2011/0123835 A1 | 5/2011 | Girguis et al. |
| 2011/0177564 A1 | 7/2011 | Stephanopoulos |
| 2012/0199492 A1 | 8/2012 | Jin et al. |

FOREIGN PATENT DOCUMENTS

| WO | WO 2009/008709 | 1/2009 |
|---|---|---|
| WO | WO 2009/070022 | 6/2009 |
| WO | WO 2010/068994 | 6/2010 |
| WO | WO 2011/087821 | 7/2011 |

OTHER PUBLICATIONS

Chae et al., "Selective inhibition of methanogens for the improvement of biohydrogen production in microbial electrolysis cells," *International Journal of Hydrogen Energy*, 35(24):13379-13386, 2009.

Cheng et al., "Application of biocathode in microbial fuel cells: cell performance and microbial community," *Applied Microbiology and Biotechnology*, 79(3):379-388, 2008.

Croese et al., "Analysis of the microbial community of the biocathode of a hydrogen-producing microbial electrolysis cell," *Applied Microbiology and Biotechnology*, 92(5):1083-1093, 2011.

Duhamel et al., "Microbioal composition of chlorinated ethane-degrading cultures dominated by *Dehalcoccoides*," *FEMS Microbiology Ecology*, 58(3):538-549, 2006.

Liu et al., "Chemical inhibitors of methanogensis and putative applications," *Applied Microbiology and Biotechnology*, 89(5):1333-1340, 2010.

Marshall et al., "Long-term operation of microbial electrosynthesis systems improves acetate production by autotrophic microbiomes," *Environmental Science & Technology*, 47(11):6023-6029, 2013.

Rabaey et al., "Metabolic and practical considerations on microbial electrosynethsis," *Current Opinion in Biotechnology*, 22(3):371-377, 2011.

Srikanth et al., "Microaerophilic microenvironment at biocathode enhances electrogensis with simultaneous synthesis of polyhdroxyalkanoates (PHA) in bioelectrochemcial system (BES)," *Bioresource Technology*, 125:291-299, 2012.

Supplementary European Search Report issued in European Application No. 13837377, dated Apr. 16, 2016.

Venkata Mohan et al., "Microbial catalyzed electrochemical systems: A bio-factory with multi-facet applications," *Bioresource Technology*, 165:355-364, 2014.

(Continued)

*Primary Examiner* — Renee Claytor
*Assistant Examiner* — Susan E. Fernandez
(74) *Attorney, Agent, or Firm* — Parker Highlander PLLC

(57) ABSTRACT

Methods are provided for microbial electrosynthesis of $H_2$ and organic compounds such as methane and acetate. Method of producing mature electrosynthetic microbial populations by continuous culture is also provided. Microbial populations produced in accordance with the embodiments as shown to efficiently synthesize $H_2$, methane and acetate in the presence of $CO_2$ and a voltage potential. The production of biodegradable and renewable plastics from electricity and carbon dioxide is also disclosed.

16 Claims, 26 Drawing Sheets

(56) References Cited

OTHER PUBLICATIONS

Aulenta et al., "Linking Bacterial Metabolism to Graphite Cathodes: Electrochemical Insights into the H(2)-Producing Capability of *Desulfovibrio* sp." *ChemSusChem*, 5:1080-1085, 2012.
Bar-Even et al., "A survey of carbon fixation pathways through a quantitative lens," *J. Exp. Botany*, 63(6):2325-42, 2012.
Braun and Gottschalk, "*Acetobacterium wieringae* sp. nov., a new species producing acetic acid from molecular hydrogen and carbon dioxide," *Zentralblatt für Bakteriologie Mikrobiologie und Hygiene: I. Abt Originale C: Allgemeine, angewandte und ökologische Mikrobiologie*, 3(3), 368-376, 1982.
Cao et al., "A completely anoxic microbial fuel cell using a photo-biocathode for cathodic carbon dioxide reduction," *Energy Environ. Sci.*, 2:498-501, 2009.
Cheng et al., "Direct biological conversion of electrical current into methane by electromethanogenesis," *Environ. Sci. Technol.*, 43:3953-3958, 2009.
Cheng and Logan "Sustainable and efficient biohydrogen production via electrohydrogenesis," *Proc. Natl. Acad. Sci. U.S.A*, 104:18871-18873, 2007.
Demler and Weuster-Botz, "Reaction engineering analysis of hydrogenotrophic production of acetic acid by Acetobacterium woodii," *Biotechnol. Bioeng.*, 108(2):470-4, 2011.
Drake et al., "Old acetogens, new light," *Ann. N.Y. Acad. Sci.*, 1125:100-128, 2008.
Gunsalus et al., "Preparation of coenzyme M analogues and their activity in the methyl coenzyme M reductase system of Methanobacterium thermotophicum," Biochemistry, 17(12):2374-2376, 1978.
Kasemsap et al., "Batch production of polyhydroxyalkanoate by low-polyphosphate-content activated sludge at varying pH," *Bioresource Technology*, 98:1020-1027, 2007.
Labelle et al., "Influence of Acidic pH on hydrogen and acetate production by an electrosynthetic micriobome," *PLOS One.*, 9(10):e109935, 2014.
Li et al., "Integrated Electromicrobial Conversion of $CO_2$ to Higher Alcohols," *Science*, 335:1596, 2012.
Logan et al., "Microbial fuel cells: methodology and technology," *Environ. Sci. Technol.*, 40:5181-5192, 2006.
Logan, "Exoelectrogenic bacteria that power microbial fuel cells," *Nat. Rev. Micro.*, 7:375-381, 2009.
Lovley, "Bug juice: harvesting electricity with microorganisms," *Nature Reviews Microbiology*, 4:497-508, 2006.
Marshall et al., "Electrosynthesis of commodity chemicals by autotrophic microbial community," *Applied and Environmental Microbiology*, 78(23):8412-8420, 2012.
McLean et al., "Quantification of electron transfer rates to a solid phase electron acceptor through the stages of biofilm formation from single cells to multicellular communities," *Environ. Sci. Technol.*, 44(7):2721-7, 2010.
Nevin et al., "Electrosyntehsis of organic compounds from carbon dioxide is catalyzed b ya diversity of acetogenic microorganisms," *Applied and Environmental Microbiology*, 77(9):2882-2886, 2011.
Nevin et al., "Microbial electrosynthesis: Feeding microbes electricity to convert carbon dioxide and water to multicarbon extracellular organic compounds," *mBio*, 1(2):1-4, 2010.
Parrondo et al., "A note—production of vinegar from whey," *J. Institute Brewing*, 109(4):356-358, 2003.
PCT International Search Report and Written Opinion issued in International Patent Application No. PCT/US2013/060131, dated Dec. 23, 2013.
Pieja et al., "Poly-3-hydroxybutyrate metabolism in the type II methanotroph Methylocystis parvus OBBP," Applied and Enviornmental Microbiology, 77:6012-6019, 2011.
Pisciotta et al., "Enrichment of microbial electrolysis cell (MEC) biocathodes from sediment microbial fuel cell (sMFC) bioanodes," *Appl. Environ. Microbiol.*, 78(15):5212-9, 2012.
Rabaey and Rozendal, "Microbial electrosynthesis—revisiting the electrical route for microbial production," *Nature Reviews. Microbiology*, 8:706-716, 2010.
Ren et al., "Time-course correlation of biofilm properties and electrochemical performance in single-chamber microbial fuel cells," *Bioresour. Technol.*, 102(1):416-21, 2011.
Rozendal et al., "Hydrogen production with a microbial biocathode," *Environ. Sci. Technol.*, 42:629-634, 2008.
Schloss et al., "Introducing mothur: Open-Source, Platform-Independent, Community-Supported Software for Describing and Comparing Microbial Communities," *Appl. Environ. Microbiol.*, 75:7537-7541, 2009.
Steinbusch et al., "Bioelectrochemical ethanol production through mediated acetate reduction by mixed cultures," *Environ. Sci. Technol.*, 44:513-517, 2010.
Summers et al., "Direct exchange of electrons within aggregates of an evolved syntrophic coculture of anaerobic bacteria," *Science*, 330:1413-1415, 2010.
Villano et al., "Bioelectrochemical reduction of CO(2) to CH(4) via direct and indirect extracellular electron transfer by a hydrogenophilic methanogenic culture," *Bioresour. Technol.* 101:3085-3090, 2010.
Zhang et al., "Improved cathode materials for microbial electrosynthesis," *Energy Environ. Sci.*, 6(1):217-224, 2013.
May et al., "The bioelectrosynthesis of acetate," with Supplemental Data and Information, *Current Opinion in Biotechnology*, 42:225-233, 2016.

\* cited by examiner

MICROBIAL ELECTROSYNTHETIC CELLS

This application is a national phase application under 35 U.S.C. §371 of International Application No. PCT/US2013/060131, filed Sep. 17, 2013, which claims the benefit of priority to U.S. Provisional Patent Application No. 61/701,827, filed Sep. 17, 2012, and U.S. Provisional Patent Application No. 61/733,308, filed Dec. 4, 2012. The entire contents of the above-referenced disclosures are specifically incorporated herein by reference.

The invention was made with government support under Grant No. DE-AR0000089 awarded by the United States Department of Energy. The government has certain rights in the invention.

INCORPORATION OF SEQUENCE LISTING

The sequence listing that is contained in the file named "MESCP0069US_ST25.txt", which is 2 KB (as measured in Microsoft Windows®) and was created on Feb. 17, 2015, is filed herewith by electronic submission and is incorporated by reference herein.

BACKGROUND OF THE INVENTION

1. Field of the Invention

The present invention relates generally to the fields of electrochemical synthesis and microbiology. More particularly, it concerns methods for microbial electrosynthesis of hydrogen, organic compounds, and bioplastics and microbial populations for use in such methods.

2. Description of Related Art

World economies, in particular that of the U.S., are heavily reliant on the use of fossil-based carbon to produce many commodity chemicals and fuels. However, due to supply difficulties, the inevitable decline of these resources, increased world demand and environmental concerns, a shift away from coal and oil to alternatives such as natural gas, solar, and wind is occurring. However, most of these energy sources are either limited by fluctuations in price and availability or are nonrenewable as in the case of natural gas. These factors have encouraged research into the development of renewable energy technologies powered by microbes. Of particular interest are microorganisms that can capture the global greenhouse gas $CO_2$ and convert it to a valuable commodity, such as a fuel or value-added chemicals.

Bioelectrochemical systems (BESs) include microbial fuel cells (MFCs), microbial electrolysis cells (MECs), and electrosynthetic biocathodes (Cheng et al. 2005; Logan et al. 2006; Lovely D R 2006; Rabaey et al. 2010). Of these, the bioanodes of MFCs and MECs have been the most intensively investigated. The newest and arguably most promising of these technologies is the generation of valuable chemicals by electrosynthesis. Microbial electrosynthesis requires microorganisms to catalyze the reduction of $CO_2$ by consuming electrons on a cathode in a BES. However, to date, efficient microbial conversion of $CO_2$ into usable commodity chemicals, such as $H_2$, organics, and bioplastics, has not been demonstrated in a bioelectrical system.

SUMMARY OF THE INVENTION

In a first embodiment there is provided a method for producing a mature electrosynthetic microbial population comprising (a) culturing a microbial population mixture in a media at a cathode of an electrochemical cell; and (b) maintaining the microbial population mixture in the presence of a cathode voltage potential for at least 30 days, thereby producing a mature electrosynthetic microbial population. In some aspects, the microbial population mixture is maintained in the presence of an average cathode voltage potential of about −300 to −1000 mV (vs. SHE). For example, the average cathode voltage potential can be between −300 to −800 mV, −300 to −600 mV or −400 to −600 mV (e.g., average cathode voltage potential of about −590 mV). In some aspects, the microbial culture is maintained in the presence of constant cathode voltage potential of between −300 to −800 mV, −300 to −600 mV or −400 to −600 mV. In further aspects, the microbial population mixture is maintained in the presence of a cathode voltage potential for at least 40, 50, 60, 70, 80, 90, 100, 110, 120, 130, 140, 150, 160, 170, 180, 190 or 200 days (e.g., for between about 60 and 180 days). In a further aspect, the cathode voltage potential is applied intermittently. In yet further aspects, a method for producing a mature electrosynthetic microbial population according to the embodiments is further defined as a method for bioelectric synthesis of $H_2$ or organic compounds and further comprises a step of (c) collecting $H_2$ or organic compounds from the electrochemical cell.

Thus, in a further embodiment, a method for bioelectric synthesis of $H_2$ or organic compounds is provided comprising (a) culturing an electrosynthetic microbial population of the embodiments in a media at a cathode of an electrochemical cell; and (b) maintaining the microbial culture in the electrochemical cell in the presence of a cathode voltage potential and $CO_2$, thereby producing $H_2$ and/or organic compounds.

In still a further embodiment there is provided a method for bioelectric production of organic compounds comprising (a) culturing a microbial population (e.g., a microbial population of the instant embodiments) in a media at a cathode of an electrochemical cell, wherein the microbial population produces methane in the presence of a cathode voltage potential; and (b) adding a methanogenic inhibitor to the microbial population thereby reducing methane production and increasing production of other organic compounds. For example, in some aspects, a method of the embodiments can be defined as a method for selectively producing acetate. In some aspects, a methanogenic inhibitor for use according to the embodiments is a methyl reductase inhibitor. For example, the methyl reductase inhibitor can be 2-bromoethanesulfonic acid (BESA) or 2-chloroethanesulfonic acid (CESA).

In a further embodiment there is provided a method for bioelectric production of acetate comprising (a) culturing an electroacetogenic microbial population (e.g., a population of the instant embodiments) in a media and in the presence of a $CO_2$ source at the cathode of an electrochemical cell; (b) culturing an methanotrophic microbial population (e.g., an anaerobic microbial population) in a media and in the presence of a methane source at the anode of the electrochemical cell; and (c) applying a voltage potential to the electrochemical cell, thereby oxidizing methane at the anode and producing acetate at the cathode. In some aspects, the anode is comprised in a chamber that is essentially free of $O_2$. In some aspects, the microbial population mixture is maintained in the presence of an average cathode voltage potential of about −300 to −1000 mV (vs. SHE). For example, the average cathode voltage potential can be between −300 to −800 mV, −300 to −600 mV or −500 to −600 mV (e.g., average cathode voltage potential of about −590 mV). In further aspects, the microbial population mixture is maintained in the presence of a cathode voltage potential for at least 40, 50, 60, 70, 80, 90, 100, 110, 120, 130, 140, 150, 160, 170, 180, 190 or 200 days (e.g., for between about 40 and 180 days). In yet further aspects, the method may further comprise a step (d) of collecting acetate from the electrochemical cell and, optionally, a step (e) of feeding the collected acetate into a further bioreactor.

Some aspects of the embodiments concern culturing a microbial population (e.g., a population mixture or a mature microbial population) in a media at a cathode of an electrochemical cell. Accordingly, in some cases, the media at the cathode is exchanged periodically. For example, the media can be exchanged on average every 5 to 40, 10 to 40 or 10 to 30 days. In further aspects, the cathode is supplied with a continuous in flow of fresh media. Likewise, in some aspects, an electrochemical cell of the embodiments is periodically flushed with $CO_2$, such as flushed on average every 3 to 10 days. In still further aspects the electrochemical cell is supplied with a continuous in flow of $CO_2$. In certain aspects, the microbial population is cultured in a cathode chamber of an electrochemical cell.

Some aspects of the embodiments concern culturing a microbial population in a media at an anode of an electrochemical cell. Accordingly, in some cases, the media at the cathode is exchanged periodically. For example, the media can be exchanged on average every 5 to 40, 10 to 40 or 10 to 30 days. In further aspects, the anode is supplied with a continuous in flow of fresh media. Likewise, the anode chamber is flushed with methane periodically. For example, the anode chamber may be flushed with methane on average every 5 to 40, 10 to 40 or 10 to 30 days. In further aspects, the anode chamber is supplied with a continuous flow of methane. Methods of culturing microbes in conjunction with an anode (and microbial populations for such cultures) are provided in U.S. Patent Publn. No. 2011/0123835, incorporated herein by reference.

Certain aspects of the embodiments concern culturing a microbial population mixture in an electrochemical cell. For example, the mixture can comprise bacteria from at least one, two, three or four families selected from the group consisting of Eubaceriaceae, Campylobacteraceae, Helicobacteraceae, Porphyromonadaceae, WCHB1-69, Spirochaetaceae, Deferribacteraceae, Rhodobacteraceae, Synergistaceae and Rhodocyclaceae. Thus, in some aspects, the microbial population mixture comprises bacteria from the Helicobacteraceae, WCHB1-69, Spirochaetaceae, and/or Synergistaceae families. In some specific aspects the mixture comprises bacteria from the genus *Acetobacterium, Sulfurospirillum, Wolinella, Paludibacter, Spirochaeta, Geovibrio* and/or *Azovibrio*. In further cases a microbial population mixture comprises archaea from the Methanobacteriaceae family, such as archaea from the *methanobacterium* and/or *methanobrevibacter* genus.

In a further embodiment there is provided a mature electrosynthetic microbial population (e.g., microbial mixtures that have been matured by methods of the embodiments). In some aspects, a mature electrosynthetic microbial population comprises archaea, such as archaea of the Methanobacteriaceae family. For example, the mature electrosynthetic microbial population can comprise at least about 40%, 50%, 60%, 70% or 80% archaea from the genus *methanobacterium* (relative to the total archaea content of the population). In further aspects, a mature electrosynthetic microbial population comprises bacteria, such as bacteria of the Eubaceriaceae, Campylobacteraceae, Helicobacteraceae, Porphyromonadaceae, WCHB1-69, Spirochaetaceae, Deferribacteraceae, Rhodobacteraceae, Synergistaceae and/or Rhodocyclaceae family. For example, the mature electrosynthetic microbial population can comprise at least about 5%, 10%, 15%, 20% or 25% bacteria from the Helicobacteraceae, WCHB1-69, Spirochaetaceae, and/or Synergistaceae families (relative to the total bacterial content of the population). In another example, the mature electrosynthetic microbial population can comprise at least about 5%, 10%, 15%, 20% or 25% bacteria from the genus *Acetobacterium, Sulfurospirillum, Wolinella, Paludibacter, Spirochaeta, Geovibrio* and/or *Azovibrio* (relative to the total bacterial content of the population). Thus, in some specific aspects, a mature electrosynthetic microbial population comprises about or at least about the content of one or more of the organisms as shown in Tables 2 or 3 (e.g., for the 108 day time point). In some further aspects, a mature electrosynthetic microbial population of the embodiments does not comprise (or is essentially free of) *Sporomusa ovata*.

A wide range of materials can be used as the material for a cathode and/or anode of an electrochemical cell of the embodiments. For example, the cathode and/or anode can comprise carbon paper, carbon cloth, carbon felt, carbon wool, carbon foam, graphite, porous graphite, graphite powder, graphene, carbon nanotubes, electrospun carbon fibers, a conductive polymer, platinum, palladium, titanium, gold, silver, nickel, copper, tin, iron, cobalt, tungsten, stainless steel, and combinations thereof. Thus, in certain aspects, the cathode and/or anode is a graphite cathode and/or anode, such as a graphite granule cathode and/or anode. In yet further aspects the cathode and/or anode is a steel cathode and/or anode.

As detailed above, in certain aspects, a method of the embodiments is further defined as a method for bioelectric synthesis of $H_2$ and/or organic compounds and further comprises the step of (c) collecting $H_2$ or organic compounds from the electrochemical cell (e.g., from a cathode chamber of an electrochemical cell). For example, in some aspects, a method of the embodiments is further defined as a method for $H_2$ production. In some aspects, the microbial population at the cathode is maintained in or has been exposed to an acidic pH. For example, the acidic pH can be between about 3.0 and 5.0 (e.g., between about 3.5 and 5.0 or between about 4.0 and 5.0). In other aspects, the pH at the cathode is maintained at less than 5.0. In further aspects, a method of the embodiments is further defined as a method for production of organic compounds, such as mixtures of compounds comprising methane. Organic compounds that can be produced according to the embodiments include, without limitation, acetate, butyrate, isobutyrate, propionate, 3-hydroxypropionate, 3-hydroxybutyrate, formate or alcohols. Examples of alcohols include, but are not limited to, ethanol, isobutanol or butanol. In some aspects, the method my further comprise contacting the microbial culture with a methyl reductase inhibitor, thereby selectively promoting acetate production.

In still further embodiments a method is provided for electrosynthesis of polyhydroxyalkanoate (PHA) bioplastics, such as polyhydroxybutyrates. For example, in some aspects, a method comprises mixing $H_2$ and/or organic compounds (e.g., methane, acetate, butyrate, isobutyrate, propionate, 3-hydroxypropionate, 3-hydroxybutyrate, formate, or alcohols) produced by the methods detailed above with oxygen in a reaction chamber that comprises a second microbial population, thereby producing a PHA bioplastic. Preferably such a method further comprises collecting or isolating the PHA bioplastic compounds from the second microbial population. Thus, in some aspects, a method for bioelectric synthesis of bioplastics is provided comprising: (a) culturing an electrosynthetic microbial population (e.g., a population produced a method of the embodiments) in a media at a cathode of an electrochemical cell; (b) maintaining the microbial culture in the electrochemical cell in the presence of a cathode voltage potential and $CO_2$, thereby producing $H_2$ or organic compounds; (c) collecting $H_2$ and/or organic compounds from the cathode of the electrochemical cell; (d) mixing the collected $H_2$ and/or organic compounds with oxygen in a second reaction chamber comprising a second (i.e., PHA-producing) microbial population; (e) maintaining the microbial culture in the second reaction chamber under conditions to promote the production of PHA; and (f) collecting the produced PHA from the cells of the second reaction chamber. In certain aspects, oxygen for mixing with the $H_2$ and/or organic compounds comprises oxygen collected from the anode of an electrochemical cell. In some aspects, the media at the cathode comprises a potassium phosphate buffer.

Thus, some aspects of the embodiments, concern a second microbial population that produces PHA. In some aspects, the second population comprises a methanotroph or methanotrophic community. Such a second microbial population may, in some aspects, comprise *Ralstonia eutropha*, *Escherichia coli*, or *Cupriavidus* or an essentially pure culture of any of the foregoing. In certain cases, the second population is comprised in a nitrogen- or phosphate-limited environment. In further aspects, the second microbial population is a comprised in a second reaction chamber, such as a chamber that is directly connected to the electrochemical cell (e.g., via an anion exchange membrane).

In still a further embodiment there is provided a mixed microbial population (such as a population produced by the methods provided herein) comprising bacteria of the genuses *Acetobacterium*, Rhodobacteraceae, and *Sulfurospirillum*, wherein the population comprises less than 15%, 10%, 9%, 8%, 7%, 6%, 5%, 4%, 3%, 2% or 1% content of bacteria from other species. In further aspects, the population is free or essentially free of archaeal organisms. For example, the population may be a biofilm, such as a biofilm on a conductive substrate (e.g., a cathode). In some aspects, the population is comprised in a bioreactor of the embodiments. In still further aspects, a the population is used in a method for producing a commodity chemical of the embodiments (e.g., acetate).

In yet a further embodiment there is provided a mixed microbial population comprising bacteria of the genuses *Acetobacterium* and *Sulfurospirillum*, wherein the population comprises less than 15%, 10%, 9%, 8%, 7%, 6%, 5%, 4%, 3%, 2% or 1% content of bacteria from other species. In further aspects, the population is free or essentially free of archaeal organisms. For example, the population may be a biofilm, such as a biofilm on a conductive substrate (e.g., a cathode). In some aspects, the population is comprised in a bioreactor of the embodiments. In still further aspects, a the population is used in a method for producing a commodity chemical of the embodiments (e.g., acetate).

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
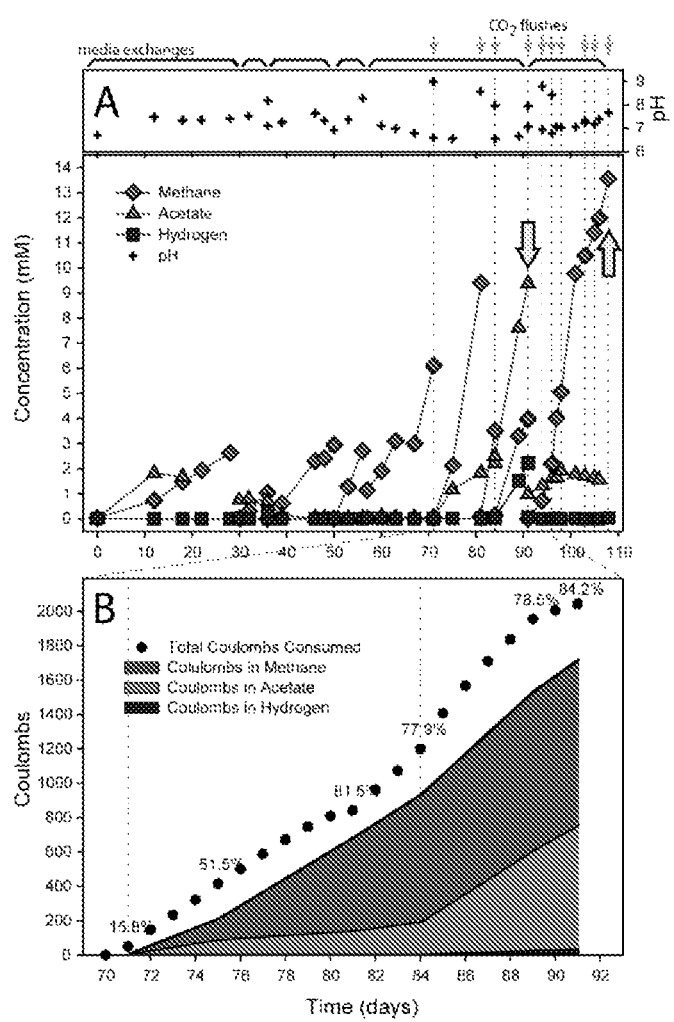
FIG. 1: Development of an electrosynthetic biocathode at −590 mV vs. SHE. (A) Operation of a BES over 108 days, complete replacement of the medium was completed on days 30, 36, 50, 57 and 91. The BES was flushed with 100% $CO_2$ for 30 min on days marked with the gray arrows. (B) Distribution of coulombs in products compared to total coulombs consumed after the first flushing of $CO_2$.

An autotrophic microbial community from brewery wastewater was selected on a cathode of a bioelectrochemical system for the production of valuable commodity chemicals. Methane, acetate and hydrogen were all sustainably and reproducibly generated electrosynthetically at a cathode potential of −590 mV vs. SHE. These are the first studies to demonstrate simultaneous production at rates higher than those previously reported. Furthermore, it is the first report of the electrosynthesis of acetate from $CO_2$ by a mixed microbial community. Differences in laboratory approaches can complicate the comparison of production rates, but sustained rates of methanogenesis and acetogenesis based on cathode volume surpassed what has thus far been discovered for electrosynthesis of these compounds at potentials higher than −700 mV (Table 4).

Microbial communities are notorious for the intricate interactions between microorganisms that frequently result in an efficient and productive process. This is due to the natural selection of microorganisms that will operate in stable consortia. Often it is desirable to select for such consortia to perform useful reactions, e.g., the synthesis of commodity chemicals, particularly when the growth and survival of the microbial community is dependent on those reactions. Extended incubation in a BES with a poised potential and $CO_2$ as the only carbon source served as the selection process for this study. When a potential of −590 mV was applied the result was a community that would electrosynthesize three commodity chemicals: methane, acetate, and hydrogen. A diverse group of active microorganisms were detected on the cathodes with the bacterial community shifting concomitantly with changes in prevailing functional activity (acetogenesis, methanogenesis, hydrogenesis).

The data indicate that at least one member of the community will interact directly with the electrode. *Acetobacterium* spp. were the most prevalent and active Bacteria on the electrode when acetate was produced. Previous attempts to electrosynthesize acetate with *Acetobacterium woodii* failed, although it consumed $H_2$ supplied to the cathode chamber (Nevin et al. 2011). The *Acetobacterium* spp. detected here were strongly associated with the electrode and dominated that population (60.3%). Either these *Acetobacterium* spp. are quite different from *A. woodii* or the microbial community on the electrode affords *Acetobacterium* with advantages unrecognized in the pure culture. The Sphingobacteriales that became dominant as the community progressed have close sequence identities to microorganisms found in electrode reducing biofilms and to hydrogen producing communities. It is possible that microorganisms such as the Sphingobacteriales WCHB1 or *Sulfurospirillum* are oxidizing the electrode and generating hydrogen (similar to *D. paquesii*) that feeds the methanogens and acetogens. Hydrogenotrophic methanogens, *Methanobacterium* in particular (93%), dominated the Archaea detected on the electrode regardless of conditions, and the dominant microbial morphology observed on the electrode when methanogenic was a rod with the appearance of *Methanobacterium*. All three dominant members of the varying community discussed above could potentially be responsible for electrode oxidation.

Methane is the primary component of natural gas (NG), which is widely used in automobiles and electricity generation (Balash et al. 2008; Energy USDo. 2010). It is also the primary source of hydrogen for the production of nitrogen fertilizers (Abram et al. 2005). No biofuel, including electrofuels at this time, could compete economically with the present low price of NG unless subsidized, but the cost of NG will rise as its use increases. In addition, even though a 100 year supply of NG has been estimated (Hackett J T ea 2011) it will eventually be consumed. Although it is by far the cleanest of the fossil fuels, its use still results in the release of climate-changing $CO_2$. Furthermore, the hydraulic fracturing process needed to extract shale gas requires large amounts of water and risks groundwater contamination (Osborn et al. 2011). Electromethane from renewable and sustainable sources of energy will have many of the same benefits but none of these problems, and it could be developed first to supplement NG with the goal of one day replacing it. As this study helps demonstrate, the rates of electromethanogenesis can be improved. At 131 moles of methane per gallon of gasoline equivalent (GGE) (based on 114,000 Btu per gallon of gasoline, 1011 Btu per cu ft $CH_4$, and ideal gas law at 25° C.), the 7 mM day$^{-1}$ rate observed for electromethanogenesis would calculate to 0.05 GGE day$^{-1}$ m$^{-3}$ reactor. Although still requiring improvement, increasing this rate by an order of magnitude would conceivably produce 0.5 GGE each day from a reactor the size of a kitchen appliance. As this technology attracts more attention, rates may increase so that a renewable biogas technology to replace NG may be developed.

Acetic acid is another valuable commodity chemical made from fossil fuels that is used in industrial processes to produce vinyl acetate for paints and adhesives and to a smaller extent vinegar (Cheung et al. 2005). Production for human consumption, e.g. food and cosmetics, requires a higher degree of purity, which is achieved by microbial fermentation (Drake et al. 2008; Parrondo et al. 2003). Acetate is also a key intermediate in the production of biofuels, as it has been shown to be a feedstock for a microbial community to produce ethanol in BESs using methyl viologen as an electron carrier (Steinbusch et al. 2010). Any biosynthetic pathway that involves reducing $CO_2$ to multicarbon compounds must first pass through acetyl-coA and acetate can be readily converted to acetyl-coA by microbes. Hence, electroacetate could be used as a precursor for fuel production or for the production of high purity foods and cosmetics. In addition, a synthetic biology approach could be coupled with electroacetogenesis to produce commodity chemicals. A similar approach was taken by Li et al. with formic acid as a feedstock to make isobutanol (Li et al. 2012).

Hydrogen is used in many industrial processes (e.g. petroleum refining, food additives, fertilizers) and is ordinarily produced from fossil fuels (natural gas particularly). The energy of 1 kg of $H_2$ is approximately equivalent to that in 1 gallon of gasoline (1 GGE). At 2.3 m$^3$ m$^{-3}$ day$^{-1}$ a reactor the size of a large heat pump or refrigerator would produce approximately 0.2 kg of $H_2$ per day, or 0.2 GGE per day. At 2 cents/kWhr (a common industrial rate), a 5 m$^3$ biocathode supplied with 2 V would produce 1 kg/day $H_2$ for $1.68/kg H2. While this would not be economically viable, this is approaching a useful production rate/cost and it is believed that a 10 fold increase (or more) in this rate is still possible.

Electrosynthesis potentially offers a revolutionary way of producing the chemicals needed to sustain modern culture. The carbon source for the process, $CO_2$, is plentiful and inexpensive, the electrons may be supplied from sustainable non-carbon based sources, land mass requirements are negligible and will not compete with food crop production, and being strictly carbon neutral electrosynthesis presents an attractive way to combat climate change. Analogous to the field of microbial fuel cells where intensive research has led to a better understanding of the process and exponential gains in current generation (Logan B E 2009), here it has been demonstrated that the rates of production of multiple commodity chemicals by electrosynthesis can be further increased, thereby advancing the technology closer to becoming competitive with the fossil-carbon based industries.

Global annual production of plastics is 140 million tons and consumes 270 million tons of oil and gas at a market growth rate of 15% per year (DiGregorio 2009, Gerngross 2000). Consumption of bioplastics is 0.4% of the 250,000 kilotons total plastics, at 1000 kilotons, and expected to increase 3 fold by 2020 (Erickson 2012). Biobased chemicals are also projected to comprise 9% of total chemical production (King 2010).

A recent life cycle analysis of polyhydroxybutyrate (PHB) production from biomethane (from anaerobic digestion of waste) and subsequent recycling, in a closed loop, has highlighted significant economic and environmental benefits of this bioplastic (Rostkowski 2012). The application of microbial electrosynthesis by communities may further improve the benefits of a PHB market.

Microbial electrosynthesis fixes carbon dioxide from electricity and microbial catalysts with a high coulombic efficiency. The fixed carbon products can be used as a feedstock in lieu of sugar, surpassing the efficiency of photosynthesis.

Cleaned biogas (methane and carbon dioxide) sells for $0.60-0.80/kg. One kg PHB can be produced from 4-5 kg methane. PHB sells for $4-5/kg (Rostkowski 2012). Both the separation of methane from the liquid phase, and the carbon-carbon bonds formed by polymerization, provide a reliable thermodynamic selection of carbon-fixing biocathodes. By avoiding the production and transportation costs of sugar or waste feedstock, while also storing transient renewable energy in chemicals, several desired goals are achieved for a successful bio-based carbon market. Thus, the conversion of electromethane to higher value products such as bioplastic by this invention is a potentially valuable process for microbial electrosynthesis.

Further studies provided herein detail the performance of acetogenic MESs for over five months. The longevity of the biocatalysts in MESs is an important metric for the realization of this promising technology. Not only did the microorganisms survive for this extended time, the performance actually improved following prolonged incubation.

During the seven day yield test conducted after 121 days of electrosynthetic reactor operation, acetate production reached 17.25 mM $d^{-1}$; a rate that is 100× faster than any pure culture on unmodified graphite electrodes (Nevin et al. 2010). The use of naturally selected electrosynthetic microbiomes and the extended enrichment at −590 mV are partially responsible for the improvements in rates. All of these aforementioned attributes were evident in the reactors given that the biofilm coverage increased, dominant members of the active microbiome persisted, and the acetate production rates increased with prolonged incubation. Another explanation for the increased acetate rates was the higher $CO_2$ concentration available to the microbes during continuous sparging. Acetate formation is thermodynamically more favorable under increasing $CO_2$ concentrations (Bar-Even et al. 2012); thus, the constant sparging with 100% $CO_2$ could contribute to the higher rates observed in this long-term study.

The improvements in production rates could also be partially attributed to the higher Coulombic efficiency observed in the present study compared to the previously reported Coulombic efficiency in reactors. This was most likely due to the minimization of parasitic reactions that were present in the early stages of biofilm development. Since the MESs were originally inoculated from brewery wastewater, aerobic microorganisms could have been present that oxidized acetate while reducing trace oxygen and thus diverting electrons from product formation. Over time, the repeated selective pressure of the biocathode presumably suppressed or eliminated these unwanted reactions. The decrease in richness observed by the phylogenetic analysis supports this hypothesis.

Figure 20:
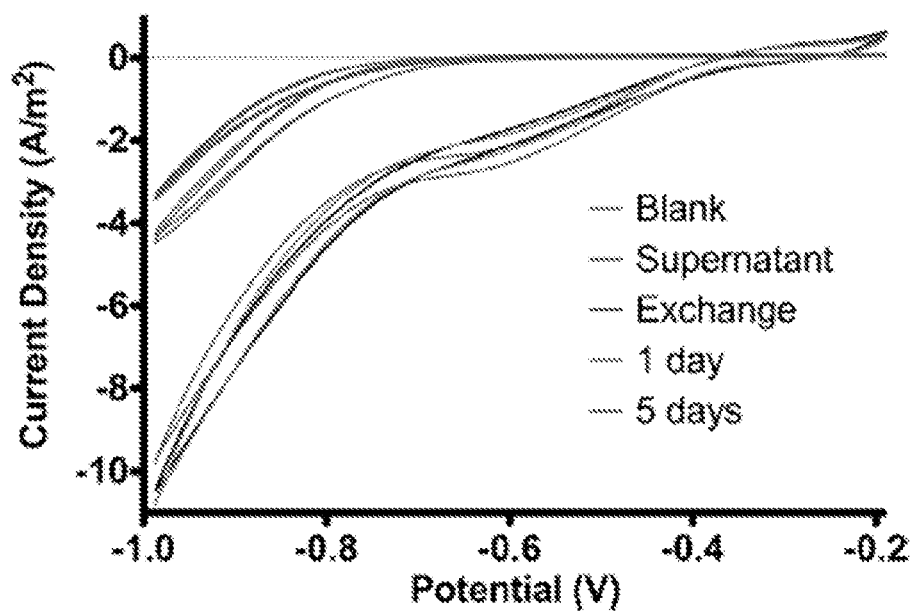
FIG. 20: Cyclic voltammetry on blank growth medium, filtered supernatant from MES 2 (upper traces) and MES 2 immediately after a medium exchange, MES 2 one day after a medium exchange, and MES 2 five days after a medium exchange (lower traces).

Stability was confirmed by the phylogenetic analyses of the active members of the microbiomes. *Acetobacterium* remained the dominant microbiome on the graphite biocathodes. The sequence identity is closely matched to *Acetobacterium wieringae*, an acetogenic bacterium that couples growth to $CO_2$ fixation via the Wood-Ljungdahl pathway (Braun et al. 1982; Drake et al. 2008). It seems likely that microorganisms from the *Acetobacterium* genus are primarily responsible for electroacetogenesis in the MESs, given their continued presence whenever acetate is produced by the biocathode. The mechanism of electron transfer to the acetogens remains to be determined, but electrochemical analysis of this community indicated that direct electron transfer is contributing to the eventual production of acetate, perhaps directly to the acetogens (FIG. 20).

The other major active bacteria on the granules were *Sulfurospirillum* and Rhodobacteraceae, consistent with the community in the original reactor generating acetate. However, it is unclear what role *Sulfurospirillum* and Rhodobacteraceae play despite their prevalence and continued presence in the biocathodes. Rhodobacteraceae increased by 8.1% to a total of 15.9% in MES 1 (MES 2 increased to 18.7%), becoming significant members of the active microbiome on the granular electrode. While some members of the Rhodobacteraceae can use light as an energy source, many do not. Reactors in this study were operated in both the light and the dark, with no observable effect on current or product formation. The sequence identity of the Rhodobacteraceae did not closely match any cultured isolates but was related to environmental clones from nonphotosynthetic sources such as wastewaters and anaerobic digesters. One possibility is that that Rhodobacteraceae (and possibly *Sulfurospirillum*) draw electrons directly from the electrode and produce hydrogen.

Electron micrographs indicated an increase of cells observed on the cathode over time. Increases in electrode-attached biofilm coverage is a common feature of anodes in microbial fuel cells (McLean et al. 2010; Ren et al. 2011), and it appears cathode-associated biofilm development is also possible during electrosynthesis in MESs. Thus, preliminary evidence indicates microbial electrosynthesis systems can employ self-assembling biocatalysts attached to the electrode for product formation.

The increase in cells observed on the cathodes corresponded with an increase in rates of acetate production driven by electrons from an electrode. The highest observed rate of electroacetogenesis in this study was 1 g $L^{-1}$ $d^{-1}$, a rate that approaches the fastest acetogenic rates in bioreactors pressurized with $H_2/CO_2$ gas (Demler et al. 2011). The sustained rates of biocatalysis reported in this study begin to address key issues with taking microbial electrosynthesis to an industrial scale. For example, a 1000 L reactor generating acetic acid at a rate of 1 g $L^{-1}$ cathode vol/day (1 kg acetate produced/day) and a Coulombic efficiency of 69% into acetic acid production (FIG. 18C), would require $0.35 of electricity (assuming 1.5 V, $0.05/kWh, and the present system scales) to produce $0.6 of acetic acid (1 kg). While other cost factors remain to be determined, this promising start will become more favorable as rates and efficiencies increase further, which is likely based on the advances already made with MESs and previously made with MFCs.

Microbial electrosynthesis, such as by the methods provided herein, has the potential to become a carbon-neutral substitute for the fossil fuel dependent chemical and fuel industry. The studies herein clearly demonstrate biocatalyst durability and prolonged product generation, critical components of industrial scale biotechnology processes. Thus, the provided methods, microbial communities and reactors should provide for efficient electrosynthesis of commodity chemicals, gaseous and liquid fuels, and bioplastics.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods of the Studies

Source of Microorganisms and Initial Screening

The biocatalysts described here were enriched from samples taken from a retention basin for brewery wastewater at Palmetto Brewing Company in Charleston, S.C. To screen for initial product formation, the brewery wastewater sludge was used to inoculate 20 ml chambers of small BES reactors equipped with graphite rod cathodes. Reactors were poised from −1000 to −400 mV vs. SHE with the goal of selecting for the highest rate of product formation at the highest potential to limit energy input into the system. Products (acetate and methane) were detected after 28 days of incubation at −590 mV and again after the medium had been exchanged once. Controls without voltage applied were monitored for production due to fermentation of the wastewater. Once production free of fermentation was indicated, inoculum from these reactors was then transferred to larger 3-electrode BES reactors described below in order to further enrich and evaluate the electrosynthetic community.

3— Electrode Bioelectrochemical Systems

Figure 14:
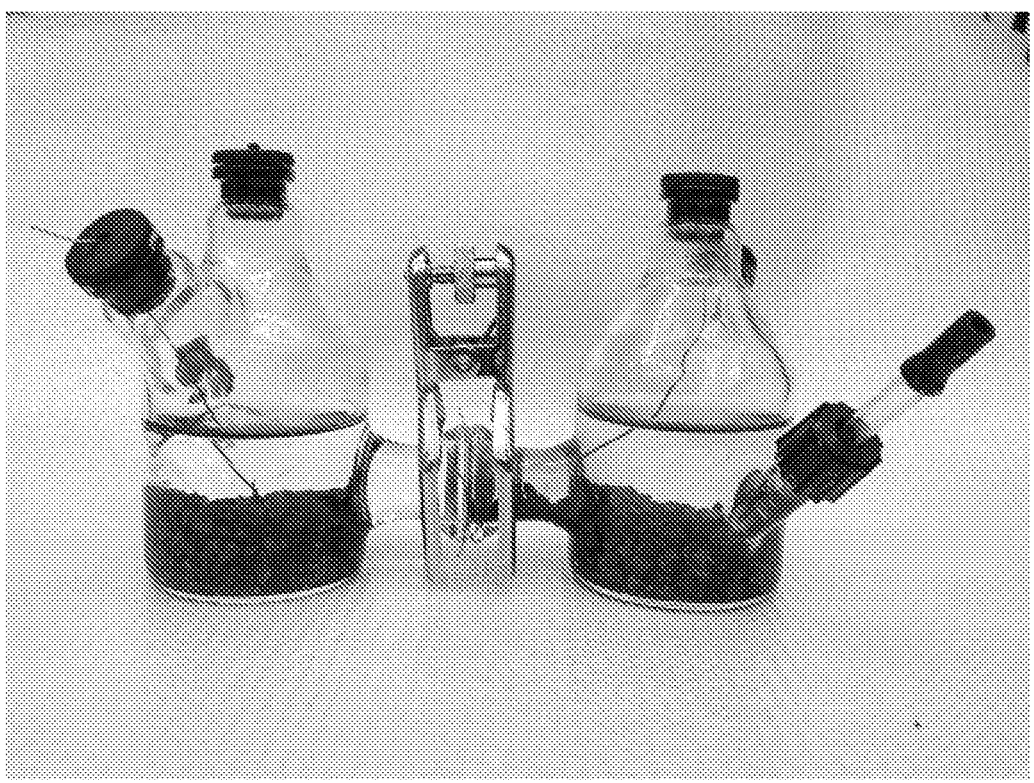
FIG. 14: Two chamber electrochemical cell used for most of the studies described herein. The system was also adapted for continuous flow operation (FIG. 9). Each cell contains graphite granule electrodes linked to a titanium wire. Ports for sampling and application of pH probes and reference electrodes are included. The two chambers are clamped with a cation exchange membrane separating the chambers.
Figure 15:
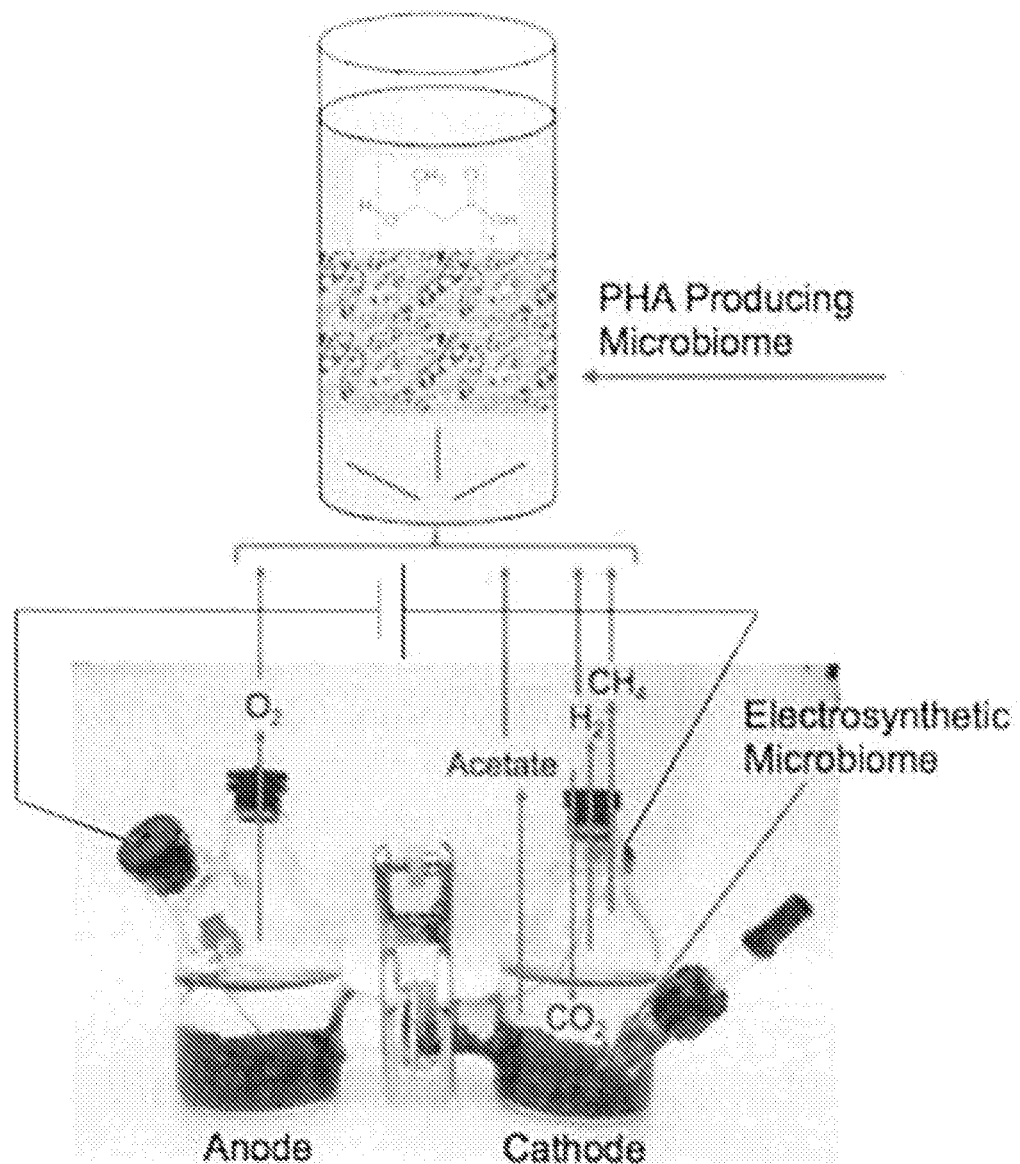
FIG. 15: System to microbially synthesize bioplastics (PHAs) from $CO_2$.

The BESs consisted of two identical custom designed glass chambers (Chemglass Life Sciences, Vineland, N.J.) that had two crimp-seal, butyl rubber sampling ports, a threaded o-ring sealed port for the reference electrode, and a clamped o-ring junction for the membrane (FIG. 14). The total volume of the glass chamber was 150 ml. The two glass chambers were separated by a proton exchange membrane (Nafion 117, fuelcellstore.com) and sealed with an o-ring and clamp. The reference electrode was Ag wire coated with AgCl and immersed in 3M KCl saturated with AgCl (+210 mV vs. SHE). All potentials are reported versus SHE. Both glass chambers contained 30 g dry weight of pretreated graphite granules of heterogeneous sizes approximately 10 mm×5 mm×3 mm and smaller (Showa Denko). Granules were on average 2 g/ml. A 0.9525 cm diameter×3 cm long pretreated graphite rod current collector connected to a 0.065 cm titanium wire was buried in the graphite granule bed. The graphite electrodes were first pretreated by sonication in deionized water and then washed with acetone, 1M hydrochloric acid, 1M sodium hydroxide, and deionized water in succession to remove organic and metal contamination.

The cathode chamber (biotic) was filled with 75 ml of freshwater medium containing per liter: 2.5 g sodium bicarbonate, 0.6 g sodium phosphate monohydrate, 0.25 g ammonium chloride, 0.212 g magnesium chloride, 0.1 g potassium chloride, 0.03 g calcium chloride, 20 ml vitamins solution, 20 ml mineral solution. The vitamin solution contained per liter: 2 mg biotin, 2 mg folic acid, 10 mg pyridoxine-HCl, 5 mg thiamine-HCl×2H$_2$O, 5 mg riboflavin, 5 mg nicotinic acid, 5 mg D-Ca-pantothenate, 0.1 mg vitamin B$_{12}$, 5 mg p-aminobenzoic acid, and 5 mg lipoic acid. The mineral solution contained per liter: 1.5 g nitrilotriacetic acid, 3 g MgSO$_4$×7H$_2$O, 0.5 g MnSO$_4$×H$_2$O, 1 g NaCl, 0.1 g FeSO$_4$×7H$_2$O, 0.152 g CoCl$_2$×6H$_2$O, 0.1 g CaCl$_2$×2H$_2$O, 0.085 g ZnCl$_2$, 0.01 g CuSO$_4$×5H$_2$O, 0.02 g KAl(SO$_4$)$_2$×12H$_2$O, 0.01 g H$_3$BO$_3$, 0.01 g NaMoO$_4$×2H$_2$O, 0.03 g NiCl$_2$×6H$_2$O, 0.3 mg Na$_2$SeO$_3$×5H$_2$O, 0.4 mg Na$_2$WO$_4$×2H$_2$O. The anode chamber (abiotic) contained a similar media composition but without the vitamins or minerals but with increased potassium chloride to 1 g/L and sodium chloride to 2 g/L. The medium was prepared under anaerobic conditions (80:20 vol/vol N$_2$:CO$_2$) and passed to the chambers of the BES in an anaerobic glove bag (Coy Laboratory Products). After transfer of the medium, the BESs were removed from the anaerobic chamber and the headspace was flushed with 80:20 vol/vol N$_2$:CO$_2$ before inoculation. The BESs were operated in batch mode at 25±2° C., and medium exchanges were accomplished by decanting over 90% of the liquid volume, leaving only the granules and what liquid remained in the granular electrode bed. The medium exchanges and subculturing were done in an anaerobic chamber by transferring approximately 10 mL of liquid and a small amount (1-5 grams) of graphite granules from the current-consuming, product-producing reactor into sterile BESs. Where noted, BESs were flushed with 100% CO$_2$ using a long needle aseptically pierced through the stopper into the liquid and another short needle in the headspace as gas effluent. To inhibit methanogenic Archaea and enrich for acetogens, 10 mM of 2-bromoethanesulfonic acid was added at the time of a medium exchange to a reactor actively producing methane and acetate by electrosynthesis.

Electrochemistry

Figure 2:
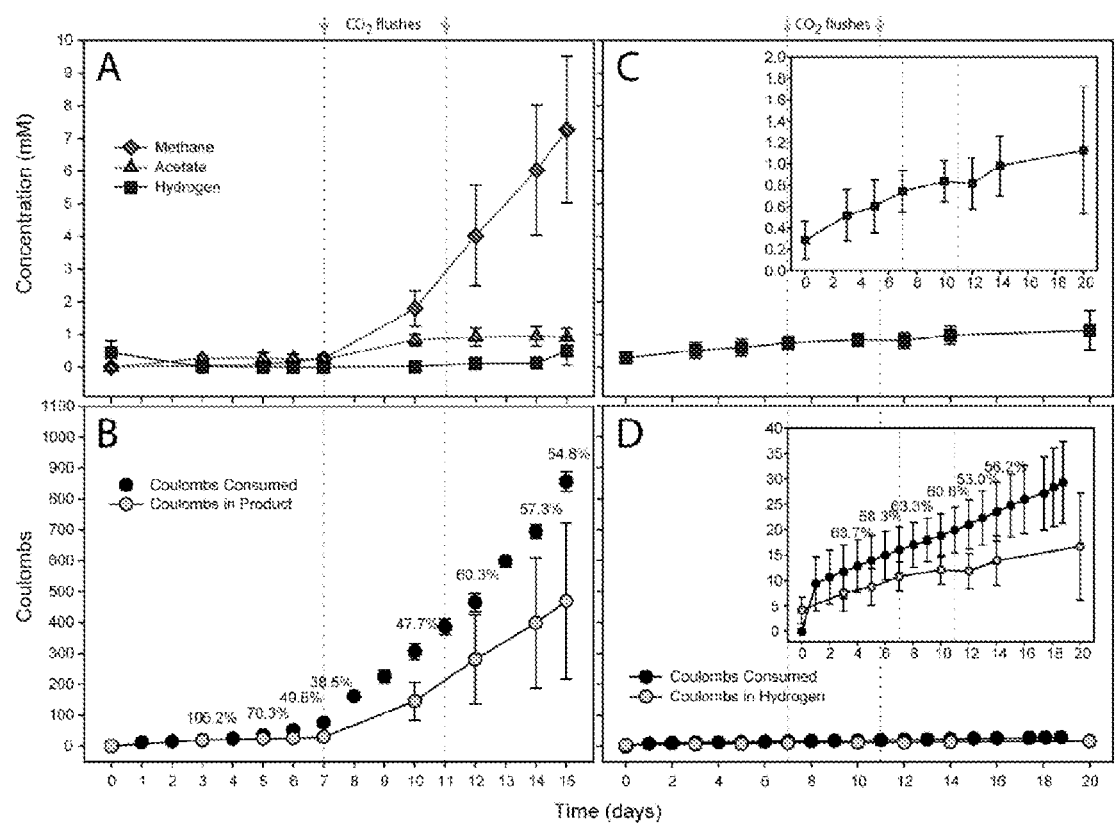
FIG. 2: Replication of biocathodes at −590 mV. Co-production of acetate and methane (A) and coulombs consumed (B) after transferring the brewery waste biocathode. Production of hydrogen (C) and coulombs consumed (D) at −590 mV in abiotic (sterile, uninoculated) control BESs. The BESs were flushed with 100% $CO_2$ for 30 min on days 7 and 11. Error bars are standard deviations, n=3.

During most of the experiments the cathode was poised chronoamperometrically at −590 mV. On day 28 of biocathode operation, the replicate working electrodes (cathodes) shown in FIG. 2 were subjected to cyclic voltammetry (CV). The scan range of the CV was from −200 mV to −1000 mV and the scan rate was 1 mV/second. All electrochemistry was done using a VMP3 potentiostat (Bio-Logic USA). Coulombic efficiencies were calculated by dividing coulombs found in the product ($C_p$) by total coulombs consumed ($C_T$). $C_p$=b*n*F, where b=number of electrons in the product, n=number of moles of product, and F is Faraday's constant 96485 C/mol. $C_T$ was calculated by integrating the area under the current vs. time curve (i-t curve).

Analytical Methods

Fatty acids were measured using an HPLC (Shimadzu) equipped with a UV detector at 210 nm. The mobile phase was 0.005M H$_2$SO$_4$ and had a flow rate of 0.55 ml/min through an Aminex HP-87H column (Bio-Rad, Hercules, Calif.). Methane and hydrogen were measured on a HP6890 GC equipped with a HP-PLOT Molesieve 5 A column (30 m×530 nm×25 nm) and a thermal conductivity detector (TCD). The oven was held at 50° C. for 2 minutes, then increased be 25° C./minute to 170° C. and held for 0.2 minutes. Injector temperature was 120° C. and the detector temperature 250° C. Argon was the carrier gas.

Scanning Electron Microscopy (SEM)

Graphite granules from the cathode were fixed in 2% gluteraldehyde in 0.1M sodium cacodylate buffer for 3 hours. The granules then underwent a 2.5% osmium tetraoxide postfix wash for 1 hour. Then, the granules were dehydrated by a series of ethanol washes (25%, 50%, 75%, 95%, 100%). The samples were sputter coated with gold and palladium with a 100-angstrom coating (Denton Vacuum). Images were taken with a JEOL JSM-5600LV scanning electron microscope.

RNA Extraction

Samples for RNA extraction were either collected directly into Trizol (Invitrogen, for MEC granules) or concentrated onto a Sterivex filter (Millipore, PES membrane, 0.22 μm pore size, for MEC supernatant), which was then stored in Trizol. Samples in Trizol were incubated at room temperature for at least 15 minutes and then frozen at −80° C. until further processing as outlined in the supplemental methods.

RT-PCR Amplification and 16S rRNA Sequencing

To process RNA, glycogen (250 μg ml-1 final concentration) was added to each sample and RNA extracted according to manufacturer's protocol with modifications (Trizol, Life Technologies). Briefly, thawed samples were vortexed and incubated at room temperature to complete cell lysis. Chloroform was added, and samples were incubated for another 3 min at room temperature before phase separation. The aqueous phase was washed with chloroform:isoamyl alcohol, then the RNA was precipitated from the aqueous phase with isopropanol. After 17 h incubation at −20° C., RNA was pelleted, washed twice with 70% ethanol, and re-suspended in nuclease-free water. RNA was purified using an RNeasy kit (Qiagen) following manufacturer instructions, and residual DNA was removed enzymatically (TURBO DNA-free, Ambion).

Reverse transcription (RT) was carried out with 100 ng of total RNA using random hexamers (SuperScript III, Life Technologies) according to manufacturer's instructions. PCR was performed with either universal Bacterial or Archaeal primers for the V1-V3 or V2-V3 region of 16S rRNA (Table 1) with the following final concentrations: 1× Green GoTaq reaction buffer, 1 mM $MgCl_2$, 0.2 mM dNTPs, 0.2 µM forward primer mix (equal molar concentrations of degenerate and less-degenerate primer), 0.2 µM reverse primer, 0.625 U Taq polymerase (Promega), and 0.5 µL of RT reaction per 25 µl PCR reaction volume. Two replicate PCRs were carried out with each of the two following cycling protocols (total of 4 replicates) to maximize priming coverage. The first protocol consisted of an initial denaturing step (94° C., 5 min), 10 amplification steps (45 seconds each of 94° C., 62° C. decreasing 0.5° C. per step, 72° C.), an additional 15 amplification steps (45 seconds each of 94° C., 57° C., 72° C.), followed by a final 10 min extension at 72° C. The second protocol designed to target GC-rich templates (Mamedov et al. 2008) is the same as the first, except all annealing steps were performed for 6 seconds instead of 45.

TABLE 1

List of primers (SEQ ID NOs: 1-4)

| Name[a] | Primer sequence (5'→3')[b] | Ref |
|---|---|---|
| B27F-d | AGAGTTTGATYMTGGCTCAG | (Nercessian et al., 2005) |
| B27F | AGAGTTTGATCCTGGCTCAG | (Edwards et al., 1989) |
| A109F | ACKGCTCAGTAACACGT | (McInerney et al., 1995) |
| U529r[c] | ACCGCGGCKGCTGRC | This study |

[a] "B" indicates bacteria-specific, "A" indicates Archaea-specific, and "U" is universal. Numbers relate to *E. coli* positions. Labels containing "d" indicate more-degenerate primers.
[b] Degenerate and non-degenerate primers for Bacterial-specific primers were mixed in equal molar ratios before using in PCR.
[c] Primer was modified at the 5' end to include multiplex identifiers (barcodes) for each sample as follows: Day 91 supernatant MID1 [5'- ACGAGTGCGT; SEQ ID NO: 5]; Day 91 granules MID5 [5'- ATCAGACACG; SEQ ID NO: 6]; Day 108 supernatant MID3 [5'- AGACGCACTC SEQ ID NO: 7]; Day 108 granules MID7 [5'- CGTGTCTCTA; SEQ ID NO: 8].

All PCR replicates were pooled (4 total), cleaned (Qiagen, PCR Clean-up Kit), and quantified (Nanodrop). Amplicons were sequenced on a PacBio-RS Sequencer (Engencore, LLC) using a 45-minute run time and standard protocols (Eid et al. 2009). The Pacific Biosciences PacBio RS next-generation DNA sequencer Sequencing efforts generated a total of 214,901 circular consensus sequences. Around 30% of the reads (65,943) were removed during sequence pre-processing and 148,958 reads were used in the analysis. The abundance of rRNA, and thereby active microorganisms, can be compared within but not across domains since different specific primers were used to amplify the reverse transcription products from each domain. Pacific Biosciences FASTAQ formatted circular consensus sequences have been submitted to the GenBank Sequence Read Archive under SRA056302.

Taxonomic Classification

Sequences were pre-processed and analyzed using Mothur v. 1.25 and 1.27 (Schloss et al. 2011; Schloss et al. 2009. Briefly, sequences with [low average quality scores (<25 over a rolling window of 10 bp), anomalous read lengths (<4300 bp or >615 bp), an ambiguous base (quality score <1) >8 homopolymers, >1 mismatch to the barcode or primer] were removed. Remaining reads were de-replicated, grouped with similar fragments, and aligned against the Greengenes core database (DeSantis et al. 2006) using kmer searching (8mers) with Needleman-Wunsch global, pairwise alignment methods (Needleman et al. 1970). Primers were then trimmed from each read: the B27f primer corresponds to Greengenes alignment positions 109-136, A109f to positions 455-493, and U529r to positions 2232-2260. Resulting reads shorter than 300 bp or those likely due to sequence error (Huse et al. 2010) or chimeras (Edgar et al. 2011) were removed. Reads were then classified using a Bayesian approach and bootstrap cutoff of 80 (Wang et al. 2007) against the SILVA database (Pruesse et al. 2007).

Example 2—Results of the Initial Culture Studies

Establishing an Autotrophic Biocathode

A 3-electrode BES (FIG. 14) was inoculated from a brewery waste culture that was initially screened in a small 2-electrode BES. The 3-electrode BES was operated for three months at a fixed cathode potential of −590 mV. The electrode was the microbial community's only electron donor and $CO_2$ its only carbon source for growth throughout all experiments. During the first 10 days of incubation, the reactor generated 1.8 mM acetate followed by 2.6 mM of methane over 30 days as the main products from $CO_2$ fixation before the first exchange of the spent growth medium (FIG. 1A). Production rates reached 0.18 mmoles acetate per liter of cathode liquid volume per day (mM $day^{-1}$) and 0.12 mM $day^{-1}$ methane during this initial startup. Subsequently after successive medium exchanges, methanogenesis became the dominant process and reached 0.78 mM $day^{-1}$.

As $CO_2$ was consumed and reduced to methane, the pH in the cathode chamber would frequently exceed 8 (FIG. 1A). To remedy this, 100% $CO_2$ was flushed through the reactor for 30 min, which then lowered the pH of the medium to approximately 6.5. Unexpectedly, this $CO_2$ flush also revived the production of acetate. The increase in acetogenic activity after $CO_2$ flushing resulted in rates reaching 1.02 mM $day^{-1}$ with accumulation of >9 mM in the cathode chamber over 17 days. Methanogenesis also increased in response to the flushing of $CO_2$, reaching a rate of 1.58 mM $day^{-1}$. During the 17 days after the start of $CO_2$ flushing the coulombic efficiency reached 84% (FIG. 1B). This is believed to be the first time co-production of acetate and methane has been shown electrosynthetically.

Replication of the Autotrophic Biocathode

An important question regarding microbial electrosynthesis resides in the ability to generate sustainable and transferable production rates. After 92 days of operation, supernatant and granules were transferred from the initial reactor into 3 replicate BESs poised at −590 mV. After a lag period of about one week, product formation began to increase. Once again, acetate and methane were the predominant products in the replicates; however, the acetate production rate was much lower than that of electromethanogenesis (FIG. 2A). Although acetogenesis did not disappear as it did early on in FIG. 1, the rates were not able to compete with methanogenesis, irrespective of the periodic flushing of the cell with 100% $CO_2$. Over a ten-day period following the initial lag phase, acetate accumulated to 1 mM and methane to 10 mM. The acetate production rate was 0.1 mM $day^{-1}$ and the methane production rate reached 1.3 mM $day^{-1}$ during this period. The coulombic efficiency of the replicates reached 60% (FIG. 2B).

Abiotic (sterile) reactors were also poised at −590 mV to determine if the abiotic accumulation of hydrogen would be sufficient to account for the methane and acetate observed under biotic conditions (FIG. 2C). At the start of each experiment approximately 0.3 mM of hydrogen was immediately produced due to the initial polarization of the cathode. However, from that point forward the abiotic hydrogen production rate was observed at less than 0.045 mM day$^{-1}$ over 20 days with a coulombic efficiency ranging from 53-64%. Thus, this rate of production cannot account for the mM day$^{-1}$ rates of methane and acetate production observed in any of the biotic BESs. Coulombs may have been lost in the biotic and abiotic BESs due to gas leakage through joints in the reactor, bubbles trapped in the graphite bed, and in the case of the biotic BESs electrons accumulated into biomass. Despite the portion of electrons unaccounted for, the total coulombs consumed in the biotic replicates far exceeded what was calculated in the abiotic BESs (FIG. 2B,D), indicating microbial catalysis that could not be explained by abiotic hydrogen formation.

Increased Rates of Electrosynthesis

Figure 3:
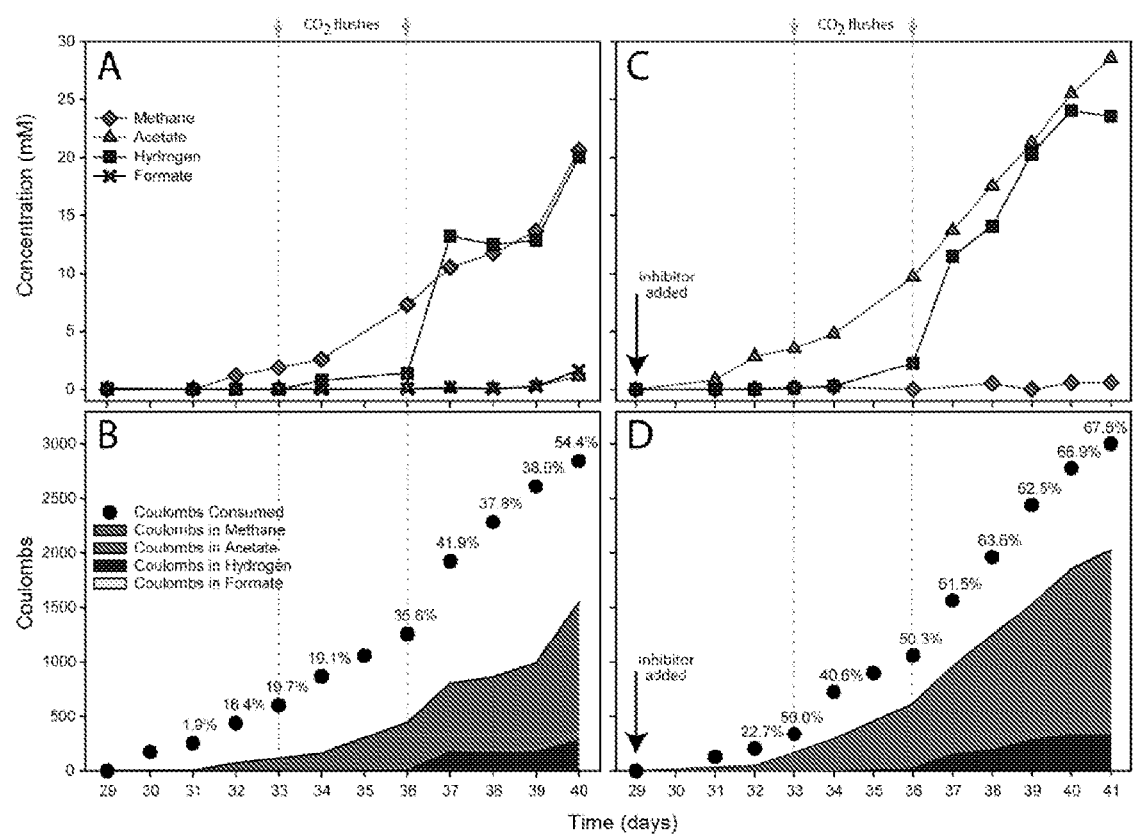
FIG. 3: Increased rates of electrosynthesis. Two of the replicate BESs described in FIG. 2 were incubated further with two more medium exchanges, the last on day 29. (A) Production of acetate, methane, hydrogen, and formate in one BES maintained without inhibitor. (B) Distribution of coulombs consumed and in all products observed in A. (C) Production of acetate and hydrogen in a second BES with 2-bromoethanesulfonic acid added. (D) Distribution of coulombs consumed and in all products observed in C. The BESs were flushed with 100% $CO_2$ on days 33 and 36.

The rates of methane or acetate production could be increased by further enrichment of the electrosynthetic biocathodes or by adding a selective inhibitor. After 29 days of operation with repeated medium exchanges (beginning in FIG. 2), the rate of methanogenesis increased, the co-production of acetate continued, and eventually hydrogen (and occasionally a small amount of formate) was produced (FIG. 3A). The rate of methanogenesis was consistently >1.6 mM day$^{-1}$ and reached a maximum 7 mM day$^{-1}$, accumulating to 1.5 mmoles in the headspace. The acetate production rate remained near that observed in the initial BES reactor (FIG. 1A), close to 1 mM day$^{-1}$. Hydrogen did not accumulate to any significant degree until after extended incubation in the experiments documented in FIGS. 1 and 2. This was also the case for the experiments presented in FIG. 3 where the microbial community had been further enriched and had experienced multiple medium exchanges. Electrohydrogenesis again lagged behind methanogenesis but suddenly after 7 days of reactor operation increased dramatically to more than 4 mM day$^{-1}$, eventually reaching 11.8 mM day and accumulated to 1.5 mmoles (FIG. 3A). Although hydrogen lagged behind methanogenesis, once it started it was produced concurrently with methane. Also after an extended lag, formate and acetate eventually were formed at rates of 1 mM day$^{-1}$ in the methanogenic reactors. The electron recovery (coulombic efficiency) in methane, acetate, formate, and hydrogen was 54% (FIG. 3B). Subsequent transfer cultures in replicate BESs of this community following the establishment of hydrogen production have continued to perform similarly to what is presented in FIG. 3A, generating methane, hydrogen, acetate, and formate.

Co-production of acetate and methane was observed throughout the study (FIGS. 1a, 2a, and 3a), but methanogenesis usually out-competed acetogenesis. This changed upon the addition of the methanogenic inhibitor 2-bromoethanesulfonic acid (FIG. 3C), which resulted in acetogenesis increasing to as high as 4 mM day$^{-1}$. This rate of activity was sustained in the absence of methanogenesis with subsequent transfers of the treated culture to other BESs. Acetate production started 2 days after medium exchange and inhibitor addition, and then increased over the next 10 days accumulating to 28.5 mM. After a lag of 7 days, hydrogen began to be produced by the community and was then generated concomitantly with acetate (similar to what occurred in the methanogenic reactor in FIG. 3A). The overall rate of hydrogen production was 2 mM day$^{-1}$, but reached rates of over 9 mM day$^{-1}$ and accumulated to 1.8 mmoles in the headspace. Electron recovery in acetate and hydrogen from the 2-bromoethanesulfonic acid treated community was 67% (FIG. 3D). The biotic production of hydrogen in the reactor with the inhibitor and in the one without (FIGS. 3A, 3C) exceeded abiotic production by at least 200-fold (FIGS. 2C, 2D).

Figure 4:
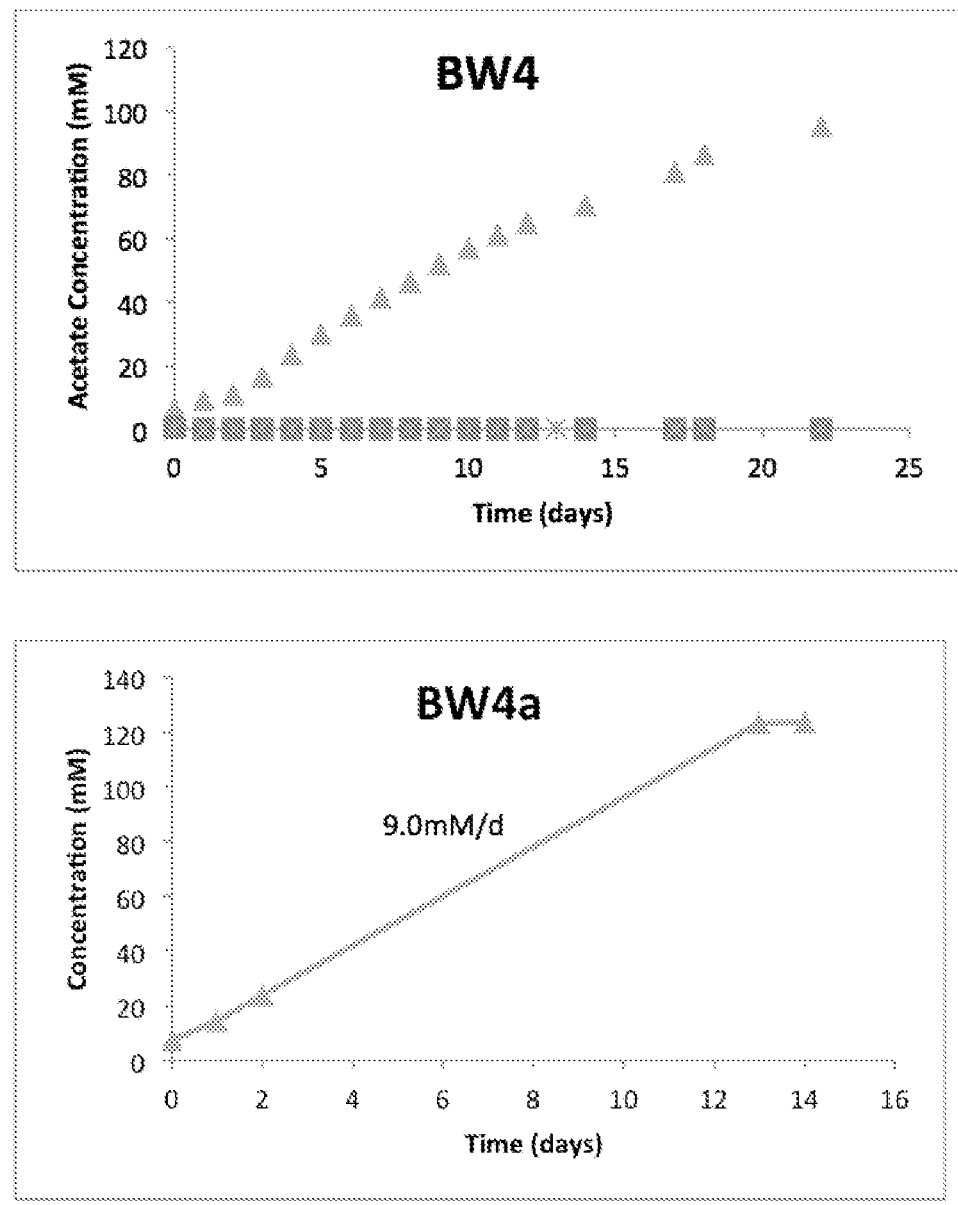
FIG. 4: Increased rates of electroacetogenesis with the biocathode poised at −590 mV vs. SHE during a continuous feeding of $CO_2$ into the cathode liquid.
Figure 5:
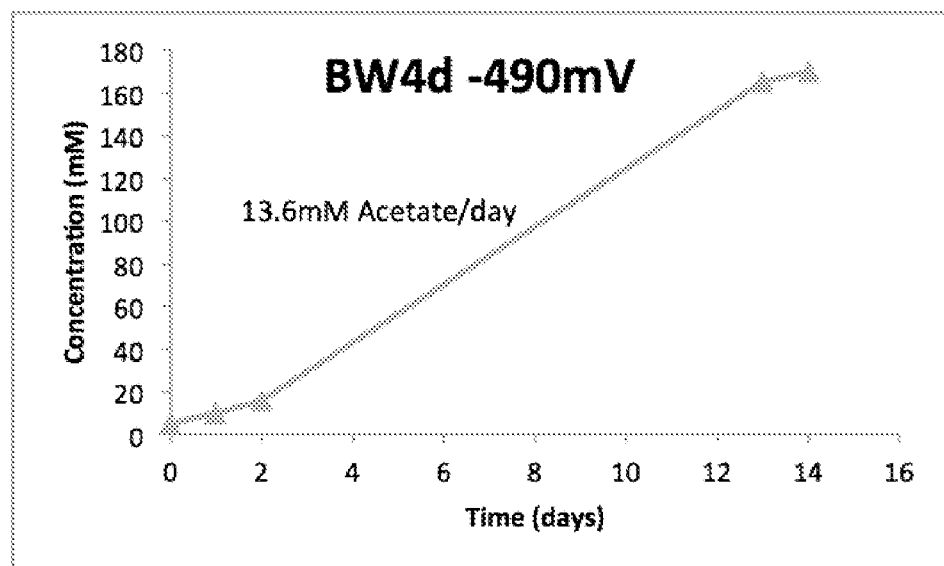
FIG. 5: Increased electroacetogenesis by the enriched brewery waste community when the biocathode was maintained at −490 mV vs. SHE and with a continuous supply of $CO_2$ sparged into the cathode liquid.

Rates were increased further following additional incubation, transfer and enrichment of the electrosynthetic communities when supplied with a continuous stream of $CO_2$ that was delivered at 10 to 50 ml/min directly into the cathode liquid. The pH remained stable under these conditions (between 6.5 and 6.8). $H_2$ production eventually rose to 95 mM day-1 (2.3 $m^3$ $m^{-3}$ cathode liquid volume per day). Acetate production rose to between 6 and 9 mM day-1 with accumulations above 100 mM in the cathode liquid (FIG. 4). All of this was done with the cathode potential poised at −590 mV. However, less voltage was applied to one cell by setting the potential higher at −490 mV. This cell then continuously produced acetate at 13.6 mM day-1 with an accumulation of 169 mM (FIG. 5). The coulombic efficiency into acetate was 64%.

Electrochemical Evaluation of the Biocatalyst

Figure 6:
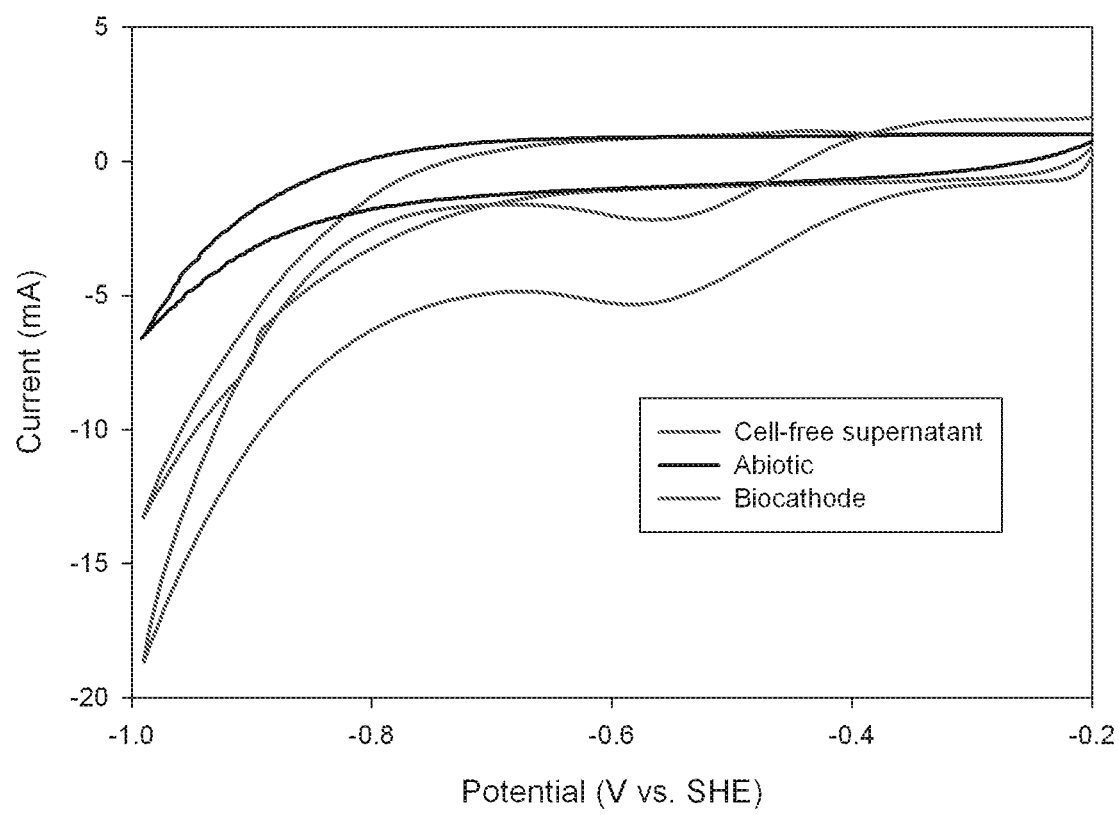
FIG. 6: Cyclic voltammetry (CV) on abiotic (upper two traces), cell-free supernatant (middle two traces), and biotic (lower two traces) BESs. Scan rate 1 mV/s.

Cyclic voltammetry (CV) was performed on the BESs in order to discern possible redox active components associated with the biocathodes. No redox peaks were detected in the abiotic (uninoculated) reactors, indicating a lack of electron shuttles in the medium (FIG. 6, abiotic line). Current production in the abiotic scan was very low at −590 mV and consistent with the low rate of proton reduction observed at this potential over an extended time period (FIG. B,D). The CV scan of the abiotic reactor stood in sharp contrast with the catalytic wave seen in the three replicate BESs with live biocathodes producing methane, acetate, and hydrogen (FIG. 4, vertical line). The onset of catalytic current during the reductive scan of a biocathode was at −340 mV and plateaued at −640 mV vs. SHE. The midpoint potential of the catalytic wave was −460 mV, which only varied slightly (approximately +/−30 mV) between replicates. The current draw at the peak of the catalytic wave was ~5 mA. In order for the non-catalyzed abiotic BES to reach the same current output, a potential of −900 mV or less was required. The over 300 mV discrepancy between peak current in the biotic scan strongly supports microbial catalysis of electrode oxidation.

When supernatant (spent media) from the replicate BESs were filtered and inserted into an abiotic reactor, no redox active peaks were observed (FIG. 6, middle two traces (as the traces proceed from the x-axis)). Since no redox active components were observed in the fresh medium or in the filtered supernatant, it is unlikely that a soluble mediator was responsible for electron transfer from the electrode to the microorganisms at −590 mV.

Electrosynthetic Microbial Community Composition

Figure 7:
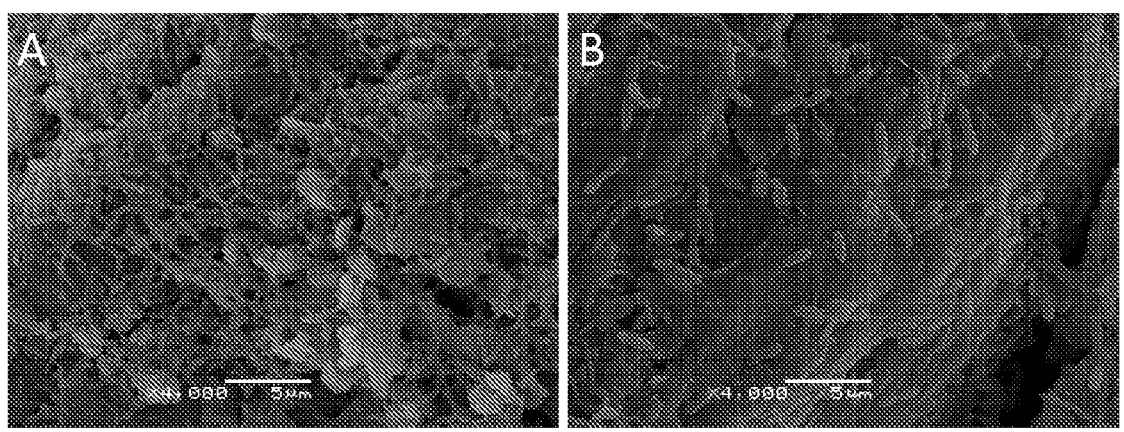
FIG. 7: Scanning electron micrographs of electrosynthetic cathode biofilms when (A) primarily methanogenic after 148 days (electrode from the same reactor shown in FIG. 1) and (B) acetogenic after treatment with 2-bromoethane sulfonic acid (day 56, electrode from the same reactor shown in FIG. 3c).

A scanning electron microscope (SEM) was used to visualize the prevalence of microorganisms attached to the electrode. Biofilm formation was seen on the graphite granule cathodes from untreated BESs producing acetate and methane (FIG. 7A). The dominant morphology was mostly of rod shaped microbes varying in size from 2 μm to 5 μm long. Another, thicker rod shaped organism was also observed. These thicker rods were approximately 1 μm long and less prevalent. However, when the biocathode was treated with 2-bromoethanesulfonic acid, these thicker rod shaped microbes were the dominant morphology on the electrode (FIG. 7B). The observation of these microorganisms on the cathode is consistent with the evidence from the CV, which is supportive of microbial catalyst acting at the surface of the electrode.

Figure 8:
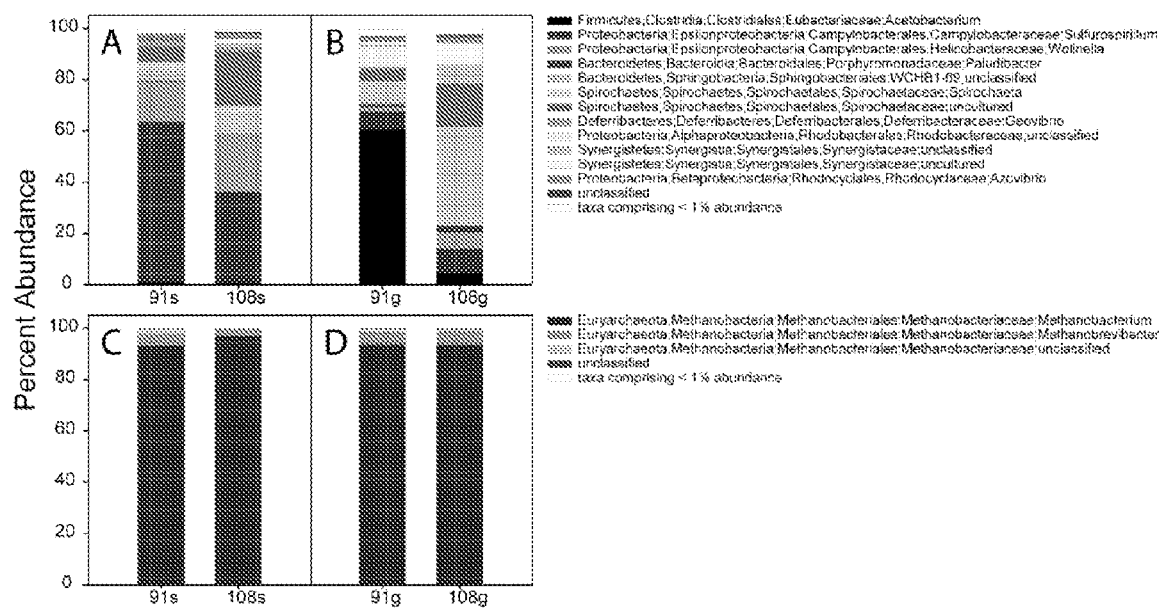
FIG. 8: Percent abundance of 16S rRNA for Bacteria (A and B) and Archaea (C and D) from supernatant (s) and graphite cathode (g) of the active microbial community on days 91 and 108 (FIG. 1A).

To assess the composition of the active microbial population within the electrosynthetic community, total RNA was extracted from samples taken from supernatant or graphite electrode granules at day 91 when acetogenesis was predominant and day 108 when methanogenesis was predominant as shown in FIG. 1A, and the phylogenetic data are presented in FIG. 8 and Tables 2-3. Overall, in the culture supernatant, the predominant bacterial phyla were Bacteriodetes, Deferribacteres, Firmicutes Proteobacteria, Spirochaetes, and Synergistetes. At day 91, when acetogenesis was the predominant activity, members of the *Sulfurospirillum* genus accounted for 62.3% of the bacterial reads sequenced in the supernatant with another 15.9% belonging to the genus *Wolinella*. A modest change occurred on day 108, when methanogenesis was the predominant activity, with *Sulfurospirillum* spp. remaining as the most abundant but decreasing to 36.0%. Members of the genus *Wolinella* increased to 22.8% and members of the family Spriochaetaceae increased from 9.5 to 24.2%.

A more dramatic change in the active bacterial population was observed with the samples extracted off of the graphite granule electrodes. *Acetobacterium* spp. were relatively minor members of the supernatant community, but when acetate was the major product (day 91) the percent of *Acetobacterium* on the electrode rose to 60.3%. When methane again dominated and acetate production was low (day 108) the *Acetobacterium* spp. decreased to 4.7%. An unclassified family (WCHB1-69) from the Sphingobacteriales represented 8.0% of the active population on the electrode at day 91 but became the dominant bacteria at day 108 (37.7%). In contrast, the abundance of WCHB1-69 was relatively constant at approximately 4-7% in the supernatant at days 91 and 108. Also found on the cathode on day 91 were members of the family Rhodobacteraceae (8.0%) and the genus *Sulfurospirillum* (7.4%). Additionally on day 108, rRNA of the Synergistaceae family (11.1%), and Spirochaetaceae family (17.4%) were detected on the cathode.

The predominant archaeal sequences were from the genus *Methanobacterium*, constituting >93% of the total sequenced archaeal reads, regardless of whether the supernatant or electrodes were examined or when the samples were taken. It is important to note that while acetogenesis was predominant at day 91, methanogenesis was also occurring at both day 91 and 108 time points. *Methanobrevibacter* represented ~5% of the reads and unclassified sequences made up a low percentage of total archaeal reads (<1%).

TABLE 2

Analysis of bacterial content of microbial populations.

| Genus | 91s | 108s | 91g | 108g |
|---|---|---|---|---|
| Firmicutes; Clostridia; Clostridiales; Eubacteriaceae; *Acetobacterium* | 1.0 | 0.2 | 60.3 | 4.7 |
| Proteobacteria; Epsilonproteobacteria; Campylobacterales; Campylobacteraceae; *Sulfurospirillum* | 62.3 | 36.0 | 7.4 | 9.5 |
| Proteobacteria; Epsilonproteobacteria; Campylobacterales; Helicobacteraceae; *Wolinella* | 15.9 | 22.8 | 1.6 | 6.4 |
| Bacteroidetes; Bacteroidia; Bacteroidales; Porphyromonadaceae; *Paludibacter* | 0.3 | 0.1 | 1.3 | 2.4 |
| Bacteroidetes; Sphingobacteria; Sphingobacteriales; WCHB1-69; unclassified | 3.8 | 7.4 | 8.0 | 37.7 |
| Spirochaetes; Spirochaetes; Spirochaetales; Spirochaetaceae; *Spirochaeta* | 3.3 | 3.6 | 1.0 | 1.0 |
| Spirochaetes; Spirochaetes; Spirochaetales; Spirochaetaceae; uncultured | 6.2 | 20.6 | 4.2 | 16.4 |
| Deferribacteres; Deferribacteres; Deferribacterales; Deferribacteraceae; *Geovibrio* | 2.5 | 1.7 | 1.3 | 0.5 |
| Proteobacteria; Alphaproteobacteria; Rhodobacterales; Rhodobacteraceae; unclassified | 0.2 | 0.1 | 8.0 | 0.7 |
| Synergistetes; Synergistia; Synergistales; Synergistaceae; unclassified | 0.0 | 1.5 | 0.7 | 6.5 |
| Synergistetes; Synergistia; Synergistales; Synergistaceae; uncultured | 0.0 | 1.9 | 1.1 | 8.6 |
| Proteobacteria; Betaproteobacteria; Rhodocyclales; Rhodocyclaceae; *Azovibrio* | 2.2 | 2.2 | 1.9 | 2.5 |
| unclassified; unclassified; unclassified; unclassified; unclassified | 0.1 | 0.2 | 0.3 | 0.6 |
| taxa comprising <1% abundance | 1.9 | 1.2 | 2.6 | 2.5 |
| taxa comprising <1% abundance | | | | |
| Actinobacteria; Actinobacteria; Actinomycetales; Corynebacteriaceae; *Corynebacterium* | 0.008112 | 0 | 0 | 0 |
| Actinobacteria; Actinobacteria; Actinomycetales; Nocardioidaceae; *Nocardioides* | 0.008112 | 0 | 0 | 0 |
| Actinobacteria; Actinobacteria; Actinomycetales; Propionibacteriaceae; *Micropruina* | 0 | 0 | 0.006081 | 0 |
| Actinobacteria; Actinobacteria; Actinomycetales; Propionibacteriaceae; *Propionibacterium* | 0.024337 | 0 | 0 | 0 |
| Actinobacteria; Actinobacteria; Actinomycetales; Propionibacteriaceae; unclassified | 0.008112 | 0 | 0 | 0 |
| Bacteroidetes; Bacteroidia; Bacteroidales; Porphyromonadaceae; *Petrimonas* | 0.032449 | 0.041719 | 0.018242 | 0 |
| Bacteroidetes; Bacteroidia; Bacteroidales; Porphyromonadaceae; *Proteiniphilum* | 0.032449 | 0.187735 | 0.030403 | 0.064842 |
| Bacteroidetes; Bacteroidia; Bacteroidales; Porphyromonadaceae; unclassified | 0.186582 | 0.020859 | 0.389152 | 0.006484 |
| Bacteroidetes; Bacteroidia; Bacteroidales; Rikenellaceae; vadinBC27 | 0.016225 | 0.006953 | 0.024322 | 0.025937 |
| Bacteroidetes; Bacteroidia; Bacteroidales; unclassified; unclassified | 0.064898 | 0.020859 | 0.054725 | 0 |
| Bacteroidetes; Sphingobacteria; Sphingobacteriales; KD1-131; unclassified | 0 | 0 | 0.012161 | 0 |
| Bacteroidetes; Sphingobacteria; Sphingobacteriales; unclassified; unclassified | 0.146021 | 0.062578 | 0.662775 | 0.181559 |
| Bacteroidetes; unclassified; unclassified; unclassified; unclassified | 0.040561 | 0.013906 | 0.200657 | 0.012968 |
| Chlorobi; Chlorobia; Chlorobiales; BSV26; unclassified | 0 | 0.006953 | 0 | 0 |
| Deferribacteres; Deferribacteres; Deferribacterales; Deferribacteraceae; *Denitrovibrio* | 0.210919 | 0.542345 | 0.188496 | 0.538192 |
| Deferribacteres; Deferribacteres; Deferribacterales; Deferribacteraceae; unclassified | 0.016225 | 0 | 0 | 0.025937 |
| Deferribacteres; unclassified; unclassified; unclassified; unclassified | 0 | 0.006953 | 0 | 0 |
| Firmicutes; Bacilli; Bacillales; Staphylococcaceae; *Staphylococcus* | 0 | 0.013906 | 0 | 0 |
| Firmicutes; Bacilli; Lactobacillales; Streptococcaceae; *Streptococcus* | 0 | 0 | 0 | 0 |
| Firmicutes; Clostridia; Clostridiales; Eubacteriaceae; unclassified | 0.097347 | 0.006953 | 0.024322 | 0 |
| Firmicutes; Clostridia; Clostridiales; Family_XI_Incertae_Sedis; *Sedimentibacter* | 0.129796 | 0.076484 | 0.127691 | 0 |
| Firmicutes; Clostridia; Clostridiales; Family_XIII_Incertae_Sedis; *Anaerovorax* | 0.016225 | 0 | 0 | 0 |
| Firmicutes; Clostridia; Clostridiales; Family_XIII_Incertae_Sedis; unclassified | 0.040561 | 0 | 0.036483 | 0 |
| Firmicutes; Clostridia; Clostridiales; Lachnospiraceae; unclassified | 0.032449 | 0 | 0.012161 | 0 |
| Firmicutes; Clostridia; Clostridiales; Lachnospiraceae; uncultured | 0.373165 | 0.006953 | 0.273623 | 0.071327 |
| Firmicutes; Clostridia; Clostridiales; Peptococcaceae; *Dehalobacter* | 0 | 0 | 0 | 0.006484 |
| Firmicutes; Clostridia; Clostridiales; Peptostreptococcaceae; Incertae_Sedis | 0 | 0 | 0.006081 | 0 |
| Firmicutes; Clostridia; Clostridiales; Ruminococcaceae; unclassified | 0.064898 | 0.048672 | 0.036483 | 0.006484 |
| Firmicutes; Clostridia; Clostridiales; Syntrophomonadaceae; *Syntrophomonas* | 0.024337 | 0 | 0 | 0 |
| Firmicutes; Clostridia; Clostridiales; unclassified; unclassified | 0.308266 | 0.006953 | 0.048644 | 0 |

TABLE 2-continued

Analysis of bacterial content of microbial populations.

| Genus | 91s | 108s | 91g | 108g |
|---|---|---|---|---|
| Firmicutes; Clostridia; Clostridiales; Veillonellaceae; *Acidaminococcus* | 0 | 0 | 0.006081 | 0 |
| Firmicutes; Clostridia; Clostridiales; Veillonellaceae; unclassified | 0.008112 | 0 | 0.006081 | 0.006484 |
| Firmicutes; Clostridia; unclassified; unclassified; unclassified | 0.008112 | 0 | 0 | 0 |
| Firmicutes; unclassified; unclassified; unclassified; unclassified | 0.07301 | 0.006953 | 0.139852 | 0.019453 |
| Proteobacteria; Alphaproteobacteria; Rhizobiales; Hyphomicrobiaceae; unclassified | 0.016225 | 0 | 0 | 0 |
| Proteobacteria; Alphaproteobacteria; Rhizobiales; Hyphomicrobiaceae; *Xanthobacter* | 0.056786 | 0.013906 | 0 | 0 |
| Proteobacteria; Alphaproteobacteria; Rhizobiales; Rhizobiaceae; *Rhizobium* | 0.008112 | 0 | 0 | 0 |
| Proteobacteria; Alphaproteobacteria; Rhizobiales; Rhodobiaceae; *Parvibaculum* | 0 | 0.006953 | 0 | 0 |
| Proteobacteria; Alphaproteobacteria; Rhizobiales; unclassified; unclassified | 0.016225 | 0 | 0 | 0 |
| Proteobacteria; Alphaproteobacteria; Rhodobacterales; Rhodobacteraceae; *Haematobacter* | 0.162245 | 0.013906 | 0.018242 | 0 |
| Proteobacteria; Alphaproteobacteria; Rhodospirillales; Rhodospirillaceae; *Telmatospirillum* | 0 | 0.013906 | 0 | 0 |
| Proteobacteria; Alphaproteobacteria; Sphingomonadales; unclassified; unclassified | 0 | 0 | 0.006081 | 0 |
| Proteobacteria; Alphaproteobacteria; unclassified; unclassified; unclassified | 0.016225 | 0.006953 | 0 | 0 |
| Proteobacteria; Betaproteobacteria; Burkholderiales; Alcaligenaceae; *Achromobacter* | 0.008112 | 0 | 0 | 0.006484 |
| Proteobacteria; Betaproteobacteria; Burkholderiales; Comamonadaceae; *Alicycliphilus* | 0.032449 | 0.006953 | 0.006081 | 0 |
| Proteobacteria; Betaproteobacteria; Burkholderiales; Comamonadaceae; *Aquabacterium* | 0 | 0 | 0.006081 | 0 |
| Proteobacteria; Betaproteobacteria; Burkholderiales; Comamonadaceae; *Diaphorobacter* | 0 | 0.006953 | 0.006081 | 0 |
| Proteobacteria; Betaproteobacteria; Rhodocyclales; Rhodocyclaceae; *Azospira* | 0 | 0 | 0 | 0.006484 |
| Proteobacteria; Betaproteobacteria; unclassified; unclassified; unclassified | 0.008112 | 0 | 0 | 0 |
| Proteobacteria; Deltaproteobacteria; Desulfovibrionales; Desulfovibrionaceae; unclassified | 0 | 0 | 0.006081 | 0.006484 |
| Proteobacteria; Deltaproteobacteria; Desulfovibrionales; unclassified; unclassified | 0 | 0 | 0.006081 | 0.006484 |
| Proteobacteria; Deltaproteobacteria; Desulfuromonadales; Geobacteraceae; *Geobacter* | 0.146021 | 0.410235 | 0 | 0.006484 |
| Proteobacteria; Deltaproteobacteria; Desulfuromonadales; Geobacteraceae; unclassified | 0.008112 | 0.027813 | 0 | 0 |
| Proteobacteria; Deltaproteobacteria; Desulfuromonadales; unclassified; unclassified | 0.032449 | 0.048672 | 0 | 0 |
| Proteobacteria; Epsilonproteobacteria; Campylobacterales; Campylobacteraceae; *Arcobacter* | 0.07301 | 0.13211 | 0.012161 | 0 |
| Proteobacteria; Epsilonproteobacteria; Campylobacterales; Campylobacteraceae; unclassified | 0.008112 | 0.027813 | 0 | 0.012968 |
| Proteobacteria; Epsilonproteobacteria; Campylobacterales; Helicobacteraceae; unclassified | 0 | 0 | 0 | 0.006484 |
| Proteobacteria; Epsilonproteobacteria; Campylobacterales; unclassified; unclassified | 0.008112 | 0.034766 | 0 | 0.019453 |
| Proteobacteria; Epsilonproteobacteria; unclassified; unclassified; unclassified | 0 | 0 | 0 | 0.006484 |
| Proteobacteria; Gammaproteobacteria; Pseudomonadales; Moraxellaceae; *Acinetobacter* | 0.008112 | 0 | 0 | 0 |
| Proteobacteria; unclassified; unclassified; unclassified; unclassified | 0.040561 | 0.013906 | 0.006081 | 0.006484 |
| Spirochaetes; Spirochaetes; Spirochaetales; Spirochaetaceae; unclassified | 0.008112 | 0.034766 | 0.048644 | 0.084295 |
| Spirochaetes; Spirochaetes; unclassified; unclassified; unclassified | 0 | 0 | 0 | 0.006484 |
| Synergistetes; Synergistia; Synergistales; Synergistaceae; *Aminiphilus* | 0 | 0 | 0.036483 | 0.012968 |

TABLE 3

Analysis of archaeal content of microbial populations.

| Genus | 91s | 108s | 91g | 108g |
|---|---|---|---|---|
| Euryarchaeota; Methanobacteria; Methanobacteriales; Methanobacteriaceae; *Methanobacterium* | 93.3 | 96.9 | 93.6 | 93.5 |
| Euryarchaeota; Methanobacteria; Methanobacteriales; Methanobacteriaceae; *Methanobrevibacter* | 4.7 | 2.3 | 4.7 | 5.1 |
| Euryarchaeota; Methanobacteria; Methanobacteriales; Methanobacteriaceae; unclassified | 1.7 | 0.4 | 1.5 | 0.9 |
| unclassified; unclassified; unclassified; unclassified; unclassified | 0.0 | 0.0 | 0.0 | 0.1 |
| taxa comprising <1% abundance | 0.0 | 0.2 | 0.2 | 0.3 |
| taxa comprising <1% abundance | | | | |
| Euryarchaeota; Methanobacteria; Methanobacteriales; unclassified; unclassified | 0.051787 | 0.148706 | 0.131993 | 0.074528 |
| Euryarchaeota; Methanomicrobia; Methanomicrobiales; Methanospirillaceae; *Methanospirillum* | 0.004708 | 0 | 0 | 0 |
| Euryarchaeota; Thermoplasmata; Thermoplasmatales; Terrestrial_Miscellaneous_Gp; unclassified | 0.009416 | 0.004957 | 0 | 0 |
| Euryarchaeota; unclassified; unclassified; unclassified; unclassified | 0.174191 | 0.213146 | 0.238603 | 0.26617 |

Continuous Culture, Alternate Electrode Material, and Additional Products

Figure 9:
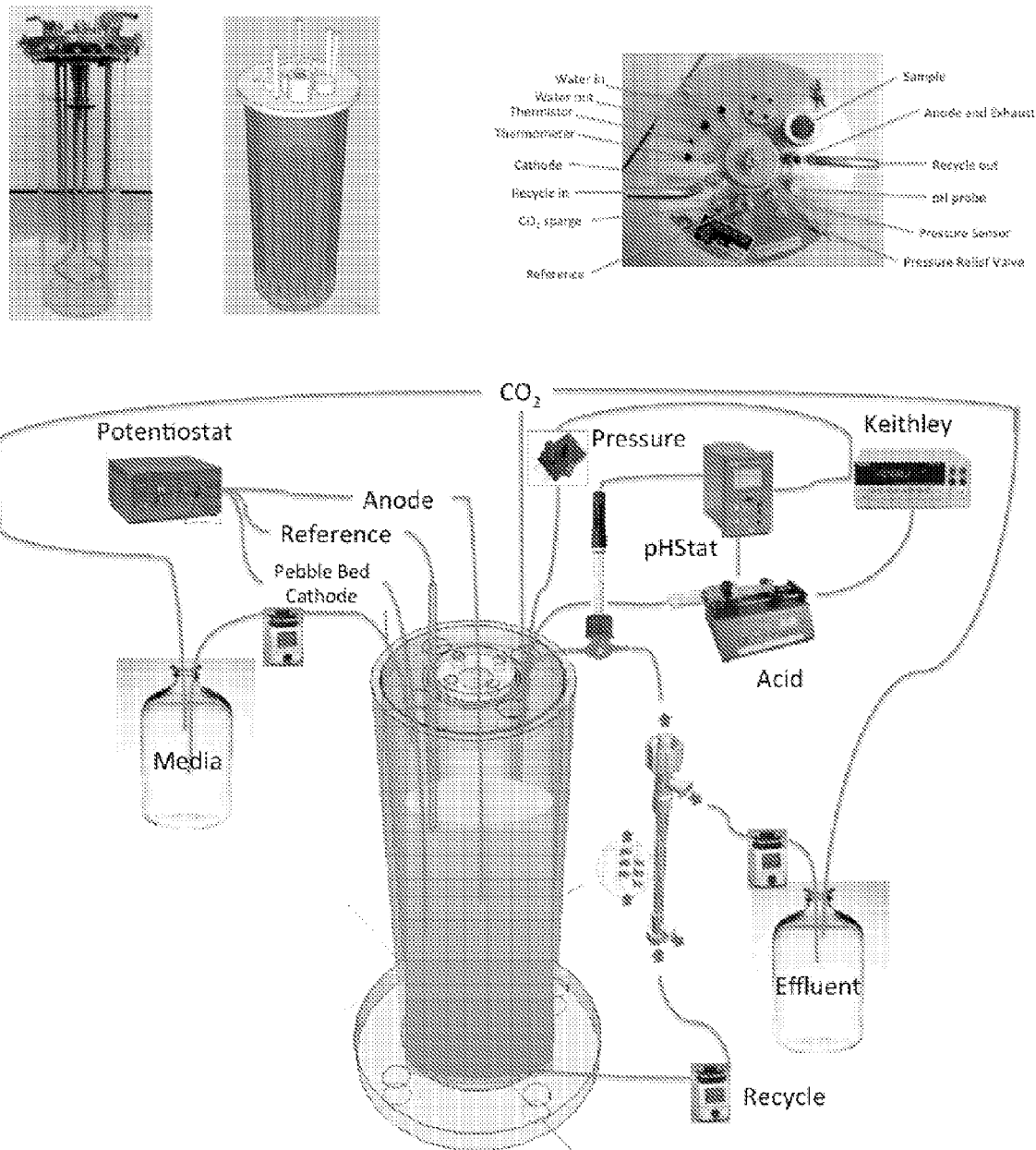
FIG. 9: Additional examples of continuous flow electrosynthesis reactor systems.

The electrosynthetic community has successfully been maintained in a continuous flow system (continuous liquid and gas, $CO_2$, passage through the electrochemical cell). The cell shown in FIG. 14 was used for the batch systems described above and was modified here for continuous flow operation. In addition, further scalable iterations of this system have been envisioned by the inventors (FIG. 9). These systems have been tested with graphite granule cathodes inoculated with the electrosynthetic microbial community and with steel bead electrodes inoculated with the same microbiome.

Figure 10:
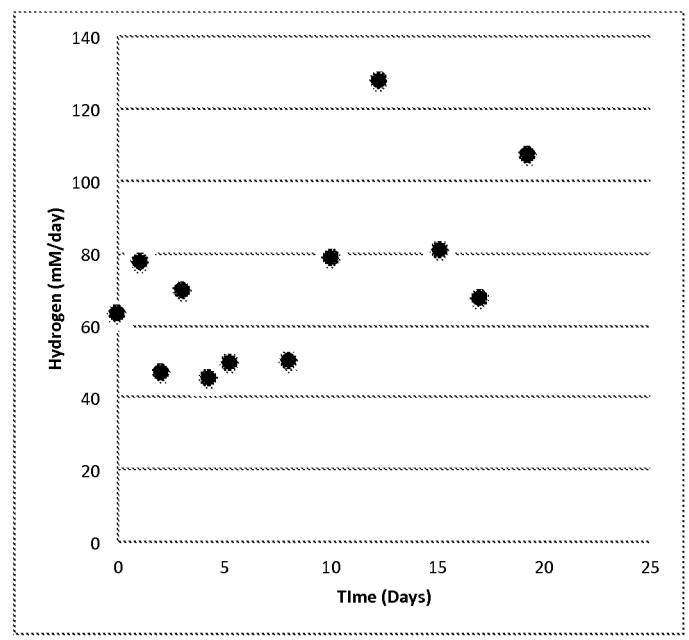
FIG. 10: Abiotic production of $H_2$ with steel cathode poised at −590 mV.
Figure 11:
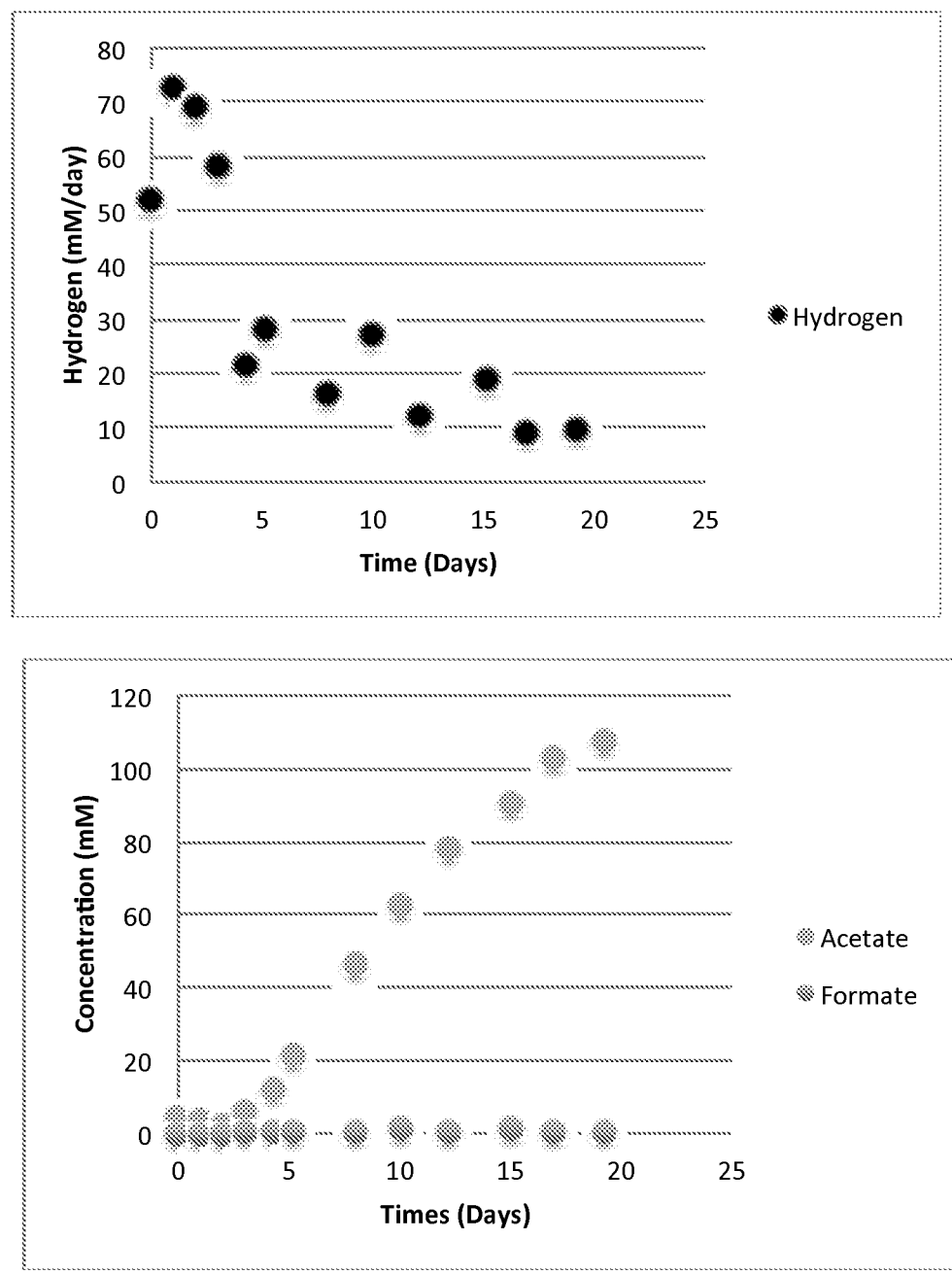
FIG. 11: Production and consumption of $H_2$ in steel biocathode poised at −590 mV vs. SHE with electrosynthetic microbiome (top). Production of acetate by same system (bottom).
Figure 12:
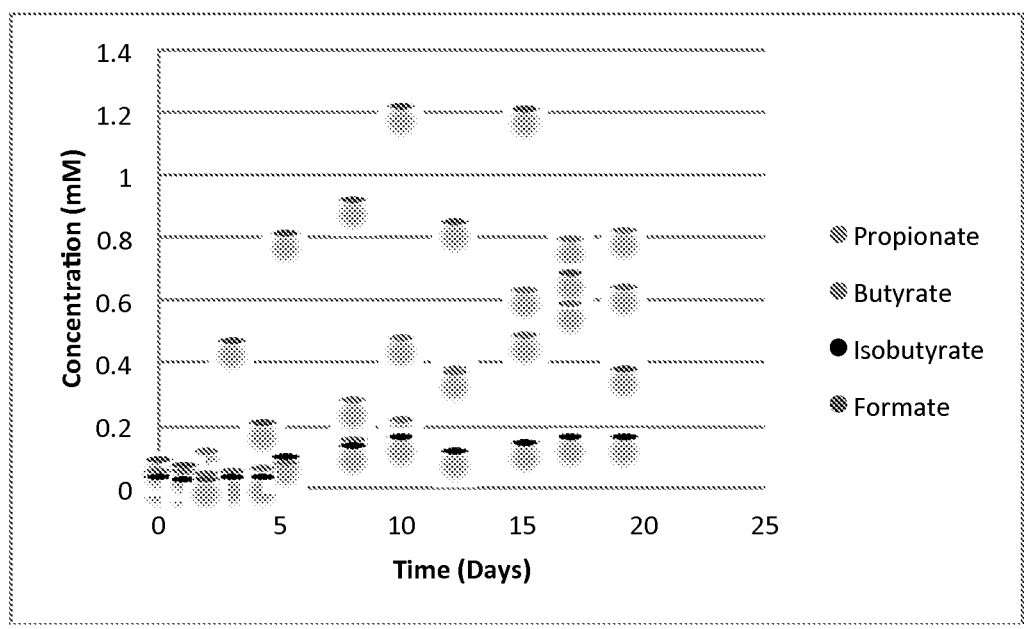
FIG. 12: Production of other products by system described in FIG. 13.

Abiotic $H_2$ production with the steel cathode under continuous flow (FIG. 10) reached approximately 100 mM day$^{-1}$ (per cathode liquid volume). When inoculated with the electrosynthetic microbial community the steel biocathode consumed such hydrogen and produced acetate at a rate (9.5 mM day$^{-1}$) similar to that observed with graphite granule electrodes (FIG. 11). The community also generates additional products, but thus far production appears to be more so with the steel biocathode (FIG. 12).

Figure 13:
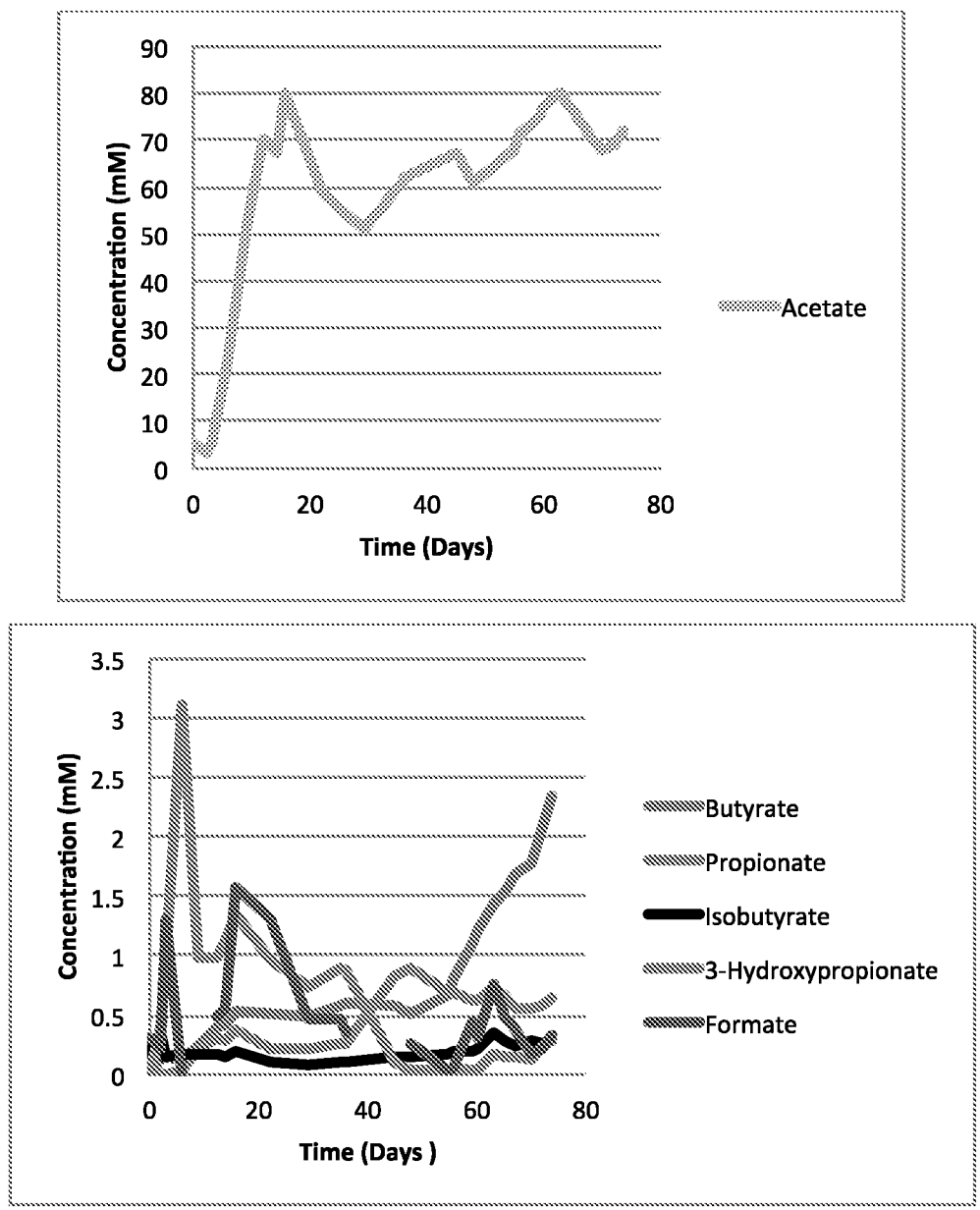
FIG. 13: Production of acetate (top) and other products (bottom) by the electrosynthetic microbiome in a continuous flow system with steel biocathode poised at −590 mV vs. SHE.

Addition of Other Microbial Catalysts to the Electrosynthetic Microbial Community The electrosynthetic microbiome described herein will produce significant amounts of $H_2$, acetate and other products, which may then be used by other microbial catalysts to produce additional value-added products, or to produce even more acetate. Possibilities are the addition of *Ralstonia* species that have been engineered to produce isobutanol and butanol from $H_2$ and $CO_2$. The addition of *Clostridium carboxidivorans* P7, which is known to produce acetate and alcohols from syngas (mixture of $H_2$, CO and $CO_2$), was also tested in the instant electrosynthetic community. Incubating this combination of microorganisms in a steel biocathode poised at −590 mV under continuous flow (liquid medium and $CO_2$) with an effluent recycle through a hollow fiber membrane to maintain biocatalyst in the cathode has resulted in the continuous production of 5 to 8 mM acetate per day for over two months (FIG. 13). In addition, this combination of cells also produced 3-hydroxypropionate and butyrate (FIG. 13).

Discussion

An autotrophic microbial community from brewery wastewater was selected on a cathode of a bioelectrochemical system for the production of valuable commodity chemicals. Methane, acetate and hydrogen were all sustainably and reproducibly generated electrosynthetically at a cathode potential of −590 mV vs. SHE. Each of these products has been generated with microbial biocathodes, but this is the first study to demonstrate their simultaneous production at rates higher than those reported in the literature. Furthermore, it is the first report of the electrosynthesis of acetate from $CO_2$ by a mixed microbial community. Differences in laboratory approaches can complicate the comparison of production rates, but sustained rates of methanogenesis and acetogenesis based on cathode volume surpassed what has thus far been discovered for electrosynthesis of these compounds at potentials higher than −700 mV (Table 4).

TABLE 4

Rates of electrosynthesis with graphite or carbon cloth electrodes.

| Products | Cathode Potential (mV vs. SHE) | Maximum Rates * (mM day$^{-1}$) | Microbial Source |
| --- | --- | --- | --- |
| Hydrogen | −700 | 25.3 (3.2 abiotic) | Wastewater (Rozendal et al. 2008) |
| Hydrogen | −900 | 8.0 (1.5 abiotic) | Desulfovibrio paquesii (Aulenta et al. 2012) |
| Hydrogen | −590 | 11.8 (0.045 abiotic) | Brewery wastewater, (studies herein) |
| Hydrogen | −590 | 95 (0.045 abiotic) | Brewery wastewater, (studies herein) |
| Hydrogen | −590 with steel biocathode | 300 (100 abiotic) | Brewery wastewater, (studies herein) |
| Methane | −800 | 1.6 | Wastewater (Cheng et al. 2009) |
| Methane | −800 | 0.4 | Wastewater (Villano et al. 2012) |
| | −900 | 2.1 | |
| Methane | −439 | 0.73 | Baltimore Harbor Sediment (Pisciotta et al. 2012) |
| | −539 | 0.54 | |
| Methane | −590 | 7.0 | Brewery wastewater, (studies herein) |
| Acetate | −400 | 0.17 | Sporomusa ovata (Nevin et al. 2010) |
| Acetate | −490 | 13.6 | Brewery wastewater, (studies herein) |
| Acetate | −590 | 9.0 | Brewery wastewater, (studies herein) |
| Acetate | −590 with steel biocathode | 9.6 | Brewery wastewater, (studies herein) |

* Sill high rates of synthesis are detailed in the studies of Examples 3-4. For example, at −590 mV vs. SHE)up to 1298 mM/day $H_2$ and 17 mM acetate per day.

A distinguishing feature of the biocathodes examined herein was the electrochemical evidence for direct electrode oxidation by the mixed microbial community. Hydrogen production facilitated by the microorganisms may shuttle electrons to the methanogenic and acetogenic microorganisms, but several pieces of evidence indicate that direct electron transfer is also participating: the expression of a catalytic wave observed by CV with an onset at −340 mV and midpoint potential at −460 mV, the lack of similar peaks with sterile or spent media, biofilm formation on the electrode, delayed exponential production of hydrogen, and the recovery of electrons in all three products that exceeds the abiotic generation of hydrogen by several hundred fold.

Electrosynthesis of Methane

Sustainable rates of methane production above 1.5 mM day$^{-1}$ were achieved and reached 7 mM day$^{-1}$. Both of these volumetric rates are as high as or greater than any reported in the literature with cathodes poised at potentials above −800 mV (Table 4). Pisciotta et al. recently reported methanogenesis (0.73 mM day$^{-1}$) at −439 mV that unexpectedly decreased as the potential was lowered to −539 mV, which led the authors to discuss the possibility of organic substrates contributing to the initial rates observed at −439 mV (Pisciotta et al. 2012). Cheng et al. and Villano et al. both demonstrated that lower potentials (−799 mV) would support higher methane productivity (Cheng et al. 2009; Villano et al. 2010). However, even with increased inputs of energy the volumetric rates were less than reported here with a cathode potential of −590 mV. There could be numerous reasons for the higher rates observed with the brewery waste electrosynthetic community including the source of microorganisms, the selection and adaptation of microbes at the chosen cathode potential, and the design and material of the electrode (graphite granules in this case). Regardless, the results of this study clearly indicate that on a working volume basis the rates of methanogenesis far surpass abiotic hydrogen production. Furthermore, this study proves that elevated rates of sustainable methane production may be achieved at potentials above −800 mV.

Electrosynthesis of Acetate

Acetate production concomitant with methane and hydrogen production in the initial BES reached 1.02 mM day$^{-1}$; a rate that is higher than what has been reported for electroacetogenesis. The first report of electroacetogenesis used pure cultures of Sporomusa ovata to produce 1 mmol of acetate over 6 days (0.17 mM day$^{-1}$) and trace amounts of 2-oxobutyrate in a continuous flow reactor (Nevin et al. 2010). A second report by Nevin et al. demonstrated electroacetogenesis by several other pure culture acetogens, but none matched the production rate of S. ovata (Nevin et al. 2011).

The rate of electroacetogenesis by the brewery waste community increased to 4 mM day$^{-1}$ after the addition of 2-bromoethanesulfonic acid, an inhibitor of the methyl reductase of methanogens (Gunsalus et al. 1978). This rate out paces reported rates for electroacetogenesis by S. ovata by more than 20-fold. However, Nevin et al. demonstrated electroacetogenesis in a continuous flow system (batch systems were examined in the present study) over 6 days with S. ovata at a cathode potential (−400 mV) substantially higher than what was used in the present study (Nevin et al. 2010). Based on the CV analysis of the brewery waste electrosynthetic community, the onset of the catalytic wave began at approximately −340 mV, indicating that rates of electroacetogenesis by the mixed community could be similar to that of S. ovata at the higher potentials. From a productivity standpoint however, maintenance of the mixed community at −590 mV supports a much higher rate of eletroacetogenesis.

In addition, as noted above in the results, further enrichment has led to even faster rates of acetate production, eventually 80-fold faster than what has been previously reported (Table 4). The acetate accumulates to 169 mM. More importantly, it is known that the ratio of membrane surface to electrode surface is limiting the operation of this cell, perhaps by 10 fold. A relatively simple engineering change of membrane to electrode surface area could boost rates further significantly and such experiments are planned.

Production of Hydrogen and Possible Mechanisms of Electron Transfer from the Cathode With enough driving force, a biocathode will produce hydrogen at rates that exceed abiotic production from an electrode (Table 4). Aulenta et al. observed 8.0 mM day$^{-1}$ hydrogen production by a graphite cathode poised at −900 mV and inoculated with *Desulfovibrio paquesii*, which was approximately 5-fold more than was produced in abiotic controls (Aulenta et al. 2012). Sustained activity and growth of the organism with the electrode was not determined. Rozendal et al. demonstrated that hydrogen could be produced with a mixed microbial community in a graphite cathode that was poised at −700 mV (Rozendal et al. 2008). Initially the biocathode produced only methane, presumably hydrogenotrophically due to abiotically produced hydrogen. Bicarbonate was removed from the medium to eliminate methanogenesis and this resulted in the production of up to 25.3 mM day$^{-1}$ hydrogen (8-fold greater than abiotic production) and no methane for 1000 h. The removal of bicarbonate from the medium was not possible for the present study since the goal was the sustained electrosynthesis of organic compounds from $CO_2$. Similar to what was observed by Rozendal et al., hydrogen did not accumulate during the initial stages of the development of the brewery wastewater community on a biocathode. Surprisingly however, sustainable and transferable rates of hydrogenesis that were nearly half that reported by Rozendal et al. (Table 4) eventually arose concomitant with the production of methane or acetate while the cathode was poised at −590 mV. Whereas the ratio of biotic to abiotic production ranged from 5 to 8 in the previous studies (Aulenta et al. 2012: Rozendal et al. 2008), here with the cathode poised at a higher potential the ratio increased to more than 250 with several hundred-fold more electron equivalents simultaneously recovered in methane or acetate. Recently the inventors have boosted the $H_2$ production rates even higher, where they exceed those reported by Rozendal et al. by 51.3× with graphite biocathodes and more than 10-fold with steel biocathodes (Table 4 and Examples 3-4).

It is possible that electrons are being directly delivered from the cathode to the microorganisms producing methane, acetate, and hydrogen. It is also plausible that hydrogen could be serving as the electron-carrying intermediate between the electrode and the methanogens and acetogens, but it is evident that such hydrogen must be produced biotically at the cathode. It is clear that the biology of the system is greatly facilitating the electrosynthetic process since the electron recovery in products is so high vs. what is recovered abiotically. The catalytic wave detected by CV (FIG. 4), combined with the observation of a biofilm on the cathode and the delayed production of hydrogen concomitant with methanogenesis and acetogenesis, is in agreement with the biological production of hydrogen being coupled to direct electron transfer from the electrode to a microbe. The onset of current draw began at −340 mV (FIG. 4), a cathode potential that was more than 300 mV higher than the onset of current draw in the abiotic reactors, indicating that the microorganisms catalyzed electron transfer from the electrode. Importantly, the plateau in current is a unique signature of microbial catalysis of electron transfer from the electrode because abiotic current draw would be continuous with decreasing potentials. If the catalytic wave is expressed by proton reducing bacteria then the constant supply of electrons from the cathode in a proton rich environment may enable these microbes to extract energy in the form of ATP while generating hydrogen. Although growth was not measured in this study, the evidence of a biofilm and sustained and transferable activity suggests that growth did occur. It is conceivable that a syntrophic relationship between electrode-oxidizing proton reducers and acetogens and methanogens may help support the growth of the entire community and result in faster production rates of all three products. Interestingly though, methane and acetate continue to be produced at fast rates even as hydrogen accumulation increases, indicating that hydrogen does not shutdown proton reduction under these conditions. This is in agreement with what Aulenta et al. observed with *D. paquesii* producing hydrogen in an electrochemical cell (Aulenta et al. 2012). Therefore, either the methanogens and acetogens are unable to keep up with the microbes responsible for hydrogen generation, or perhaps they do not use the free hydrogen and directly receive electrons from the electrode, possibly by direct electron transfer between species (Summers et al. 2010), or through an electron-carrying mediator other than $H_2$. However, the lack of any redox peaks in the CV scan of the spent medium would suggest that the medium or the microbial community does not supply a soluble mediator other than hydrogen.

The Electrosynthetic Microbial Community

Microbial communities are notorious for the intricate interactions between microorganisms that frequently result in an efficient and productive process. This is due to the natural selection of microorganisms that will operate in stable consortia. Often it is desirable to select for such consortia to perform useful reactions, e.g. the synthesis of commodity chemicals, particularly when the growth and survival of the microbial community is dependent on those reactions. Extended incubation in a BES with a poised potential and only $CO_2$ as the carbon source served as the selection process for this study. When a potential of −590 mV was applied the result was a community that would electrosynthesize three commodity chemicals: methane, acetate and hydrogen. A diverse group of active microorganisms were detected on the cathodes with the bacterial community shifting concomitantly with changes in prevailing functional activity (acetogenesis, methanogenesis, hydrogenesis).

The data indicate that at least one member of the community will interact directly with the electrode. *Acetobacterium* spp. were the most prevalent and active Bacteria on the electrode when acetate was produced. Previous attempts to electrosynthesize acetate with *Acetobacterium woodii* failed, although it consumed $H_2$ supplied to the cathode chamber (Nevin et al. 2011). The *Acetobacterium* spp. detected here were strongly associated with the electrode and dominated that population (60.3%). Either these *Acetobacterium* spp. are quite different from *A. woodii* or the microbial community on the electrode affords *Acetobacterium* with advantages unrecognized in the pure culture. The Sphingobacteriales that became dominant as the community progressed have close sequence identities to microorganisms found in electrode reducing biofilms and to hydrogen producing communities. It is possible that microorganisms such as the Sphingobacteriales WCHB1 or *Sulfurospirillum* are oxidizing the electrode and generating hydrogen (similar to *D. paquesii*) that feeds the methanogens and acetogens, however this could not be proven at this time. Hydrogenotrophic methanogens, *Methanobacterium* in particular (93%), dominated the Archaea detected on the electrode regardless of conditions, and the dominant microbial morphology observed on the electrode when methanogenic was a rod with the appearance of *Methanobacterium*. Cheng et al. (Cheng et al. 2009) reported a similar percentage of *Methanobacterium* in an electromethanogenic cathode. All three dominant members of the varying community discussed above could potentially be responsible for electrode oxidation.

Implications for Commodity Chemical Production

Methane is the primary component of natural gas (NG), which is widely used in automobiles and electricity generation (Balash et al. 2008; Energy USDo. 2010). It is also the primary source of hydrogen for the production of nitrogen fertilizers (Abram et al. 2005). No biofuel, including electrofuels at this time, could compete economically with the present low price of NG unless subsidized, but the cost of NG will rise as its use increases. In addition, even though a 100 year supply of NG has been estimated (Hackett J T ea 2011) it will eventually be consumed. Although it is by far the cleanest of the fossil fuels, its use still results in the release of climate-changing $CO_2$. Furthermore, the hydraulic fracturing process needed to extract shale gas requires large amounts of water and risks groundwater contamination (Osborn et al. 2011). Electromethane from renewable and sustainable sources of energy will have many of the same benefits but none of these problems, and it could be developed first to supplement NG with the goal of one day replacing it. As this study helps demonstrate, the rates of electromethanogenesis can be improved. At 131 moles of methane per gallon of gasoline equivalent (GGE) (based on 114,000 Btu per gallon of gasoline, 1011 Btu per cu ft $CH_4$, and ideal gas law at 25° C.), the 7 mM day$^{-1}$ rate observed for electromethanogenesis would calculate to 0.05 GGE day$^{-1}$ m$^{-3}$ reactor. Although still requiring improvement, increasing this rate by an order of magnitude would conceivably produce 0.5 GGE each day from a reactor the size of a kitchen appliance. As this technology attracts more attention, rates may increase so that a renewable biogas technology to replace NG may be developed.

Acetic acid is another valuable commodity chemical made from fossil fuels that is used in industrial processes to produce vinyl acetate for paints and adhesives and to a smaller extent vinegar (Cheung et al. 2005). Production for human consumption, e.g. food and cosmetics, requires a higher degree of purity, which is achieved by microbial fermentation (Drake et al. 2008; Parrondo et al. 2003). Acetate is also a key intermediate in the production of biofuels, as it has been shown to be a feedstock for a microbial community to produce ethanol in BESs using methyl viologen as an electron carrier (Steinbusch et al. 2010). Any biosynthetic pathway that involves reducing $CO_2$ to multicarbon compounds must first pass through acetyl-coA and acetate can be readily converted to acetyl-coA by microbes. Hence, electroacetate could be used as a precursor for fuel production or for the production of high purity foods and cosmetics. In addition, a synthetic biology approach could be coupled with electroacetogenesis to produce commodity chemicals. A similar approach was taken by Li et al. with formic acid as a feedstock to make isobutanol (Li et al. 2012).

Hydrogen is used in many industrial processes (e.g. petroleum refining, food additives, fertilizers) and is ordinarily produced from fossil fuels (natural gas particularly). The energy of 1 kg of $H_2$ is approximately equivalent to that in 1 gallon of gasoline (1 GGE). At 2.3 m$^3$ m$^{-3}$ day$^{-1}$ a reactor the size of a large heat pump or refrigerator would produce approximately 0.2 kg of $H_2$ per day, or 0.2 GGE per day. At 2 cents/kWhr (a common industrial rate), a 5 m$^3$ biocathode supplied with 2 V would produce 1 kg/day $H_2$ for $1.68/kg $H_2$. While this would not be economically viable, this is approaching a useful production rate/cost and it is believed that a 10 fold increase (or more) in this rate is still possible.

Electrosynthesis potentially offers a revolutionary way of producing the chemicals needed to sustain modern culture. The carbon source for the process, $CO_2$, is plentiful and inexpensive, the electrons may be supplied from sustainable non-carbon based sources, land mass requirements are negligible and will not compete with food crop production, and being strictly carbon neutral electrosynthesis presents an attractive way to combat climate change. Analogous to the field of microbial fuel cells where intensive research has led to a better understanding of the process and exponential gains in current generation (Logan B E 2009), here it has been demonstrated that the rates of production of multiple commodity chemicals by electrosynthesis can be further increased, thereby advancing the technology closer to becoming competitive with the fossil-carbon based industries.

Microbial Electrosynthesis of Bioplastics

Bioplastics are better than petroleum-based plastics because they avoid carbon dioxide emission and are less recalcitrant in the environment. Production of bioplastics has typically used wastewater streams or costly and defined sugar feedstocks. Other processes use genetically modified organisms or pure strains, which necessitate costly sterilization. The present invention contemplates the production of bioplastic without the above mentioned costs, and has the added benefit of fixing carbon dioxide without the marginal land use issues of sugar feedstocks, or the variability of wastewater streams. In addition, the process may be used to sequester carbon away from the atmosphere.

Figure 17:
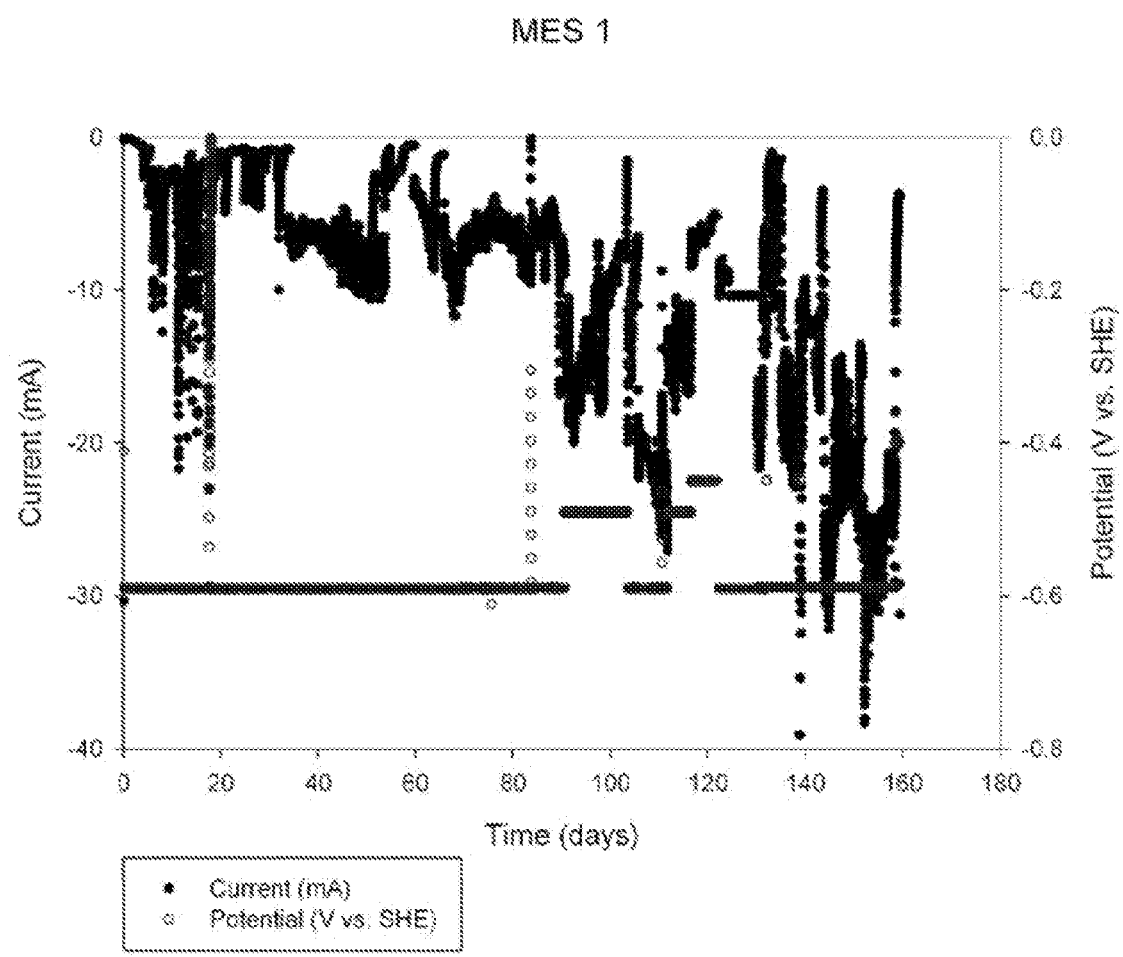
FIG. 17: Current (solid circles) and applied potential (open circles) over the time course of the experiment. Applied potential varied due to either deliberate short term experiments to test current draw at higher potentials or because of instrumentation overload at the counter electrode.

Plastic may be produced from renewable electricity and carbon dioxide as the sole carbon source by employing a microbiome and a polyhydroxyalkanote (PHA) producing organism(s) in a bioelectrochemical system. In some aspects, the methane, acetic acid, and/or hydrogen produced at a biocathode by the above disclosed methods, along with oxygen generated at an anode, can be fed to a second reactor which contains microorganisms that use these compounds to produce bioplastics (polyhydroxalkonoates) (FIG. 17).

The biocathode is a carbon electrode inoculated with an electrosynthetic microbiome poised at −590 mV vs. SHE, or any potential below −300 mV vs. SHE. In one embodiment, the electrosynthetic microbiome produces methane, which is then mixed with oxygen generated by the anode in a second reaction chamber, which contains a methanotroph or methanotrophic community that produces the PHA polyhydroxybutyrate (PHB) under nitrogen or phosphate limitation. Hydrogen or acetate produced by the electrosynthetic microbiome and carbon dioxide can also serve as substrates for PHA production by other microbes, such as found in activated sludge or wastewater. Some pure culture strains of *Ralstonia eutropha, E. coli*, and *Cupriavidus necator* could also be used to convert $H_2$ or acetate to PHAs. Any PHA-synthesizing microorganism may be used, either naturally-occurring or genetically-engineered. See, for example, U.S. Pat. No. 5,871,980, incorporated herein by reference. Additionally, the second chamber may connect to the biocathode with an anion exchange membrane to facilitate polymerization of the electrosynthesized fatty acids, such as acetate, butyrate, and propionate, into polyhydroxyalkanoates (PHA). The cells from the second chamber are concentrated using centrifugation or tangential flow filtration. The PHA is isolated from concentrated cells using detergent, from lyophilized cells using solvent extraction, or other suitable methods. See, for example, U.S. Pat. Publn. No. 20110160427, incorporated herein by reference.

Methanotrophic bacteria, such as *Methylocystis parvus* OBBP produce PHB from methane and oxygen under nutrient-limited conditions. Levels of production have accumulated to as high as 30 g/L PHB. Additionally, acetate can serve as a carbon source for *M. parvus*, but the energy comes from the reducing power of methane. Cells high in PHB consume it slower when in the presence of formate (Pieja 2011). Other bacteria can produce PHA from acidogenic waste streams rich in volatile fatty acids (Kasemsap 2007).

Example 3—Longterm Culture Studies

Materials and Methods
 Source of Microorganisms and Bioelectrochemical Setup
 Graphite granules and supernatant from the initial microbial electrosynthesis system described by in Examples 1-2 were used as inoculum for the MESs described in Example 3. The original source of microorganisms was from a wastewater basin at Palmetto Brewing Company in Charleston, S.C.

The reactor design, materials, and medium composition were exactly as described in Examples 1-2. Briefly, two identical custom glass chambers were clamped together with a Nafion 117 proton exchange membrane separating the two chambers (see e.g., FIG. 14). The total volume of each glass chamber was 150 mL. A graphite rod current collector connected to a titanium wire was buried under 30 g of graphite granules (Showa Denko) and connected to a VMP3 (Biologic) potentiostat in both the working (cathode) and counter (anode) electrode compartments. The cathode chamber was filled with 75 mL of freshwater medium, containing, per liter, 2.5 g $NaHCO_3$, 0.6 g $NaH_2PO_4$—$H_2O$, 0.25 g $NH_4Cl$, 0.212 g $MgCl_2$, 0.1 g KCl, 0.03 g $CaCl_2$, 20 mL vitamin solution, and 20 mL of mineral solution. The anode chamber was filled with 75 mL of the same medium except it contained 1 g KCl, 2 g NaCl to increase electrolyte concentration, and no vitamins or mineral solutions.

Figure 16:
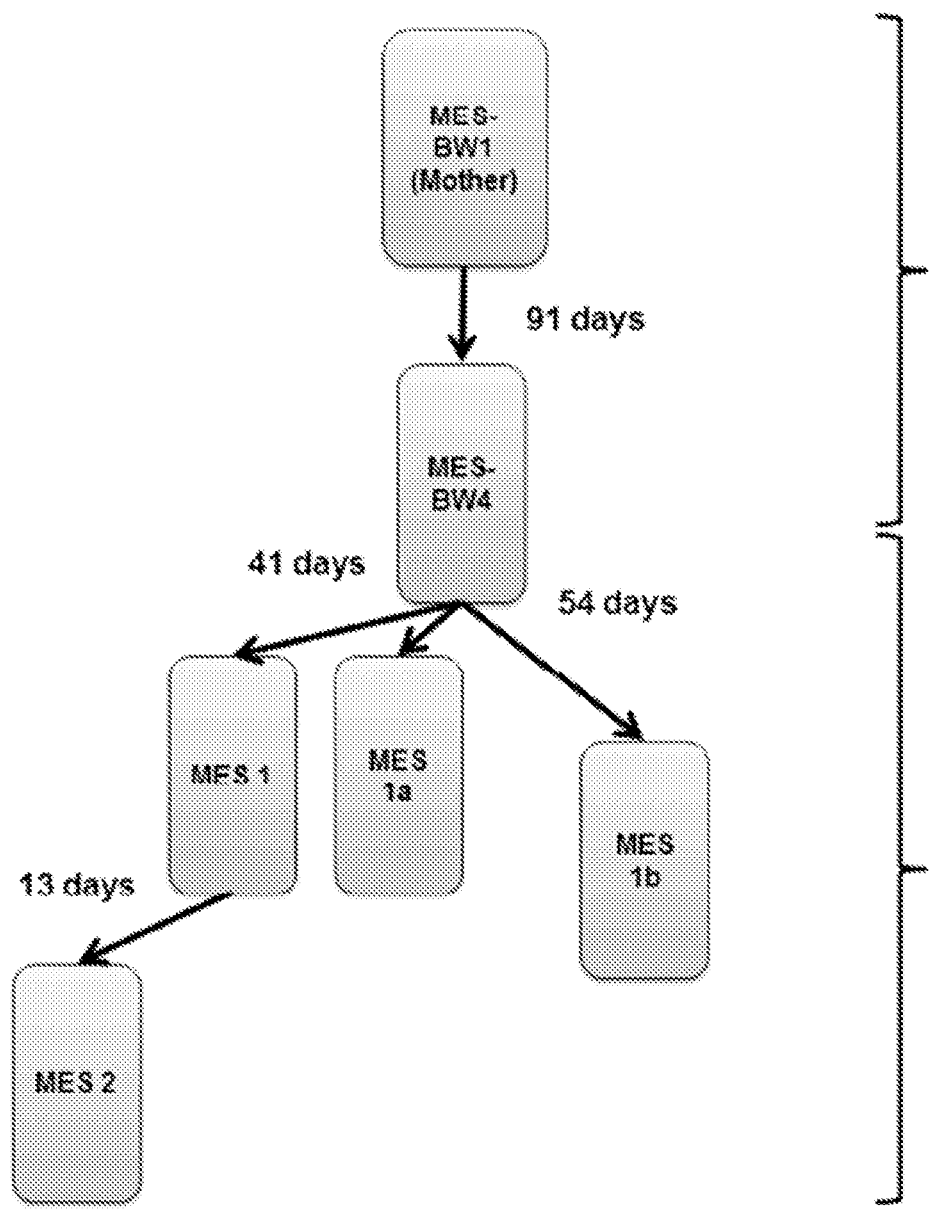
FIG. 16: Experimental Design of current study. The 'mother' reactor, MES-BW1, was transferred after 91 days to MES-BW4 (See, Examples 1-2). After 41 days of operation, granules (approximately 5 g) from MES-BW4 were transferred to MES 1 and MES 1a. After an additional 13 days (54 days total), approximately 5 g of granules were transferred to MES 1b. 13 days after the start of MES 1, granules were transferred from MES 1 to MES 2. MES 1 and 2 are described in Example 3.

After 41 days of operation of a previous MES (FIG. 3C), less than 10 mL of supernatant and approximately 5 g of granules were transferred to MES 1 of Example 3 (see FIG. 16). After 13 days of operation of MES 1, the supernatant and granules were transferred to MES 2 of this study. For the first 35 days of MES 1 and 72 days of MES 2, the cathode chamber was intermittently sparged with 100% $CO_2$. It was observed that the sparging of $CO_2$ led to an improvement of current draw and a remediation of the pH. Thus, at days 35 and 72, the cathode chambers of MES 1 and MES 2 were flushed with 100% $CO_2$ continuously using humidified gas. Sodium 2-bromoethanesulfonate was added to a final concentration of 10 mM in order to inhibit the methanogenic Archaea at the beginning of each batch cycle (unless otherwise noted).

Typical batch experiments (time between medium replacements) lasted 2-3 weeks, but a seven day yield test was performed to determine maximum rates of electroacetogenesis. During the yield test, the MESs were sparged once a day for 20 min with 100% $CO_2$ for the first three days (completely sealed otherwise). Subsequently, the MESs were continuously sparged with 100% $CO_2$ for the remaining four days.

All experiments were run in 3-electrode poised potential mode with a 3 M KCl Ag/AgCl (+210 mV versus SHE) reference electrode at 25±2° C. The MESs were poised at −590 mV vs SHE except for occasional short-term experiments where higher potentials were tested (FIG. 17). Reference electrodes were tested at every medium exchange to ensure that the potential was ±20 mV of +210 mV. All potentials reported in this study are versus SHE.

Cyclic voltammetry (CV) experiments were conducted with a 10 $cm^2$ graphite rod electrode in the same bioelectrochemical reactors described. The granules from MES 2 were taken out of the MES at the time of a medium exchange, leaving only the 10 $cm^2$ graphite rod. Scans ranged from −0.200 V to −1.0 V vs SHE at 1 mV s-1. CV was performed on blank medium with 10 mM sodium 2-bromoethanesulfonate, supernatant from MES 2 filtered through a 0.2 μm filter, MES 2 immediately after rinsing and exchanging the medium, one day after a medium exchange, and five days after a medium exchange.

Analytical Methods
 Gasses (methane and hydrogen) were analyzed periodically using a HP6890 GC with a TCD and a HP-PLOT Molesieve 5 A column (see Example 1). During continuous sparging, headspace samples were taken periodically and immediately analyzed by GC while gas flow rates were measured as the gas left the cathode chamber. Flow rates were used to quantify gas concentrations in the headspace. Fatty acid concentrations were measured with an Aminex HP-87H column on a Shimadzu LC-adVP HPLC equipped with a UV detector and a mobile phase of 0.005 M $H_2SO_4$.

Scanning Electron Microscopy
 Three graphite granules from the cathode compartment were fixed for 3 h in 2% gluteraldehyde in a 0.1 M sodium cacodylate buffer. Then, the granules were washed with 2.5% osmium tetroxide for 1 h. They were then dehydrated using a graded ethanol wash (25, 50, 75, 95, and 100%). The three granules were sputter coated and imaged using a JEOL JSM-5600LV SEM. All images were representative of the biofilm coverage on each of the granules.

RNA Extraction
 Samples for RNA extraction (culture supernatant or graphite granules) were aseptically and anaerobically removed from MESs. Supernatant (40 mL) was filtered through a 0.22 μm Sterivex GP filter unit (Millipore) or graphite granules (~10 mL) were placed into a 50 mL conical tube, and each sample was immediately flash-frozen in liquid nitrogen. Samples were placed at −80° C. until further processing.

To process, Buffer RLT (Qiagen; RNeasy kit), β-mercaptoethanol (10 μL/mL of RLT), and silicon carbide beads (DNase- and RNase-free mixture of 0.1 mm and 1 mm) were added to frozen granules or Sterivex filter units. Samples were then incubated at room temperature for 10 min and subsequently subjected to 5 freeze/thaw cycles (i.e., freeze in liquid nitrogen, thaw at 55° C., vortex 6 min, and repeat). Following this, cellular debris and granules were pelleted by centrifugation. The RNA from the resultant supernatant was purified using an RNeasy kit (Qiagen), and residual DNA was removed via DNase treatment (TURBO DNA-free kit, ABI). RNA was assessed with a Nanodrop Spectrophotometer (Thermo Scientific, Wilmington, Del., USA).

RT-PCR Amplification and 16S rRNA Sequencing were performed as detailed in Example 1.

Taxonomic Classification.
 Sequences were preprocessed and analyzed in mothur v. 1.27.15,16 using previously described workflows (see Example 1). Briefly, preprocessing removed sequences containing low average quality scores (<25), spurious read lengths (<200 or >700 bp), ambiguous base calls, ≥8 homopolymers, or >1 mismatch to the barcode or primer. Remaining reads were aligned against the Greengenes core database (DeSantis et al., 2006), then priming sequences were removed, and reads were trimmed to the amplicon region. Resulting reads shorter than 350 bp or those likely due to sequence error (Huse et al. 2010) or chimeras (Edgar et al. 2011) were removed. Reads were then classified with a Bayesian approach (bootstrap cutoff of 80) against the SILVA database (Pruesse et al. 2007). Pacific Biosciences circular consensus sequences have been submitted to the GenBank Sequence Read Archive under SRA073132, incorporated herein by reference.

Results

Figure 18:
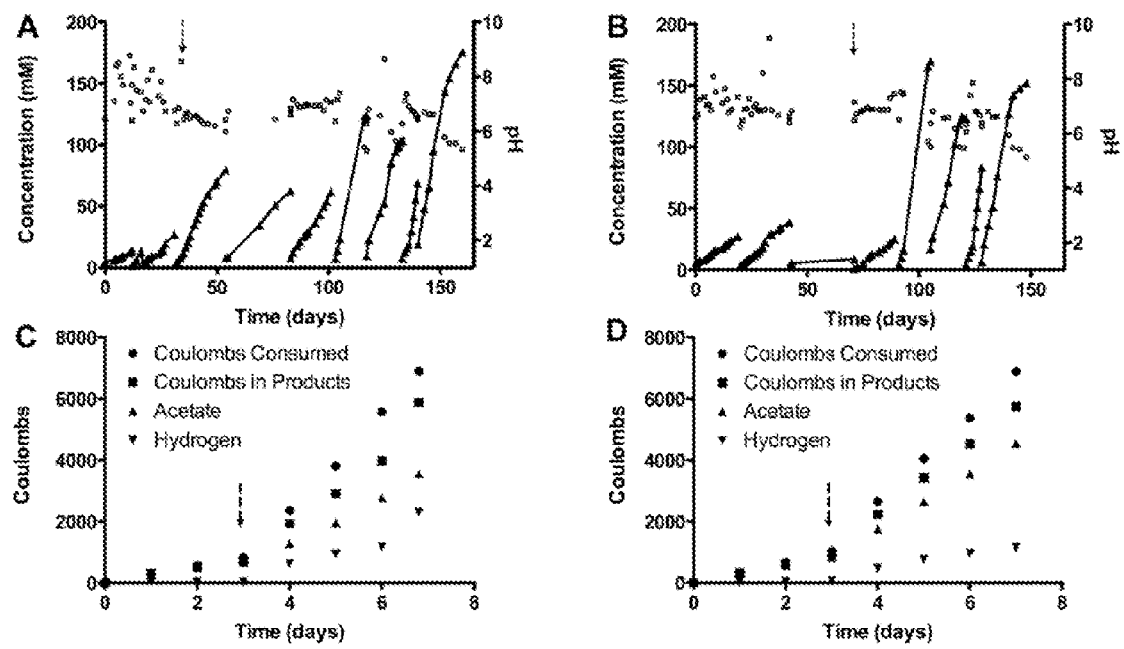
FIG. 18: Representative electroacetogenic reactors MES 1 and MES 2 (A and B, respectively) operating for over 150 days producing acetate (triangles) as the dominant product (pH indicated by open squares). No sodium 2-bromoethanesulfonate was added on days 83-101 in MES 1 and days 71-89 in MES 2. (C and D) Yield tests were conducted on days 133-140 of MES 1 and 121-128 of MES 2. Coulombic efficiency averaged 84.3±7.6% in all products (hydrogen, acetate, formate, propionate, and butyrate). Arrows represent the switch to continuous $CO_2$ sparging.

Bioelectrochemical systems originally developed with brewery wastewater were operated for over 150 days at an applied cathode potential of −590 mV vs SHE (occasionally, higher potentials were tested, (FIG. 17); all potentials reported versus the standard hydrogen electrode). Twenty-nine days after the initial inoculation of the microbial electrosynthesis system, the methanogenic inhibitor 2-bromoethanesulfonate was added at the time of a medium exchange. This effectively knocked down methanogenic activity, converting the MES into a predominantly acetate and hydrogenproducing bioreactor. Supernatant and/or granules from this acetogenic and hydrogenic reactor could be used as inoculum for other reactors without any loss in productivity. FIGS. 18A and B shows acetate production and pH in two representative reactors, MES 1 and MES 2, over 150 days. These two reactors represent the second and third successive transfers of the electrosynthetic cultures, indicating transferability and reproducibility of this culture. In total, five electroacetogenic MESs that all behaved similarly were operated in this study (see FIG. 16 and Table 5).

(mM d$^{-1}$), but after constant $CO_2$ sparging and prolonged exposure to the electrode, the rate improved to 5.0±0.75 mM d$^{-1}$ (Table 5), surpassing the rates indicated in Example 2 (rates include lag and stationary phase of batch experiment). Additionally, rates improved over the course of the constant $CO_2$ sparging. During the first half of the time course that $CO_2$ was continuously sparged, the acetate production rate was 3.88±0.47 mM d$^{-1}$ and during the second half of the time course the acetate production rate was 5.62±1.39 mM d$^{-1}$. The maximum accumulation of acetate observed was 175 mM (10.5 g L$^{-1}$) over a 20 day span. The maximum rate of acetate production was 17.25 mM d$^{-1}$ (1.04 g L$^{-1}$ d$^{-1}$). This rate of acetate production is 1500× higher than the calculated rate of acetate production that could be attributed to hydrogen production in abiotic controls (0.01125 mM d$^{-1}$). These rates of acetate production are substantially higher (10-100×) than reported rates for microbial electrosynthesis (Nevin et al., 2010; Nevin et al., 2011; Zhange et al. 2013).

Figure 19:
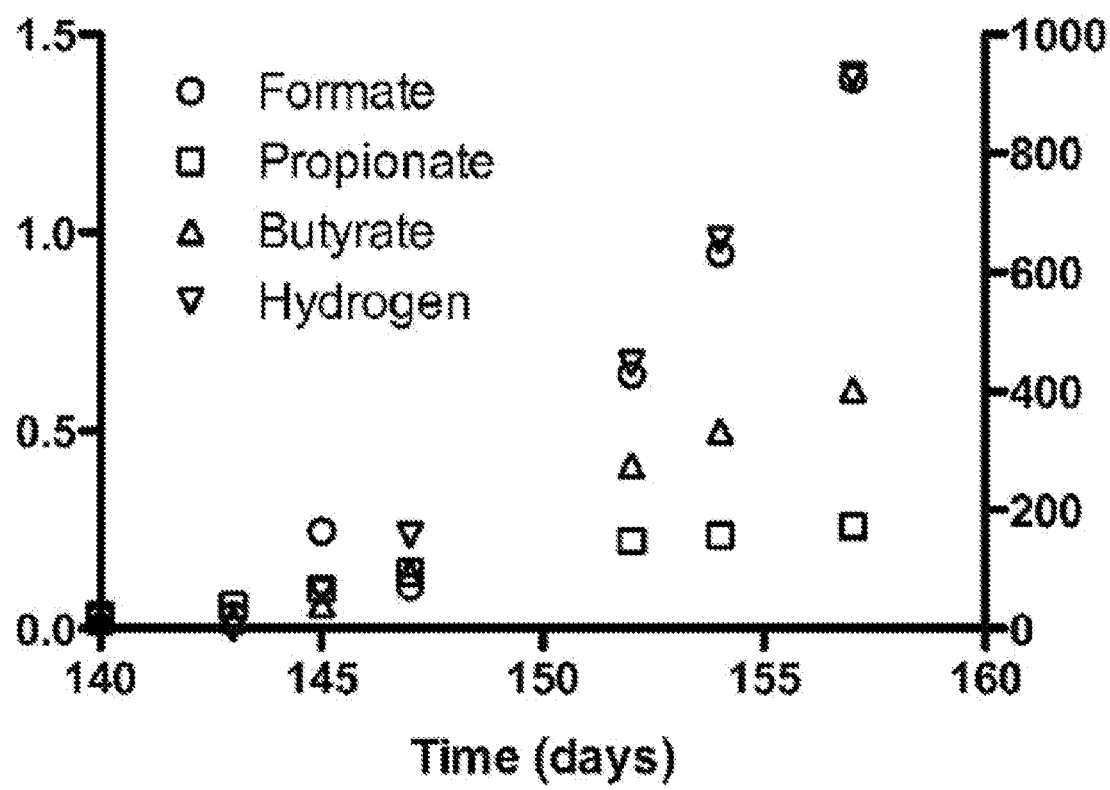
FIG. 19: Plot of all products except acetate produced by the electrosynthetic microbiome in MES 1, acetate accumulated to 166 mM over this time.

Over the same time span, hydrogen was concomitantly produced at considerable rates (FIG. 18C, D, and FIG. 19). Although gas was being continuously stripped away for most of the experiment, the highest calculated total of hydrogen detected was 1164 mM over 20 days (2.4 g L$^{-1}$) (calculated per L liquid volume). Rates of hydrogen generation averaged 20.6±8.0 mM d$^{-1}$ (0.041±0.016 g L$^{-1}$ d$^{-1}$), but rates as high as 100 mM d$^{-1}$ (0.2 g L$^{-1}$ d$^{-1}$) were observed.

The Coulombic efficiency of the MESs for all products during a week-long yield test was 84.3±7.6% (FIGS. 18C

TABLE 5

Effects of $CO_2$ sparge of acetate production in various MES systems

| Reactor | Switch to constant $CO_2$ flushing (days after inoculation) | Final day | Before constant $CO_2$ sparge Avg. acetate production rate (mM d$^{-1}$) | After constant $CO_2$ sparge Avg. acetate production rate (mM d$^{-1}$) | 1$^{st}$ ½ of $CO_2$ sparge Avg. acetate production rate (mM d$^{-1}$) | 2$^{nd}$ ½ of $CO_2$ sparge Avg. acetate production rate (mM d$^{-1}$) | Max acetate production rate (mM d$^{-1}$) |
|---|---|---|---|---|---|---|---|
| MES-BW 4 | 75 | 191 | 1.5 | 4.9 | 4.6 | 5.0 | 11.3 |
| MES 1 | 35 | 150 | 1.8 | 5.3 | 3.2 | 6.6 | 16.8 |
| MES 1a | 35 | 150 | 2.0 | 4.1 | 3.8 | 4.2 | 9.1 |
| MES 1b | 23 | 150 | 1.6 | 4.3 | 4.3 | 4.2 | 12.2 |
| MES 2 | 72 | 150 | 1.4 | 6.4 | 3.5 | 8.1 | 17.3 |

| Reactor | CE$^a$ | Yield test (days 0-3) Avg. current (mA) | Yield test (days 4-7) Avg. current (mA) | Yield test (days 4-7) Avg. current density (A m$^{-3}$ total cathode volume) | Yield test (days 4-7) Avg. current density (A m$^{-3}$ cathode liquid volume) |
|---|---|---|---|---|---|
| MES-BW 4 | 84 | 3.9 | 9.5 | 63.3 | 126.78 |
| MES 1 | 89 | 3.1 | 18.7 | 124.7 | 249.3 |
| MES 1a | 72 | 2.9 | 7.2 | 48 | 96.0 |
| MES 1b | 79$^b$ | 3.4 | 8.5 | 56.7 | 113.3 |
| MES 2 | 92 | 4.0 | 17.2 | 114.7 | 229.3 |

$^a$CE is coulombic efficiency during yield test
$^b$Number reported for first three days of yield test due to sampling errors during the final 4 days.

Due to the consumption of $CO_2$ and protons at the cathode, implemented. However, it was observed that the constant addition of 100% $CO_2$ prevented the pH from exceeding 7.5 (FIGS. 18A and B). Additionally, noticeable increases in rates were first observed when the headspace was sparged with $CO_2$ and have continued to increase over time with continuous $CO_2$ sparging. The rate of acetate production of the MESs with intermittent $CO_2$ flushes was 1.66±0 2 mmol per liter of cathode liquid volume per day and D). During the yield tests, the MESs were sealed for the first three days, and then a constant stream of $CO_2$ was bubbled through the reactor for the remaining four days (arrows, FIGS. 18C and D). The sparging of $CO_2$ stimulated a substantial increase in the rate of acetate and hydrogen production by the MESs. In all cases, the coulombs in acetate were >50%, and reached as high as 69% of the total coulombs consumed based on current measurements, indicating that electroacetogenesis was the dominant metabolic activity coupled to the generation of current. Hydrogen generation resulted in the second highest share of electrons, equaling 3-33% of total coulombs consumed. Formate, propionate, and butyrate were consistently observed in lesser quantities in the MESs (FIG. 19), with formate accumulating to as high as 1.4 mM.

CV experiments using a defined electrode surface area (10 cm$^2$ graphite rod) revealed a biocathode-dependent catalytic wave compared to blank electrodes (FIG. 20). The onset of cathodic current (the x-intercept) during the reductive scan with the blank electrode or the cell-free supernatant occurred below −500 mV (upper traces). Contrast this with the electrode containing the electrosynthetic biofilm, which developed cathodic current below −260 mV. A reversible biocatalytic curve was evident with a midpoint potential of −475 mV (lower traces). A similar curve (with slightly lower current density at −590 mV) developed immediately after a replacement of the spent medium and remained after one day, indicating that no soluble electron shuttles were washed away after an exchange of the medium and that biocatalytic activity was not impaired by unpoising or medium exchanges. The current density of the defined electrode while poised at −590 mV was 2.5 A m-2.

Figure 21:
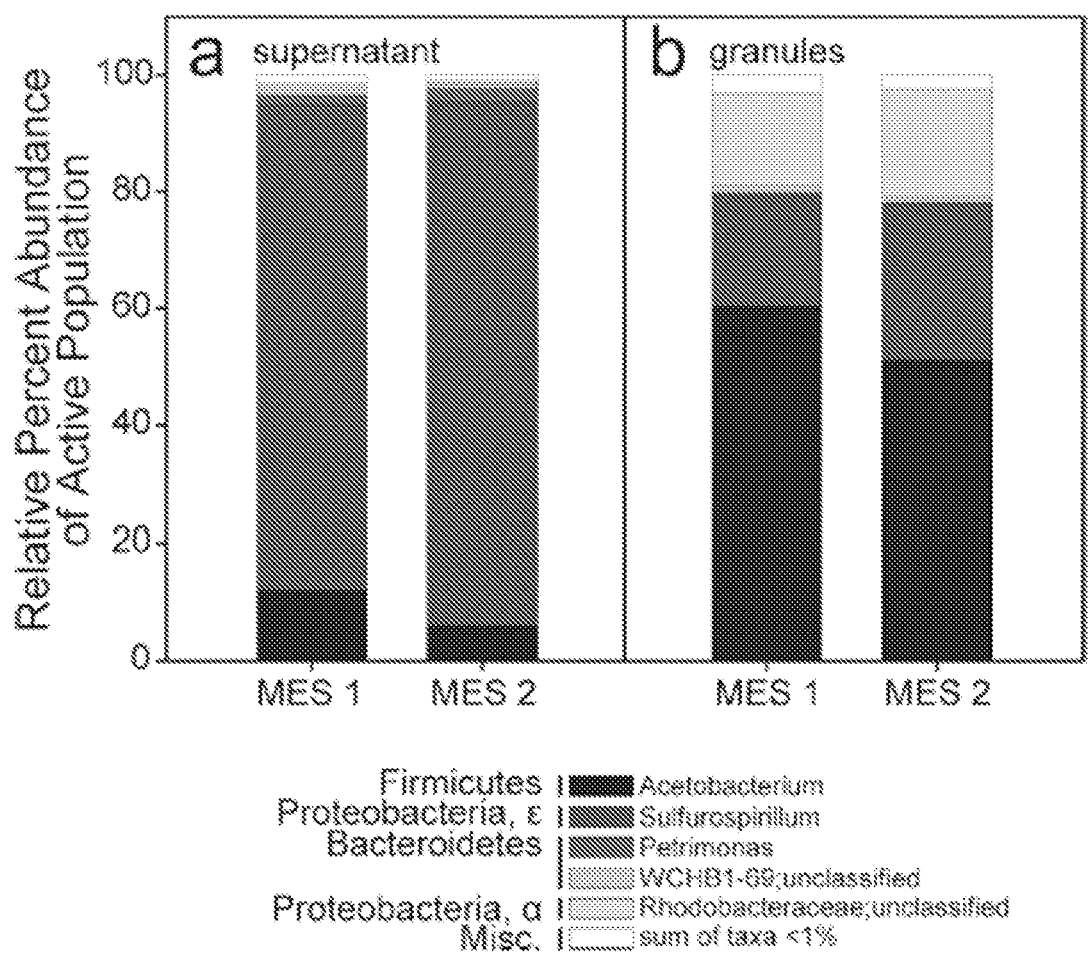
FIG. 21: Relative abundance of bacterial 16S rRNA from active electrosynthetic communities in MES 1 and MES 2 after 140 and 128 days, respectively. Metabolically active communities within the supernatant (A) or granules (B) of acetate/hydrogen-producing MESs are shown to the genus-level where possible.

A phylogenetic analysis on the active microbiome in the supernatant (FIG. 21A) and granules (FIG. 21B) was conducted on MES 1 after 140 days and MES 2 after 128 days of operation. Analysis of the active microbial members of the graphite electrode biofilm revealed that 51-60% of the 16S rRNA sequences were most similarly related to *Acetobacterium* spp. (FIG. 21B). This was expected since *Acetobacterium* was one of the dominant active genera present on the cathode granules in the original reactor that served as the inoculum (see Example 2). Despite no significant increase in the relative abundance of *Acetobacterium* from the original reactor to the present reactors, a ≥50% reduction in the number of abundant taxa (taxa with ≥1% abundance) was observed, indicating a decrease in richness as the reactors have selected for electrode-dependent metabolic activity. The two other dominant groups present in electrode biofilms were from the Rhodobacteraceae family (15.9-18.7%) and *Sulfurospirillum* genus (18.9-26.9%).

The active supernatant population, on the other hand, was dominated by *Sulfurospirillum* spp. (82.8-89.3%) (FIG. 21B). This finding was consistent with that observed in the original supernatant community, described in Example 2. *Acetobacterium* spp. accounted for most of the remaining active taxa in the supernatant community (6-12%).

Figure 26:
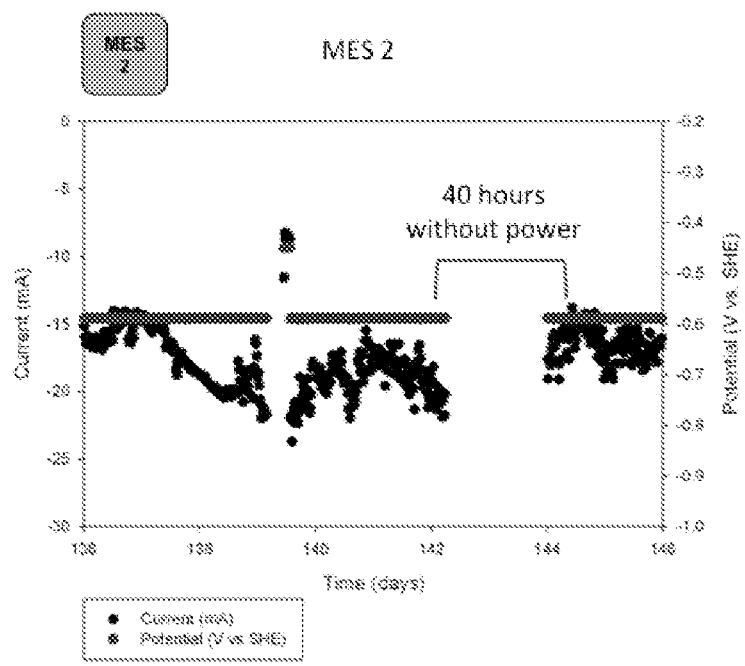
FIG. 26: Graph shows the effect of power disruption on a microbial reactor of the embodiments.

After 180 days of MES operation, multiple graphite granules were fixed and analyzed by scanning electron microscopy. The electroacetogenic biofilms revealed a high density of short tapered rods of approximately 1.5 µm long and 0.5 µm thick. Compared to the same reactor after 56 days (Example 2), biofilm coverage noticeably increased after an additional 124 days, indicating electrodeassociated growth. Microorganisms covered most of the granules, and many areas contained cells stacked 3-4 layers deep. Further studies addressed the robustness of microbial populations and cathode biofilms by assessing the effect of power disruption on the system. As shown in FIG. 26, even after 40 hours no applied potential the system returned to nominal operation after power was restored.

Example 4: Additional Manipulation of Microbial Cultures

Further studies were undertaken to determine how production from the cathode biofilms might be further modulated. For these further studies a 100 mM potassium phosphate buffering system was substituted for the previous sodium bicarbonate buffer. Furthermore, a culture volume of 50 mL (instead of 75 mL) was used in each chamber and 25 grams (rather than 30 grams) of graphite granules were employed.

Figure 22A:
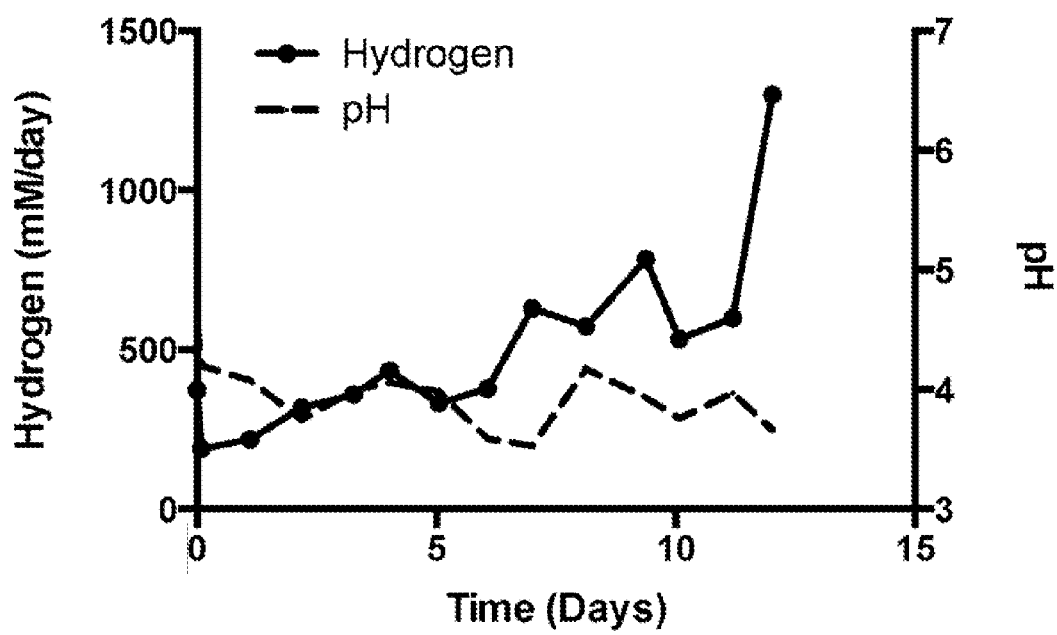
FIG. 22A-C: Graphs show the effects of culture pH on $H_2$ production. (A) Graph shows that $H_2$ production increases as a function of time while culture pH is maintained between about 3.5 and 4.5. (B) Graph shows that $H_2$ production is responsive to changes in pH. Upon acidification (with HCl) $H_2$ productions increase. $H_2$ production was initially squelched by NaOH addition and the return of a more neutral pH. (C) Graph shows that high $H_2$ production (upper panel) can be maintained at a higher pH (e.g., between 6 and 7) if the culture was previously at lower pH. Significant acetate production was likewise observed (lower panel). The data are results from biocathodes that were first exposed to pH 4 to 5 and then the pH was maintained between 6 and 7.
Figure 22B:
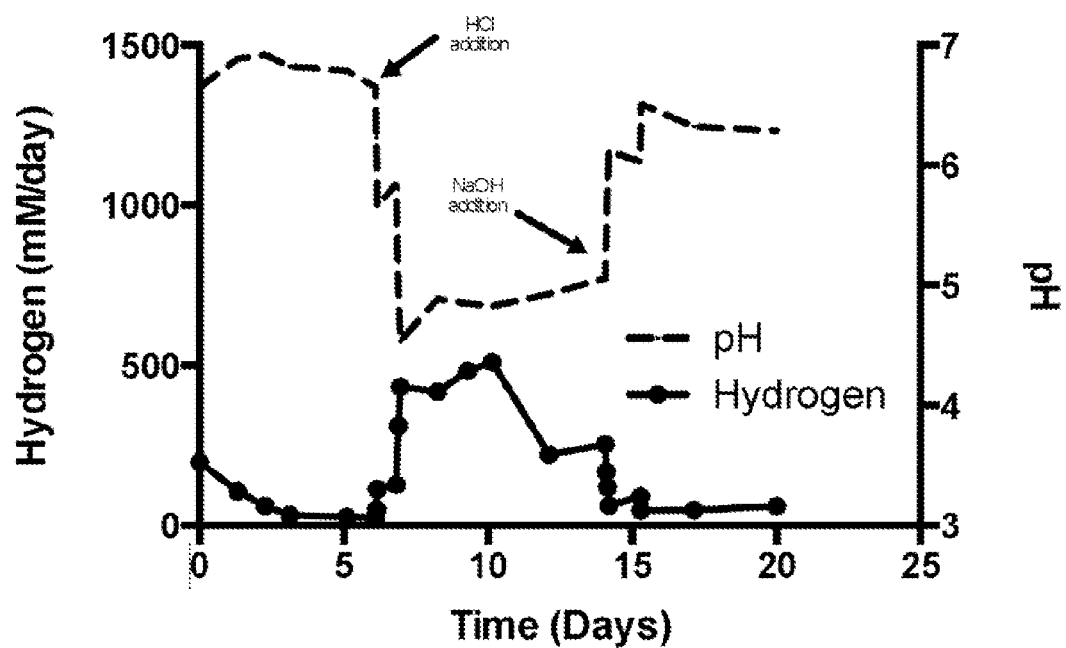
Figure 22C:
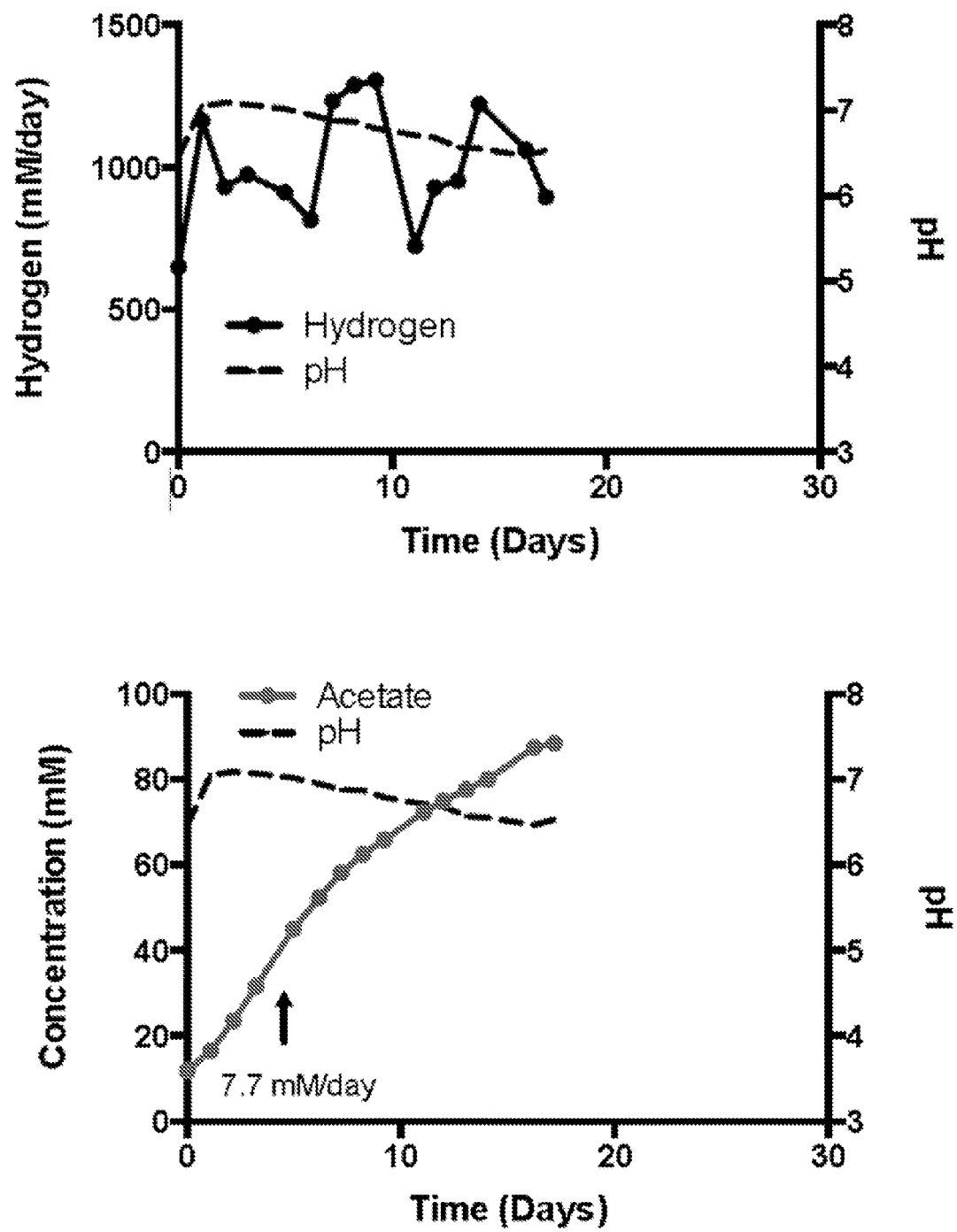
Figure 23:
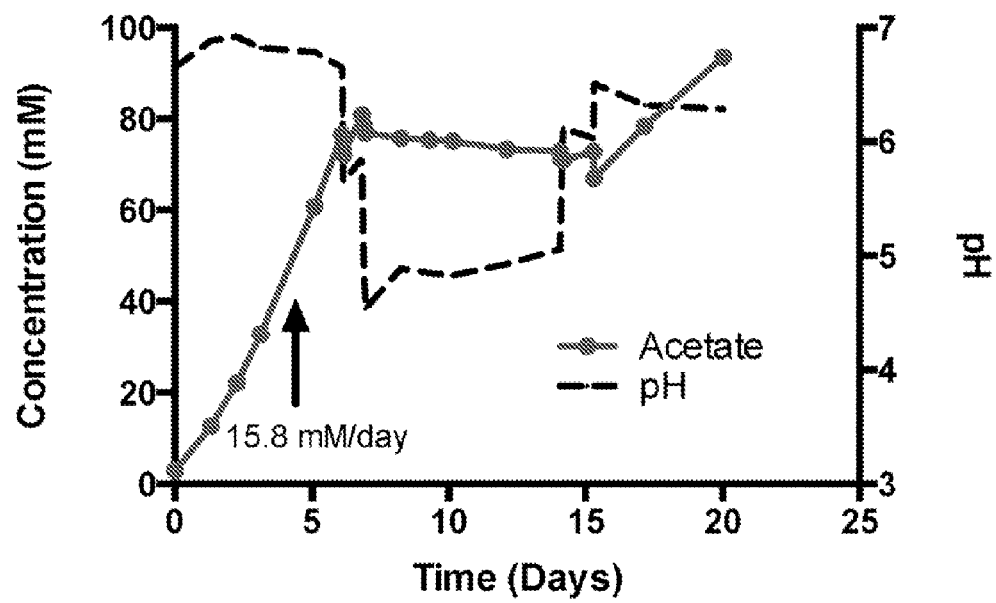
FIG. 23: Graph show the effect of culture pH on acetate production. Acetate production is responsive to changes in pH. A neutral pH of between about 6.0 and 7.0 allows for robust acetate production. Upon acidification (to ~pH 5.0) acetate production decreases. Restoration of a neutral pH restores increased acetate production.

In the first set of studies the pH of the culture environments was modulated and it was established that acid pH favored hydrogen production, whereas more neutral pH was more favorable to acetate production. FIG. 22A-B, for example, shows the effects of culture pH on $H_2$ production. The studies showed that $H_2$ production increased as a function of time while culture pH is maintained between about 3.5 and 4.5 (FIG. 22A). Upon changing the pH to a more neutral 6.0-7.0 $H_2$ production was initially reduced. However, further studies demonstrated that high $H_2$ production can be maintained at a higher pH (between 6 and 7) if the culture was previously at lower pH (FIG. 22C). For acetate production a neutral pH of between about 6.0 and 7.0 allowed for robust synthesis (FIG. 22C and FIG. 23). However, acetate production was reduced upon acidification (to ~pH 5.0; FIG. 23).

Figure 24:
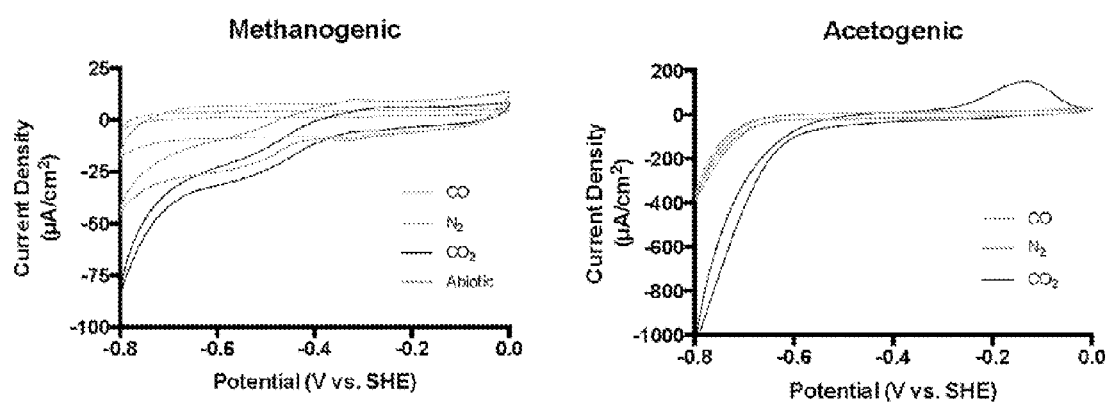
FIG. 24: Graphs show cyclic voltammetry on methanogenic and acetogenic cultures under different atmospheres.
Figure 25:
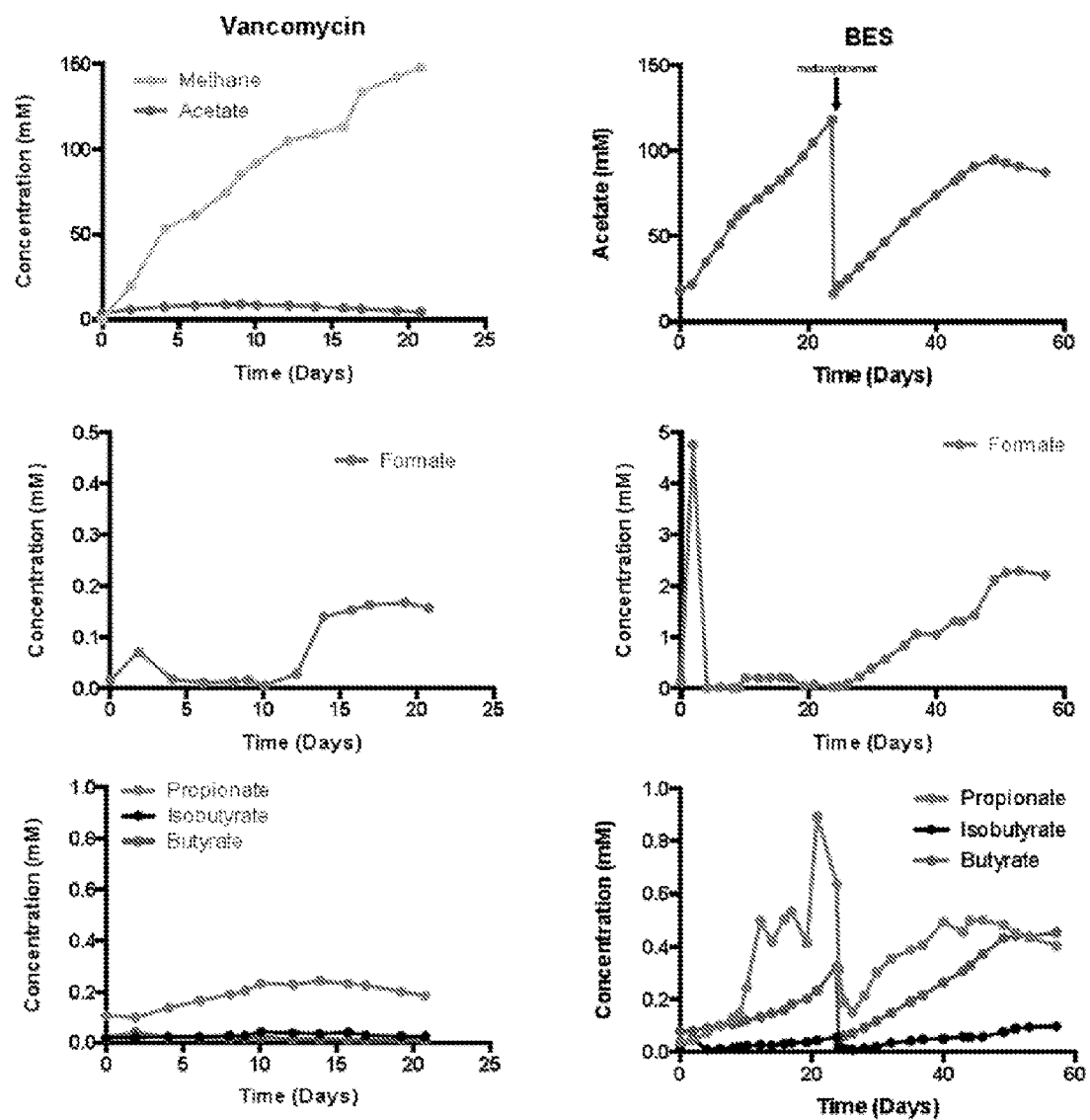
FIG. 25: Graphs show the effects of Vancomycin (left graphs) or BES (rights graph) on production of methane, acetate, formate, propionate isobutyrate and butyrate. Vancomycin treated cultures favor methane production, whereas BES treatment favors acetate, propionate isobutyrate and butyrate production.

Various compounds were also used to select particular organisms in microbial communities and the effects on compound synthesis were observed. For example, Vancomycin treatment (to reduce the presence of certain microbial populations yielded enhanced methane synthesis). On the other hand, the presence of BES enhanced the relative levels of acetate, propionate, isobutyrate and butyrate production. The effects of atmosphere content upon methanogenic versus acetogenic culture systems were also studied. Results of these studies showed that carbon dioxide atmospheres resulted in higher cathodic current densities on graphite rod electrodes, whereas carbon monoxide inhibited much of the cathodic current (FIG. 24).

Example 5: Combined Anode/Cathode Microbial Reactors

A combined biological (microbial) and bioelectrochemical process is may also be used to convert $CH_4$ and $CO_2$ into liquid hydrocarbons. Such a system can be achieved with microorganisms acting at the electrodes of an electrochemical cell. In this case, one population (e.g., methanotrophic bacteria) will provide anaerobic oxidation of $CH_4$ at a carbon anode and the synthesis of acetic acid from $CO_2$ at a carbon cathode is achieved by electroacetogenic microbes (such as those populations detailed in Examples 2-4). In essence, the reaction is the reverse of acetotrophic methanogenesis, an unfavorable reaction ($\Delta G^{\circ\prime}=30.7$ kJ/mol) that can be made favorable with the supply of low voltage to the cathode (0.5 to 0.6V). Ordinarily the electrosynthesis of acetate from $CO_2$ would require additional energy to oxidize water at the anode, but this requirement will be minimized by the oxidation of $CH_4$ at the anode. Since this is an anaerobic process the safety risks associated with combining $O_2$ and $CH_4$ are significantly reduced. Methane oxidation in a microbial fuel cell (MFC) has been reported (see, e.g., US Patent Publication US 2011/0123835, incorporated herein by reference.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Publn. No. 2011/0123835

Abram A, Foster D L. 2005. A primer on ammonia, nitrogen fertilizers, and natural gas markets. Ohio State University AEDE-RP-0053-05.

Aulenta F, Catapano L, Snip L, Villano M, Majone M. 2012. Linking Bacterial Metabolism to Graphite Cathodes: Electrochemical Insights into the H(2)-Producing Capability of *Desulfovibrio* sp. ChemSusChem 5:1080-1085.

Balash P C, Kern K C. 2008. Natural gas and electricity costs and impacts on industry. U.S. Department of Energy DOE/NETL-2008/1320.

Bar-Even, A.; Noor, E.; Milo, R. A survey of carbon fixation pathways through a quantitative lens. J. Exp. Botany 2012, 63 (6), 2325-42.

Braun, M.; Gottschalk, G. *Acetobacterium wieringae* sp. nov., a new species producing acetic acid from molecular hydrogen and carbon dioxide. Zentralblatt für Bakteriologie Mikrobiologie und Hygiene: I. Abt Originale C: Allgemeine, angewandte und ðkologische Mikrobiologie 1982, 3 (3), 368-376.

Cheng S, Logan B E. 2007. Sustainable and efficient biohydrogen production via electrohydrogenesis. Proc Natl Acad Sci USA 104:18871-18873.

Cheng S, Xing D, Call D F, Logan B E. 2009. Direct biological conversion of electrical current into methane by electromethanogenesis. Environ Sci Technol 43:3953-3958.

Cheung H, Tanke R S, Torrence G P. 2005. Acetic Acid. Ullman's Encyclopedia of Industrial Chemistry Wiley-VCH, Weinheim.

Demler, M.; Weuster-Botz, D. Reaction engineering analysis of hydrogenotrophic production of acetic acid by *Acetobacterium woodii*. Biotechnol. Bioeng. 2011, 108 (2), 470-4.

DeSantis T Z, Hugenholtz P, Larsen N, Rojas M, Brodie E L, Keller K, Huber T, Dalevi D, Hu P, Andersen G L. 2006. Greengenes, a chimera-checked 16S rRNA gene database and workbench compatible with ARB. Appl. Environ. Microbiol. 72:5069-5072.

Drake H L, Gossner A S, Daniel S L. 2008. Old acetogens, new light. Ann NY Acad Sci 1125:100-128.

Edgar R C, Haas B J, Clemente J C, Quince C, Knight R. UCHIME improves sensitivity and speed of chimera detection. Bioinformatics 2011, 27:2194-2200.

Edwards U, Rogall T, Blocker H, Emde M, & Bottger E C (1989) *Nuc. Acids Res.* 19, 7843-7853.

Eid J, Fehr A, Gray J, Luong K, Lyle J, Otto G, Peluso P, Rank D, Baybayan P, Bettman B, Bibillo A, Bjornson K, Chaudhuri B, Christians F, Cicero R, Clark S, Dalal R, deWinter A, Dixon J, Foquet M, Gaertner A, Hardenbol P, Heiner C, Hester K, Holden D, Kearns G, Kong X, Kuse R, Lacroix Y, Lin S, Lundquist P, Ma C, Marks P, Maxham M, Murphy D, Park I, Pham T, Phillips M, Roy J, Sebra R, Shen G, Sorenson J, Tomaney A, Travers K, Trulson M, Vieceli J, Wegener J, Wu D, Yang A, Zaccarin D, Zhao P, Zhong F, Korlach J, Turner S. 2009. Real-Time DNA Sequencing from Single Polymerase Molecules. Science 323:133-138.

Energy USDo. 2010. Vehichel Technologies Program: Natural Gas Basics. DOE/GO-102010-3068.

Erickson, B, and P Winters. 2012. "Perspective on Opportunities in Industrial Biotechnology in Renewable Chemicals." *Biotechnology Journal*.

Gunsalus R P, Romesser J A, Wolfe R S. 1978. Preparation of coenzyme M analogues and their activity in the methyl coenzyme M reductase system of *Methanobacterium thermotophicum*. Biochemistry 17:2374-2376.

Hackett J T ea. 2011. Prudent Development: Realizing the Potential of North America's Abundanat Natural Gas and Oil Resources. National Petroleum Council for the U.S. Department of Energy.

Huse S M, Welch D M, Morrison H G, Sogin M L. 2010. Ironing out the wrinkles in the rare biosphere through improved OTU clustering. Environ. Microbiol. 12:1889-1898.

Kasemsap et al., Batch production of polyhydroxyalkanoate by low-polyphosphate-content activated sludge at varying pH, *Bioresource Technology*, 98:1020-1027, 2007.

King, D., Inderwildi, 0. R., Williams, A. "The Future of Industrial Biorefineries." World Economic Forum, June 2010.

Labelle E V, May H D. 2012. Planned for publication.

Li H, Opgenorth P H, Wernick D G, Rogers S, Wu T-Y, Higashide W, Malati P, Huo Y-X, Cho K M, Liao J C. 2012. Integrated Electromicrobial Conversion of CO2 to Higher Alcohols. Science 335:1596.

Logan B E. 2009. Exoelectrogenic bacteria that power microbial fuel cells. Nat Rev Micro 7:375-381.

Logan B E, Hamelers B, Rozendal R, Schroder U, Keller J, Freguia S, Aelterman P, Verstraete W, Rabaey K. 2006. Microbial fuel cells: methodology and technology. Environ Sci Technol 40:5181-5192.

Lovley D R. 2006. Bug juice: harvesting electricity with microorganisms. Nature Reviews Microbiology 4:497-508.

Mamedov T G, Pienaar E, Whitney S E, TerMaat J R, Carvill G, Goliath R, Subramanian A, Viljoen H J. 2008. A fundamental study of the PCR amplification of G C-rich DNA templates. Computational Biology and Chemistry 32:452-457.

McLean, J. S.; Wanger, G.; Gorby, Y. A.; Wainstein, M.; McQuaid, J.; Ishii, S. I.; Bretschger, O.; Beyenal, H.; Nealson, K. H. Quantification of electron transfer rates to a solid phase electron acceptor through the stages of biofilm formation from single cells to multicellular communities. Environ. Sci. Technol. 2010, 44 (7), 2721-7.

McInerney J O, Wilkinson M, Patching J W, Embley T M, & Powell R (1995) *Appl. Environ. Microbiol.* 61, 1646-1648.

Needleman S B, Wunsch C D. 1970. A GENERAL METHOD APPLICABLE TO SEARCH FOR SIMILARITIES IN AMINO ACID SEQUENCE OF 2 PROTEINS. Journal of Molecular Biology 48:443-&.

Nercessian O, Fouquet Y, Pierre C, Prieur D, & Jeanthon C (2005) *Environ. Microbiol.* 7, 698-714.

Nevin K P, Hensley S A, Franks A E, Summers Z M, Ou J, Woodard T L, Snoeyenbos-West O L, Lovley D R. 2011. Electrosynthesis of Organic Compounds from Carbon Dioxide Is Catalyzed by a Diversity of Acetogenic Microorganisms. Appl. Environ. Microbiol. 77:2882-2886.

Nevin K P, Woodard T L, Franks A E, Summers Z M, Lovley D R. 2010. Microbial electrosynthesis: feeding microbes electricity to convert carbon dioxide and water to multicarbon extracellular organic compounds. mBio 1.

Osborn S G, Vengosh A, Warner N R, Jackson R B. 2011. Methane contamination of drinking water accompanying gas-well drilling and hydraulic fracturing. Proc Natl Acad Sci USA 108:8172-8176.

Parrondo J, Herrero M, Garcia L A, Diaz M. 2003. A note—production of vinegar from whey. J. Institute Brewing 109:356-358.

Pieja et al., Poly-3-hydroxybutyrate metabolism in the type II methanotroph *Methylocystis parvus* OBBP, *Applied and Environmental Microbiology*, 77:6012-6019, 2011.

Pisciotta J M, Zaybak Z, Call D F, Nam J Y, Logan B E. 2012. Enrichment of microbial electrolysis cell (MEC) biocathodes from sediment microbial fuel cell (sMFC) bioanodes. Appl Environ Microbiol.

Pruesse E, Quast C, Knittel K, Fuchs B M, Ludwig W G, Peplies J, Glockner F O. 2007. SILVA: a comprehensive online resource for quality checked and aligned ribosomal RNA sequence data compatible with ARB. Nucleic Acids Res. 35:7188-7196.

Rabaey K, Rozendal R A. 2010. Microbial electrosynthesis—revisiting the electrical route for microbial production. Nature reviews. Microbiology 8:706-716.

Ren, Z.; Ramasamy, R. P.; Cloud-Owen, S. R.; Yan, H.; Mench, M. M.; Regan, J. M. Time-course correlation of biofilm properties and electrochemical performance in single-chamber microbial fuel cells. Bioresour. Technol. 2011, 102 (1), 416-21.

Rostkowski, K H, C S Criddle, and Michael D Lepech. 2012. "Cradle-to-Gate Life Cycle Assessment for a Cradle-to-Cradle Cycle: Biogas-to-Bioplastic (and Back)." *Environmental Science & Technology*.

Rozendal R A, Jeremiasse A W, Hamelers H V, Buisman C J. 2008. Hydrogen production with a microbial biocathode. Environ Sci Technol 42:629-634.

Schloss P D, Westcott S L. 2011. Assessing and Improving Methods Used in Operational Taxonomic Unit-Based Approaches for 16S rRNA Gene Sequence Analysis. Appl. Environ. Microbiol. 77:3219-3226.

Schloss P D, Westcott S L, Ryabin T, Hall J R, Hartmann M, Hollister E B, Lesniewski R A, Oakley B B, Parks D H, Robinson C J, Sahl J W, Stres B, Thallinger G G, Van Horn D J, Weber C F. 2009. Introducing mothur: Open-Source, Platform-Independent, Community-Supported Software for Describing and Comparing Microbial Communities. Appl. Environ. Microbiol. 75:7537-7541.

Steinbusch K J, Hamelers H V, Schaap J D, Kampman C, Buisman C J. 2010. Bioelectrochemical ethanol production through mediated acetate reduction by mixed cultures. Environ Sci Technol 44:513-517.

Summers Z M, Fogarty H E, Leang C, Franks A E, Malvankar N S, Lovley D R. 2010. Direct exchange of electrons within aggregates of an evolved syntrophic coculture of anaerobic bacteria. Science 330:1413-1415.

Villano M, Aulenta F, Ciucci C, Ferri T, Giuliano A, Majone M. 2010. Bioelectrochemical reduction of $CO(2)$ to $CH(4)$ via direct and indirect extracellular electron transfer by a hydrogenophilic methanogenic culture. Bioresour Technol 101:3085-3090.

Wang Q, Garrity G M, Tiedje J M, Cole J R. 2007. Naive Bayesian classifier for rapid assignment of rRNA sequences into the new bacterial taxonomy. Appl. Environ. Microbiol. 73:5261-5267.

Zhang, T.; Nie, H.; Bain, T. S.; Lu, H.; Cui, M.; Snoeyenbos-West, O. L.; Franks, A. E.; Nevin, K. P.; Russell, T. P.; Lovley, D. R. Improved cathode materials for microbial electrosynthesis. Energy Environ. Sci. 2013, 6 (1), 217.

---

What is claimed is:

1. A method for bioelectric synthesis of $H_2$ and organic compounds comprising:

(a) culturing an electrosynthetic microbial population in a media at a cathode of an electrochemical cell, wherein the electrosynthetic microbial population comprises organisms from at least three families selected from the group consisting of Eubacteriaceae, Campylobacteraceae, Helicobacteraceae, Porphyromonadaceae, WCHB1-69, Spirochaetaceae, Deferribacteraceae, Rhodobacteraceae, Synergistaceae and Rhodocyclaceae wherein the electrosynthetic microbial population comprises bacteria of the genus *Acetobacterium*; and (b) maintaining the microbial culture in the electrochemical cell in the presence of a cathode voltage potential and $CO_2$, thereby producing $H_2$ and at least one organic compound wherein the at least one organic compound comprises methane acetate butyrate isobutyrate propionate, formate or a mixture thereof.

2. The method of claim 1, wherein the electrosynthetic microbial population has previously been cultured at the cathode of an electrochemical cell at a potential of −1000 to −400 mV vs. SHE.

3. The method of claim 2, wherein the electrosynthetic microbial population has previously been cultured at the cathode of an electrochemical cell at a potential of −1000 to −400 mV vs. SHE for at least 30 days.

4. The method of claim 3, wherein the electrosynthetic microbial population has previously been cultured at the cathode of an electrochemical cell at a potential of −1000 to −400 mV vs. SHE for 60 to 180 days.

5. The method of claim 1, wherein the cathode is supplied with a continuous flow of fresh media.

6. The method of claim 1, wherein the at least one organic compound comprises acetate.

7. The method of claim 1, wherein the electrosynthetic microbial population comprises bacteria from the genus *Acetobacterium, Sulfurospirillum* and, optionally, from the family of Rhodobacteraceae.

8. The method of claim 1, wherein the electrosynthetic microbial population has previously been cultured at the cathode of an electrochemical cell at a potential of −590 mV vs. SHE.

9. The method of claim 1, wherein the cathode comprises a material selected from the group consisting of carbon paper, carbon cloth, carbon felt, carbon wool, carbon foam, graphite, porous graphite, graphite powder, graphene, carbon nanotubes, electrospun carbon fibers, a conductive polymer, platinum, palladium, titanium, gold, silver, nickel, copper, tin, iron, cobalt, tungsten, stainless steel, and combinations thereof.

10. The method of claim 9, wherein the cathode is a graphite cathode or a carbon foam cathode.

11. The method of claim 10, wherein the cathode is a graphite granule cathode.

12. The method of claim 10, wherein the cathode is a carbon foam cathode.

13. The method of claim 1, wherein the electrochemical cell is supplied with a continuous flow of $CO_2$.

14. The method of claim 1, wherein the electrochemical cell comprises an anode that is essentially abiotic.

15. The method of claim 1, wherein the microbial population at the cathode is maintained in or has been exposed to an acidic pH.

16. The method of claim 1, further comprising (c) collecting $H_2$ or organic compounds from the electrochemical cell.

* * * * *

UNITED STATES PATENT AND TRADEMARK OFFICE
CERTIFICATE OF CORRECTION

PATENT NO. : 9,879,251 B2
APPLICATION NO. : 14/427374
DATED : January 30, 2018
INVENTOR(S) : Harold D. May et al.

Page 1 of 1

It is certified that error appears in the above-identified patent and that said Letters Patent is hereby corrected as shown below:

On the Title Page

Item (73) Assignee, delete "MEDICAL UNIVERSITY OF SOUTH CAROLINA" as the name of the assignee and insert --MUSC FOUNDATION FOR RESEARCH DEVELOPMENT-- therefor.

In the Claims

In Claim 1, Column 40, Line 62, delete "methane acetate butyrate isobutyrate propi-" and replace with --methane, acetate, butyrate, isobutyrate, propi- -- therefor.

Signed and Sealed this
Thirteenth Day of November, 2018

Andrei Iancu
*Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
agagtttgat ymtggctcag                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
agagtttgat cctggctcag                                          20

<210> SEQ ID NO 3
<211> LENGTH: 17
<212> TYPE: DNA
<213> ORGANISM: Artificial Sequence
<220> FEATURE:
<223> OTHER INFORMATION: Synthetic primer
```

```
<400> SEQUENCE: 3
ackgctcagt aacacgt                                                17

<210> SEQ ID NO 4
<211> LENGTH: 15
<212> TYPE: DNA
<213> ORGANISM: Artificial Sequence
<220> FEATURE:
<223> OTHER INFORMATION: Synthetic primer

<400> SEQUENCE: 4
accgcggckg ctgrc                                                  15

<210> SEQ ID NO 5
<211> LENGTH: 10
<212> TYPE: DNA
<213> ORGANISM: Artificial Sequence
<220> FEATURE:
<223> OTHER INFORMATION: Synthetic primer

<400> SEQUENCE: 5
acgagtgcgt                                                        10

<210> SEQ ID NO 6
<211> LENGTH: 10
<212> TYPE: DNA
<213> ORGANISM: Artificial Sequence
<220> FEATURE:
<223> OTHER INFORMATION: Synthetic primer

<400> SEQUENCE: 6
atcagacacg                                                        10

<210> SEQ ID NO 7
<211> LENGTH: 10
<212> TYPE: DNA
<213> ORGANISM: Artificial Sequence
<220> FEATURE:
<223> OTHER INFORMATION: Synthetic primer

<400> SEQUENCE: 7
agacgcactc                                                        10

<210> SEQ ID NO 8
<211> LENGTH: 10
<212> TYPE: DNA
<213> ORGANISM: Artificial Sequence
<220> FEATURE:
<223> OTHER INFORMATION: Synthetic primer

<400> SEQUENCE: 8
cgtgtctcta                                                        10
```